United States Patent [19]
Mishina

[11] Patent Number: 5,502,166
[45] Date of Patent: Mar. 26, 1996

[54] NMDH RECEPTOR PROTEINS AND GENES ENCODING THE SAME

[75] Inventor: Masayoshi Mishina, Niigata, Japan

[73] Assignee: Mitsubishi Chemical Corporation, Tokyo, Japan

[21] Appl. No.: 26,138

[22] Filed: Feb. 26, 1993

[30] Foreign Application Priority Data

| Feb. 26, 1992 | [JP] | Japan | 4-039563 |
| Jun. 30, 1992 | [JP] | Japan | 4-173155 |
| Aug. 12, 1992 | [JP] | Japan | 4-215017 |
| Nov. 13, 1992 | [JP] | Japan | 4-303878 |

[51] Int. Cl.$^6$ .......................... C07K 14/705; C12N 15/12
[52] U.S. Cl. ................... 530/350; 435/69.1; 435/252.3; 435/320.1; 536/23.5
[58] Field of Search ............................... 438/69.1, 252.3, 438/320.1; 530/350, 24.3, 29.8

[56] References Cited

PUBLICATIONS

Choi, *Neurons*, vol. 1, 1988, pp. 623–634.
McDonald et al, *Brain Research Reviews*, 15, 1990, pp. 41–70.
Wong et al, *Journal of Neurochem.* 1988, pp. 274–281.
Nature 354:31–37, 7 Nov. 1991, Moriyoshi et al. Molecular Cloning and Characterization of the Rat NMDA Receptor.
Science 256:1217–1221, 22 May 1992, Monyer et al Heteromeric NMDA Recepotrs: Molecular and Functional Postinction of Subtypes.

*Primary Examiner*—Garnette D. Draper
*Assistant Examiner*—John D. Ulm
*Attorney, Agent, or Firm*—Jordan and Hamburg

[57] ABSTRACT

Disclosed are a glutamate receptor or a modified glutamate receptor as defined in the Sequence Table, a gene encoding the same and a method for effecting screening an agonist or antagonist which binds to the above glutamate receptor or the above modified glutamate receptor which comprises using the glutamate receptor or the modified glutamate receptor as defined above.

9 Claims, 7 Drawing Sheets

5,502,166

NMDH RECEPTOR PROTEINS AND GENES ENCODING THE SAME

BACKGROUND OF THE INVENTION

This invention relates to novel proteins and genes coding the same, more specifically to protein NMDA (N-methyl-D-aspartic acid) type glutamate receptors which play a central role in nervous information transmission, modified products thereof, and genes (cDNAs) encoding them.

It has been suggested that glutamate receptors, which are receptors of main stimulant nervous transmitter substances in a central nervous system of a higher animal, play a central role in nervous information transmission at a synapse, and also are deeply concerned with appearance of synapse plasticity which is basically required for memory and learning and neuronal cell death caused by a disease such as cerebral ischemia and epilepsy. Thus, it is considered that clarifications of molecular structures and functions of the glutamate receptors are required to understand a transmission mechanism of nervous information in a center, a cerebral structure of higher order and the disease of a brain.

As in the case of receptors of acetylcholine and GABA (γ-aminobutyric acid), the glutamate receptors are roughly classified into ion channel type glutamate receptors and G protein coupled type receptors (metabolism-controlling type receptors). Receptors which can effect long-term reinforcement of synapse transmission at a CA1 region of a hippocampus of which the most advanced study has been made about synapse plasticity are two kinds of ion channel type glutamate receptors. That is, an NMDA type receptor having $Ca^{2+}$ permeability and opening depending on membrane potential and a quisqualate/kinate type receptor (or a non-NMDA type receptor). While the non-NMDA type receptor performs general synapse transmission, the NMDA type receptor performs $Ca^{2+}$ permeation when a high frequent stimulus which induces long-term reinforcement of synapse transmission is given. The $Ca^{2+}$ permeation is inhibited by $Mg^{2+}$ depending on membrane potential.

Although the glutamate receptors have important physiological functions as described above, molecular biological structures thereof had not been clarified for a long term. In recent years, by using a cDNA-producing system of Xenopus oocytes, Hollmann et al. cloned cDNA of a non-NMDA type glutamate receptor ("Nature", 342, pp. 643 to 648 (1989)) and Nakanishi et al. cloned cDNA of a rat-G protein coupled type glutamate receptor ("Nature", 349, pp. 760 to 765 (1991)) and cDNA of a rat-NMDA type receptor ("Nature", 354, pp. 31 to 37 (1991)). Other plural kinds of genes of glutamate receptors have been cloned, and the molecular biological mechanisms thereof have not yet been clarified sufficiently under the present situation.

SUMMARY OF THE INVENTION

The present inventors have paid special attention to NMDA type glutamate receptors and researched and studied them intensively, and consequently novel glutamate receptors and glutamate receptors modified by protein engineering have been obtained to accomplish the present invention.

That is, the characteristic features of the present invention reside in a glutamate receptor which is represented by an amino acid sequence described in Sequence ID No. 1, 2, 3 or 4 of the sequence table and a gene encoding the same, a modified glutamate receptor which is represented by an amino acid sequence described in Sequence ID No. 8 or 9 of the sequence table and a gene encoding the same, and a modified glutamate receptor which is represented by a base sequence described in Sequence ID No. 19 of the sequence table and a gene encoding the same.

BRIEF DESCRIPTION OF THE DRAWINGS

The drawings relating to the present invention are explained.

FIG. 1 (a) represent a current response to 100 μM NMDA +10 μM glycine (NMDA/Gly) of the ε4/ζ1 heteromeric channel, a current response to 10 μM L-glutamate+10 μM glycine (Glu/Gly) of the same and 1 mM $Mg^{2+}$ (Glu/Gly +$Mg^{2+}$) on a current response to Glu/Gly of the same, respectively. FIG. 1(b) represent effects of 500 μM D-2-amino-5-phosphonovalerate (APV) (Glu/Gly +APV) and 100 μM 7-chlorokynurenate (7 CK) (Glu/Gly +7 CK) on a current response of the ε4/ζ1 heteromeric channel to Glu/Gly, respectively.

FIGS. 4(a), 4(b), 4(c) and 4(d) represent an ε2/ζ1 NMDA receptor channel, an ε2/ζ1-N598Q (a modified glutamate receptor shown in Sequence ID No. 9 of the sequence table) NMDA receptor channel, an ε2-N589Q (a modified glutamate receptor shown in Sequence ID No. 8 of the sequence table)/ζ1 NMDA receptor channel and an ε2-N589Q/ζ1-N598Q NMDA receptor channel, respectively.

FIGS. 5(a), 5(b), 5(c) and 5(d) represent an ε2/ζ1 NMDA receptor channel, an ε2/ζ1-N598Q NMDA receptor channel, an ε2-N589Q/ζ1 NMDA receptor channel and an ε2-N589Q/ζ1-N598Q NMDA receptor channel, respectively.

DESCRIPTION OF THE PREFERRED EMBODIMENTS

Figure 1A:
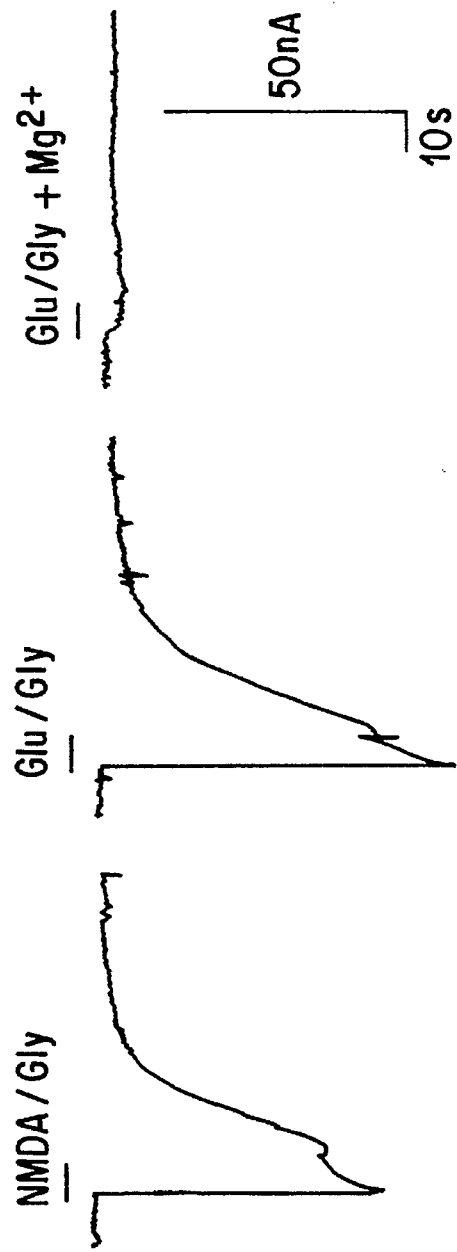
FIGS. 1(a) and 1(b) show functional expression of ε4/ζ1 heteromeric NMDA receptor channel cDNAs in frog oocytes. Current responses are measured at −70 mV membrane potential in normal Ringer's solution.
Figure 1B:
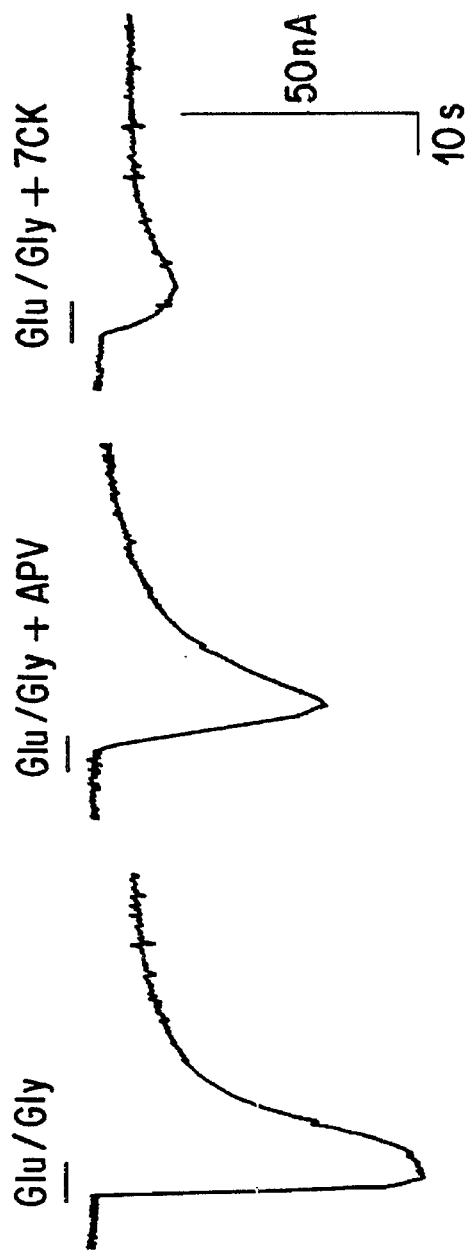

In the following, the present invention is explained in detail.

The glutamate receptor of the present invention has an amino acid sequence as shown in Sequence ID No. 1, 2, 3 or 4 of the sequence table.

The glutamate receptor shown in Sequence ID No. 1 of the sequence table (hereinafter sometimes referred to as "ε1 subunit") is a protein comprising 1464 amino acids. As a gene encoding such a glutamate receptor, there may be mentioned, for example, a base sequence as shown in Sequence ID No. 5 of the sequence table.

The glutamate receptor shown in Sequence ID No. 2 of the sequence table (hereinafter sometimes referred to as "ε2 subunit") is a protein comprising 1482 amino acids. As a gene encoding such a glutamate receptor, there may be mentioned, for example, a base sequence as shown in Sequence ID No. 6 of the sequence table.

The glutamate receptor shown in Sequence ID No. 3 of the sequence table (hereinafter sometimes referred to as "ε3 subunit") is a protein comprising 1239 amino acids. As a gene encoding such a glutamate receptor, there may be mentioned, for example, a base sequence as shown in Sequence ID No. 7 of the sequence table.

The glutamate receptor shown in Sequence ID No. 4 of the sequence table (hereinafter sometimes referred to as "ε4 subunit") is a protein comprising 1323 amino acids. This protein has a signal sequence, and a mature type thereof is considered to start from phenylalanine which is the 28th amino acid in Sequence ID No. 4 of the sequence table. As a gene encoding such a glutamate receptor, there may be mentioned, for example, a base sequence as shown in Sequence ID No. 16 of the sequence table.

The modified glutamate receptor of the present invention has an amino acid sequence as shown in Sequence ID No. 8, 9 or 10 of the sequence table.

The modified glutamate receptor shown in Sequence ID No. 8 of the sequence table (hereinafter sometimes referred to as "ε2-N589Q") is a modified product in which asparagine which is the 589th from the N terminal end of the above ε2 subunit is replaced with glutamine. As a gene encoding such a modified product, there may be mentioned, for example, a base sequence as shown in Sequence ID No. 17 of the sequence table.

The modified glutamate receptor shown in Sequence ID No. 9 of the sequence table (hereinafter sometimes referred to as "ζ1-N598Q") is a modified product in which asparagine which is the 598th from the N terminal end of a ζ1 subunit comprising 920 amino acids ("FEBS Lett", 300 pp 39 to 45 (1992)) is replaced with glutamine. As a gene encoding such a modified product, there may be mentioned, for example, a base sequence as shown in Sequence ID No. 18 of the sequence table.

The modified glutamate receptor shown in Sequence ID No. 10 of the sequence table (hereinafter sometimes referred to as "ζ1-ZAZ") is a modified product in which the 1726th to 1743rd base sequence of the above ζ1 subunit is changed to a base sequence as shown in Sequence ID No. 19 of the sequence table.

In the present invention, there may be included modified glutamate receptors in which amino acids or nucleic acids are partially removed, replaced or added within the range which does not impair activity as a glutamate receptor.

DNA fragments of the glutamate receptor of the present invention and the gene coding the same can be obtained by, for example, the following method.

First, cerebral tissues of a mammal, such as mouse, are homogenized in an aqueous solution containing guanidium thiocyanate or the like, and all RNAs are separated as precipitates by cesium chloride equilibrium density gradient centrifugation or sucrose density gradient centrifugation in accordance with the method of Chirgwin et al. ("Biochemistry", 18, pp. 5294 to 5299 (1979)).

After separation, all RNAs are purified by extraction with phenol, precipitation with ethanol or the like, and the resulting RNAs are purified by oligo (dT) cellulose column chromatography to isolate poly (A)-containing mRNAs (poly $A^+$ mRNAs) including mRNAs of the desired glutamate receptor, whereby an mRNA group can be obtained.

The mRNA group prepared as described above and, for example, primer DNA as described in "FEBS Lett.", 272, pp 73 to 80 (1990) are hybridized, and by using a reverse transcriptase and T4 DNA polymerase, cDNAs with double strands are synthesized and prepared according to a conventional method.

Then, EcoRI linkers are added to both ends of cDNA chains.

The above cDNA chains are inserted into a position of EcoRI cleave site of a λ phage vector such as λgt10 to obtain a recombinant λ phage DNA group.

By using the recombinant λ phage DNA group obtained as described above and using an in vitro packaging kit such as commercially available Gigapack Gold (trade name, produced by Promega Co.) according to an operating manual, the so-called in vitro packaging was carried out to obtain λ phage particles having the recombinant λ phage DNAs. The λ phage particles obtained are increased by transforming host cells such as *Escherichia coli* according to a conventional method.

The clone group obtained is taken and collected on a nylon film or a nitrocellulose film such as Gene Screening Plus (trade name, produced by Du Pont), and protein is removed in the presence of an alkali. The λ phage DNAs including cDNAs are hybridized with a $^{32}P$-labeled probe prepared from fragments of cDNA of a mouse glutamate receptor which has been already cloned ("FEBS Lett.", 272, pp. 73 to 80 (1990)) and a DNA group of these cDNA clones, whereby clones having extremely high possibility of coding the desired glutamate receptor can be narrowed down to several clones.

The modified products are prepared by modifying the respective natural substances of the ε2 subunit and the ζ1 subunit by protein engineering or gene technology. Such a modification method is not particularly limited, and may be carried out specifically by the 2-step polymerase chain reaction (PCR) method by using a suitable synthetic oligonucleotide and DNA fragments derived from a plasmid of pBKSAε2 ("Nature", 358, pp. 36 to 41 (1992)) or pBKSAζ1 ("FEBS Lett.", 300, pp. 39 to 45 (1992)).

For these clones, activity test is conducted by using translation of Xenopus oocytes to obtain cDNA clones encoding the desired glutamate receptor.

The cDNA obtained as described above can be expressed in, for example, transient in vitro protein translation, specifically translation in Xenopus oocytes as described in "Nature", 329, pp. 836 to 838 (1987), or in a host such as a CHO cell transformed by a plasmid for expressing a protein prepared by connecting such a cDNA to downstream of a promoter of a expression plasmid for animal cells. Then, according to a conventional method, the expressed protein is collected to obtain the glutamate receptor of the present invention.

EXAMPLES

The present invention is described in detail by referring to Examples, but it is not intended that the present invention be limited by these Examples.

Example 1

First, a cerebellum of ICR mouse was homogenized in an aqueous solution of guanidium thiocyanate, and then extracted, separated and purified according to the method of Chirgwin et al. ("Biochemistry", 18, PP. 5294 to 5299 (1979)), and subjected to oligo (dT)-cellulose column chromatography according to the method of Aviv et al. ("Proc. Natl. Acad. Sci. USA", 69, pp. 1408 to 1412 (1972)) to isolate poly (A)-containing mRNAs (poly $A^+$ mRNAs) containing mRNAs of an NMDA type glutamate receptor.

By using a cDNA synthesizing kit produced by Bethesda Research Laboratories Co., cDNAs having double strand were prepared from the poly $A^+$ mRNAs. Both ends of the cDNAs were blunt-ended with T4 DNA polymerase, and the cDNAs were methylated by using an EcoRI-methylase. Then, EcoRI linkers were added to both ends of the cDNAs by ligase to prepare cDNA fragments having an EcoRI restriction site at both ends by digestion with an EcoRI restriction enzyme.

The cDNAs obtained as described above were subjected to 1.5% agarose gel electrophoresis to select and collect cDNAs having a size of 0.5 Kb or more.

The obtained cDNA fragments having a size of 0.5 Kb or more were linked to λgt10 phage DNAs by ligase, and the cDNAs were inserted into an EcoRI cleaved site of λgt10 to constitute a λgt10 cDNA library according to a conventional method. By using the λgt10 cDNA library obtained and using an in vitro packaging kit Gigapack Gold (trade name, produced by Promega Co.) according to an operating manual, in vitro packaging was carried out to obtain λ phage particles having recombinant λ phage DNAs. The λ phage particles obtained were cultivated by transforming Escherichia coli of host cells according to a conventional method.

The clone group obtained was taken and collected on a nylon film or Gene Screening Plus (trade name, produced by Du Pont), and protein was removed in the presence of an alkali. Then, screening of the cDNA library was carried out. BamHI DNA fragments (1348 to 1946) and HincII DNA fragments (1279 to 2239) (previously cloned cDNA fragments of mouse glutamate receptors) of a pKCR30 plasmid ("FEBS Lett.", 272, pp. 73 to 80 (1990)) were labeled with $^{32}P$ to prepare probes and the plaque hybridization was done in the presence of 30 % formaldehyde at 37° C.

According to the method described above, some cDNA clones encoding the novel glutamate receptor were obtained. Among them, cDNA fragments from a recombinant phage λ A19 having the ε1 subunit cDNAs which was considered to be a subunit of the NMDA type glutamate receptor ion channel were subcloned at an EcoRI site of pBluescript IISK (−) plasmid (trade name) produced by Stratagene Co. to obtain a pGRA19 plasmid. By using the A19 cDNA fragments and other cDNA fragments (AT11) obtained by the same method as that of A19 cDNA fragments as probes, screening was carried out in the presence of 30% formamide at 45° C. to obtain ε1 subunit cDNA clones. The cDNA-inserted fragments obtained from the total 7 recombinant phages were inserted into an EcoRI site of a pBKSA plasmid, a plasmid obtained by inserting:

5'-CCAGGTGCA-3'
3'-ACGTGGTCC-5' (Sequence ID No. 11 in the sequence table) into a PstI site of pBluescript IIKS (+) (trade name, produced by Stratagene Co.) in the same direction as that of a T3 promoter) to prepare plasmids pAT4, pAT11, pAT12, pAT19, pAT20, pAT201 and pAT202.

All base sequences of A19 (the −327th to 3181st of base pair) and AT19 (the 2859th to 5470th of base pair) were determined according to the dideoxy chain termination method of Sanger et al. ("Proc. Natl. Acad. Sci. USA", 74, pp. 5463 to 5467 (1977)). Base pair numbers were given from the 5' end to the 3' end, and negative numbers were given to base pairs before a codon corresponding to the amino terminal end of the ε1 subunit. The partial DNA base sequences: base sequences of clone AT4 (the 2550th to 3432nd of base pair), AT11 (the 2550th to 3622nd of base pair), AT12 (the 2404th to 3622nd of base pair), AT20 (the 2550th to 3177th of base pair), AT201 (the 3526th to 4401st of base pair) and AT202 (the 3409th to 4371st of base pair) were completely the same with the corresponding base sequences of A19 and AT19. The base sequences and the amino acid sequences were analyzed by GENETYX Software (SDC). As a result, the amino acid sequence of the ε1 subunit was a sequence shown in Sequence ID No. 1 of the sequence table, and the base sequence encoding the ε1 subunit was a sequence shown in Sequence ID No. 5 of the sequence table.

The ends of EcoRI DNA fragments with a size of 3.5 Kb derived from the pGRA19 plasmid were bluntended by using T4 DNA polymerase and inserted into a SmaI site of a pSP64AX plasmid ("FEBS Lett.", 259, pp. 37 to 42 (1989)) in the same direction with respect to an SP6 promoter to obtain a pSPA19 plasmid. SalI/HindIII DNA fragments with a size of 3.0 Kb derived from the pSPA19 plasmid, HindIII/NcoI DNA fragments with a size of 0.36 Kb derived from the same and NcoI/SalI DNA fragments with a size of 5.4 Kb derived from the pAT19 plasmid were linked by ligase to prepare a pBKSA ε1.

Then, by using the pBKSA ε1 cut by NotI as a template and using T3 RNA polymerase produced by BRL Co., ε1-specific mRNAs were synthesized in vitro. Transcription was carried out in a solution containing ATP, TTP and CTP at a concentration of 0.5 mM, respectively and 0.1 mM GTP in the presence of 0.5 mM dinucleotide 7mGpppG having a cap structure (in which 2 Gs were linked at 5' and 7-site of one guanine was methylated, produced by P-L Biochemicals Co.). One or both of ε1 subunit-specific mRNAs and ζ1.NMDA type glutamate receptor subunit-specific mRNAs (mRNAs derived from mice, coding an amino acid sequence different in the 213rd (Glu→Asp) and the 460th (Ile→Val) from the N terminal end from the amino acid sequence which is coded by cDNA.-NMDA R1 of a rat-NMDA type glutamate receptor cloned by Nakanishi et al. ("Nature", 354, pp. 31 to 37 (1991))) were injected into Xenopus oocytes.

The oocytes used were obtained from mature female Xenopus and separated into one oocyte in a Barth medium by using sharp tweezers and scissors. The concentration of the mRNAs was 0.1 µg/µl and 10 µl thereof was injected into about 100 oocytes in an amount of 50 to 100 nl per one oocyte. The mRNAs were injected under a microscope by using a capillary and a micromanipulator. After the injection, the oocytes were incubated at 19° C. for one day in a Barth medium containing 0.1 mg/ml of gentamicin ("The Control of Gene Expression in Animal Development, Clarendon, Oxford (1974)). Then, the oocytes were allowed to stand in 1 mg/ml of collagenase at room temperature for 1 hour, and then extracellular skins were removed under a microscope by using sharp tweezers. These oocytes were returned to the Barth medium containing 0.1 mg/ml of gentamicin, incubated again at 19° C. for one day and then used for an electrophysiological test.

The electrophysiological test was carried out by a conventional micropipet voltage clamp method. Oocytes generally have a membrane potential of about −30 to −40 mV. First, while a frog standard Ringer's solution (115 mM NaCl, 2.5 mM KCl, 1.8 mM $CaCl_2$ and 10 mM HEPES-NaOH (pH: 7.2)) was flown in a chamber, 2 glass micro-electrodes charged with 3M KCl were stuck in the oocytes, and the membrane potential was fixed to −70 mV. In these oocytes, an agonist (NMDA) is linked to a glutamate receptor expressed on a cell membrane and an ion channel is opened, the oocytes have an action of returning membrane potential to an original value, whereby inflow and outflow of ions are caused. In the present experiment system, flow of these ions were detected, and opening and closing of the ion channel were observed.

The $\epsilon1$ subunit-specific mRNAs synthesized from the cloned cDNAs in vitro were injected into the Xenopus oocytes. The injected oocytes did not show any reaction to 10 µM L-glutamate and 100 µM NMDA even in the presence of 10 µM glycine which was an essential activating factor of the NMDA type receptor channel. However, when the $\epsilon1$ subunit-specific mRNAs and the $\zeta1$.NMDA type receptor subunit-specific mRNAs were injected simultaneously, significant reaction was observed. In a frog standard Ringer's solution, the inward current at a membrane potential of −70 mV was 364±62 nA (average±standard deviation, n=7) with respect to 10 µM L-glutamate and 10 µM glycine and 175±30 nA (n=7) with respect to 100 µM NMDA and 10 µM glycine. The current amplitude was extremely larger than that of the case where only the $\zeta1$.NMDA type receptor subunit-specific mRNAs were injected to the oocytes (8±2 nA (n=7) with respect to 10 µM L-glutamate and 10 µM glycine and 6±1 nA (n=7) with respect to 100 µM NMDA and 10 µM glycine). In a $Ba^{2+}$ Ringer's solution (in which $Ca^{2+}$ in the standard Ringer's solution described above was replaced, with $Ba^{2+}$), the current amplitudes with respect to 10 µM L-glutamate and 10 µM glycine, and 100 µM NMDA and 10 µM glycine were 84±4 nA and 57±3 nA (n=7), respectively, when the $\epsilon1$ and $\zeta1$ subunits were expressed at the same time, and 2±0.4 nA and 1±0.2 nA (n=7), respectively, when only the $\zeta1$ subunit was expressed. From the results described above, it was concluded that the $\epsilon1$ protein was a subunit of the NMDA type glutamate receptor ion channel.

Example 2

Using the 1388 base pair KpnI/HindIII DNA fragments derived from the pGRA 19 plasmid obtained in Example 1 as probes, the mouse brain cDNA library obtained from λgt10 in Example 1 was screened under mild conditions to obtain $\epsilon2$ subunit cDNA clone U9 and two $\epsilon3$ subunits, cDNA clone U20 and He49. The cDNA fragments were inserted into the EcoRI site of pBluescript IISK (−) (Stratagene) to obtain pGRU9, pGRU20 and pGRHe49 plasmids. By using 445 base pair DraIII/EcoRI derived from pGRU9 plasmid, 2847 base pair HindIII/EcoRI fragments, 1615 base pair EcoRI fragments derived from pGRHe49 and 314 base pair HindIII/EcoRI fragments derived from pGRUN3 as probes, screening was performed under severe conditions to isolate further some clones (as the $\epsilon2$ subunit cDNA clones, U4, U2, U7, U8, U11, U16, U17 and U22, and as the $\epsilon3$ subunit cDNA clones, UN6, UN3 and UT5). These inserted cDNAs in recombinant phage were inserted into the EcoRI site of the aforesaid pBSKA plasmid.

All base sequences of the $\epsilon2$ subunit cDNA clones U9 (the −417th to 3218th base pair) and U4 (the 1117th to 4454th base pair) were determined according to the dideoxy chain termination method as described above. Base sequences of clones U2 (the 4319th to 4396th base pair), U7 (the −417th to 3616th base pair), U8 (the 4319th to 4396th base pair), U11 (the 4319th to 4396th base pair), U16 (the −205th to −57th base pair), U17 (the −205th to −57th base pair) and U22 (the 1449th to 4365th base pair) were completely coincident with the corresponding base sequences of U9 and U4.

In the $\epsilon3$ subunit cDNA clones UN6 (the −232nd to 3283th base pair), He49 (the −101st to 1504th base pair), UN3 (the 52nd to 4039th base pair), U20 (the 347th to 2016th base pair) and UT5 (the 2487th to 4071st base pair), base sequences were completely identical therewith except for the 711st (T or C), 1485th (A or G), 1494th (A or G) and 2721st (T or C). Base pair numbers were started from a codon coding an amino terminal end amino acid of a mature type subunits and given a direction from the 5' end to the 3' end. The base sequences and the amino acid sequences were analyzed by GENETYX Software. As a result, the amino acid sequence of the mature type $\epsilon2$ subunit was a sequence shown in Sequence ID No. 2 of the sequence table, and the base sequence coding the $\epsilon2$ subunit was a sequence shown in Sequence ID No. 6 of the sequence table. Also, the amino acid sequence of the mature type $\epsilon3$ subunit was a sequence shown in Sequence ID No. 3 of the sequence table, and the base sequence coding the $\epsilon2$ subunit was a sequence shown in Sequence ID No. 7 of the sequence table.

EcoRI/PvuI DNA fragments with a size of 3.5 Kb derived from the pGRU9 and PvuI/EcoRI DNA fragments with a size of 1.6 Kb derived from the pGRU4 (U4 clone derivative) were linked to EcoRI DNA fragments with a size of 3.0 Kb derived from the pBKSA by ligase to obtain pBKSA $\epsilon2$ plasmids. SalI DNA fragments with a size of 864 bp derived from the pGRUN6 (UN6 clone derivative) and SalI DNA fragments having a size of 6.4 Kb derived from the pGRUN3 (UN3 clone derivative) were linked by ligase to obtain pBKSA $\epsilon3$.

Then, by using the pBKSA $\epsilon2$ cut by NotI and the pBKSA $\epsilon3$ cut by XbaI as molds and using T3 RNA polymerase produced by BRL Co., $\epsilon2$-specific mRNAs and $\epsilon3$-specific mRNAs were synthesized in vitro. Transcription was carried out in the same manner as in Example 1.

The $\epsilon1$ (not more than 22 ng/egg) subunit-specific mRNAs obtained in Example 1, the $\epsilon2$ (not more than 19 ng/egg) subunit-specific mRNAs, the $\epsilon3$ (not more than 16 ng/egg) subunit-specific mRNAs and $\zeta1$ (not more than 13 ng/egg) NMDA type glutamate receptor subunit-specific mRNAs described above were used singly or in combination, they were injected into the Xenopus oocytes in the same manner as in Example 1. 10 µl of the mRNA aqueous solution was injected into about 100 oocytes in an amount of 50 to 100 nl per one oocyte. The oocytes after the injection were treated in the same manner as in Example 1 and then used for an electrophysiological test.

The ε2 or ε3 subunit-specific mRNAs synthesized from the cloned cDNAs in vitro were injected into the Xenopus oocytes with the ξ1 subunit-specific mRNAs. In a frog standard Ringer's solution, the inward current of ε2 and ξ1 subunits expressing oocytes at a membrane potential of −70 mV was 667±187 nA (average±standard deviation) with respect to 10 µM L-glutamate and 10 µM glycine and 546±172 nA (N=5) with respect to 100 µM NMDA and 10 µM glycine, and in ε3 and ξ1 subunits expressing oocytes, it was 191±67 nA with respect to 10 µM L-glutamate and 10 µM glycine and 89±22 nA (n=7) with respect to 100 µM NMDA and 10 µM glycine. The current amplitude was extremely larger than that of the case where only the ζ1.NMDA type receptor subunit-specific mRNAs were injected to the oocytes (11±1 nA, n=12, with respect to 10 µM L-glutamate and 10 µM glycine and 9±2 nA, n=7, with respect to 100 µM NMDA and 10 µM glycine). No response was observed in the oocytes to which the ε2 or ε3 subunit-specific mRNAs were injected singly (<1 nA). In the oocytes in which the ε2 and ε1 subunits, or the ε3 and ξ1 subunits were expressed, responses to 100 µM kainate and to 100 µM AMPA were less than the measurement limit.

The ε2/ξ1 heteromeric channel showed a response to 10 µM L-glutamate and 10 µM glycine and to 100 µM L-aspartic acid alone. On the other hand, the ε3/ξ1 heteromeric channel showed a response only to 10 µM glycine. The response to 10 µM L-glutamate or 10 µM glycine alone disappeared by 100 µM of D-2-amino-5-phosphonovalerate (APV) which is a specific competitive antagonist of the NMDA receptors and 30 µM 7-chlorokynurenate (7 CK) which had been reported as a competitive antagonist to glycine control site of the NMDA receptors. The response to 10 µM L-glutamate and 10 µM glycine can be suppressed by these competitive antagonists, non-competitive antagonists, 100 µM $Mg^{2+}$, 100 µM $Zn^{2+}$, or 1 µM (+)-MK-801 (an open channel blocker of the NMDA type receptor channel). The effect of the channel blocker to the ε3/ξ1 channel is weaker than those to the ε1/ξ1 and ε2/ξ1 channels. The ε2/ξ1 and ε3/ξ1 channels each showed an inward current in a $Na^+$ and $K^+$-free Ringer's solution containing 20 mM $Ca^{2+}$ ($Ca^{2+}$-Ringer's solution), but in a control $Na^+$ and $K^+$-free Ringer's solution, a slightly outward current could be observed. This shows that the heteromeric channels permeate $Ca^{2+}$. According to the above, it can be concluded that ε2 and ε3 proteins are subunits of the NMDA receptor channels.

In order to minimize effects of a secondary activated $Ca^{2+}$ dependent Cl- current on a dose-reaction curve to L-glutamate and glycine of the heteromeric NMDA receptor channel, it was examined in a $Ba^{2+}$ Ringer's solution. $EC_{50}$ values to ε1/ξ1, ε2/ξ1 and ε3/ξ1 channels were each 1.7 µM, 0.8 µM and 0.7 µM and those to glycine were each 2.1 µM, 0.3 µM and 0.2 µM. Hill coefficient value was 1.2 to 2.2. Effects of the competitive antagonist were examined with 10-fold concentration of the antagonist concentration used when examining the $EC_{50}$ values. The strength in sensitivity to APV was in the order of ε1/ξ1>ε2/ξ1>ε3/ξ1 and that to 7 CK was in the order of ε3/ξ1>ε2/ξ1>ε1/ξ1. 0.1 mM and 1 mM of $Mg^{2+}$ acted on the ε/ξ heteromeric NMDA channels voltage-dependently and repressively. However, clear difference can be found between these heteromeric channels. The ε3/ξ1 channel showed resistance to $Mg^{2+}$ inhibition, and showed activity at membrane potentials of −70 mV and −100 mV in the presence of 1 mM $Mg^{2+}$. On the other hand, under the same conditions, the ε1/ξ1 and ε2/ξ1 channels were strongly repressed. These results suggest that functionally different NMDA receptor channels were formed according to the combination of the subunits.

Example 3

Amino acid sequences highly preserved of mouse NMDA type receptor subunits, i.e. an oligo nucleotide sense primer, 5'-TGGAAT/CGGA/TATGATG/A/T/CGGG/A/T/CGA-3' (sequence ID No. 14 of the sequence table) corresponding to WNGMI/MGE (sequence ID No. 12 of the sequence table) existing at an upstream end of the membrane spanning region M1 and an oligo nucleotide antisense primer, 5'-GCG/A/TGCT/CAG/AG/ATTG/A/TGCG/A/T/CG/ ATG/ATA-3' (sequence ID No. 15 of the sequence table) corresponding to YTANLAA (sequence ID No. 13 of the sequence table) in M3 were synthesized. Polymerase chain reaction (PCR) was carried out using the double strand cDNA as a template and the above synthesized oligo nucleotides as primers. PCR was carried out 30 cycles in total in which, after incubation at 94° C. for 3 minutes in 50 µl of the reaction solution containing 10 mM of Tris-HCl (pH 8.3), 50 mM of KCl, 1.5 mM of $MgCl_2$, 0.001% of gelatin, 20 ng or less of a mouse cerebrum cDNA, 2 µM of the respective primers, 200 µM of 4 kinds of deoxynucleotide triphosphate and 4 units of Taq polymerase; 94° C. for 1 minute; 50° C. for 1 minute; and 72° C. for 1.5 minutes were as one cycle.

After treating the PCR products by T4 DNA polymerase, they were inserted into the HincII site of pBluescript IISK (+) plasmid (Stratagene).

Subsequently, according to screening and base sequence determination, ε4 subunit cDNA clone was identified. The thus determined base sequence of the ε4 subunit cDNA and amino acid sequence expected therefrom were each shown in sequence ID No. 4 of the sequence table.

In the same manner as in Example 1 except for using a mouse cerebrum and cerebellum, cDNA library obtained from λgt10 was screened by using the ε4 subunit cDNA as a probe to obtain several clones which code the ε4 subunit. These phage-derived cDNA fragments were inserted into EcoRI site of the pBluescript IISK (−) plasmid (Stratagene) or pBKSA plasmid.

Base sequences of both chains of cDNA clones SE11 (from the −33rd to 2550th at the 5' end upstream in Sequence ID No. 16 of the sequence table) and SE4 (from the 2515th to +83st at the 3' end downstream in Sequence ID No. 16 of the sequence table) were determined according to the dideoxy chain termination method using various primers synthesized by the DNA autosysnthesizer (available from Applied Biosystem Co.). Partial base sequences of respective clones, SE1 (the −33rd of the 5' upstream region to 2001st of the sequence No. ID No. 16 in the sequence table), TSEE6 (the 1716th to 2291st of the sequence No. ID No. 16 in the sequence table) and K1 (the 2013rd to +83rd of the 3' down stream region of the sequence No. ID No. 16 in the sequence table) were completely identical with the sequences of the cDNA clones SE4 and SE11. The base sequences and the amino acid sequences were analyzed by GENETYX Software (SDC).

All coding area (the 1st to +3rd of the 3' down stream region in the Sequence ID No. 16 of the sequence table, i.e. until stop codon)) of the ε4 subunit cDNA was inserted by pSP35T plasmid and PCR method according to the PCR method between the NcoI and XbaI portions of the pSP35 plasmid (Cell, 66, pp. 257 to 270 (1991)) to obtain pSPGR ε4 plasmid.

Then, by using the pSPGR ε4 plasmid cut by EcoRI as a template and using SP6 RNA polymerase, ε4-specific mRNAs were synthesized in vitro. Transcription was carried out in the same manner as in Example 1.

The ε4 subunit-specific mRNAs (not more than 16 ng/egg) synthesized in vitro from a cloned cDNA and ξ1.NMDA type glutamate receptor subunit-specific mRNAs (not more than 13 ng/egg) described above were used singly or in combination, they were injected into the Xenopus oocytes in the same manner as in Example 1. 10 µl of the mRNA aqueous solution was injected into about 100 oocytes in an amount of 50 to 100 nl per one oocyte. The oocytes after the injection were treated in the same manner as in Example 1 and then used for an electrophysiological test.

Figure 2:
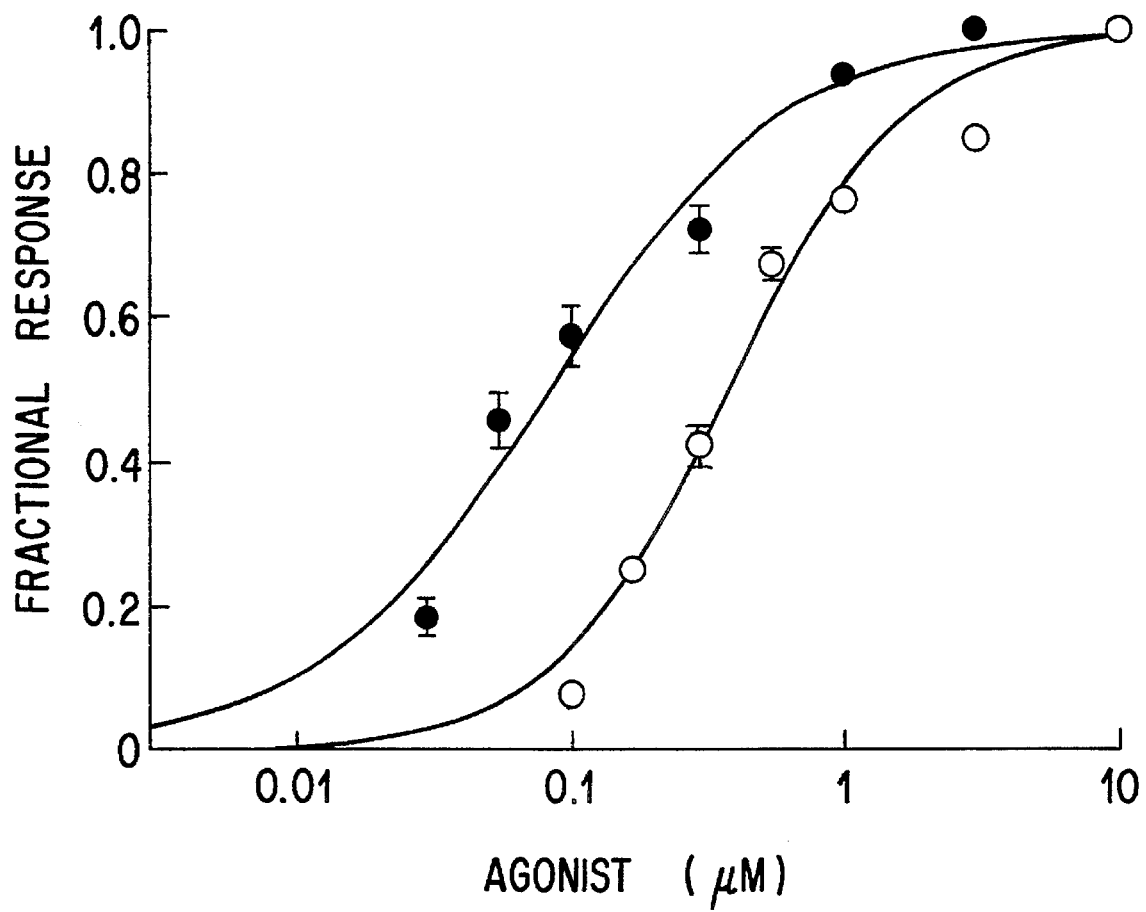
FIG. 2 shows pharmacological properties of the ε4/ζ1 heteromeric NMDA receptor channel. Current responses are measured at −70 mV membrane potential in a $Ba^{2+}$-Ringer's solution. In the figure, dose-response relationship for L-glutamate (○) and glycine (●) in the presences of 10 μM glycine and 10 μM L-glutamate (each point represents the mean fractional responses obtained from 4 oocytes) are shown.
Figure 3:
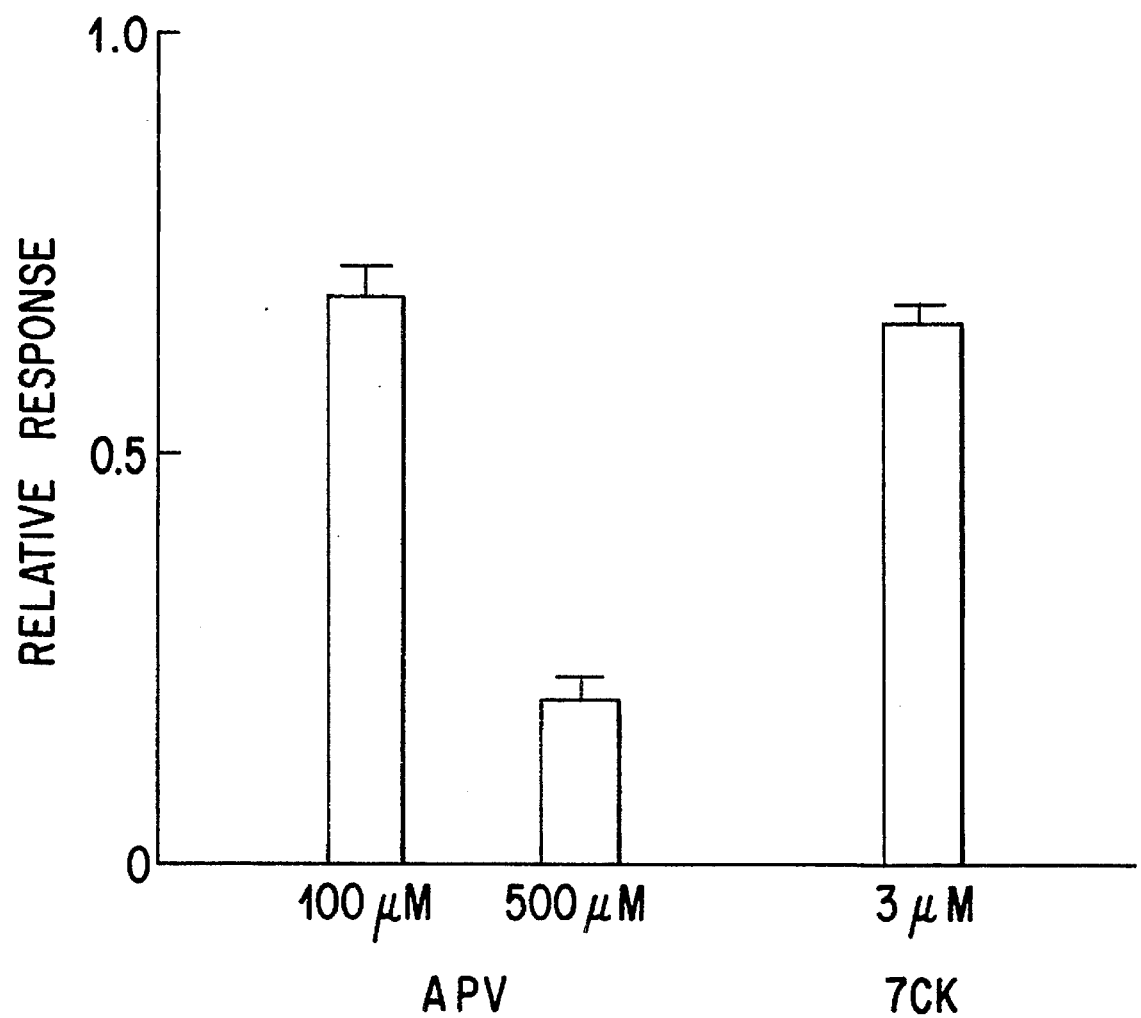
FIG. 3 shows pharmacological properties of the ε4/ζ1 heteromeric NMDA receptor channel. Current responses are measured at −70 mV membrane potential in a $Ba^{2+}$-Ringer's solution. In the figure, influences of APV and 7 CK on response to 4.7 μM L-glutamate +0.9 μM glycine (the concentrations of agonists were 10-folds the respective $EC_{50}$ values) are shown.
Figure 4A:
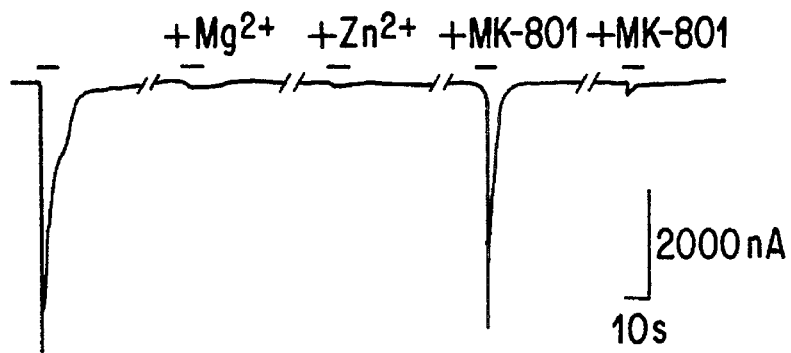
FIGS. 4(a) to 4(d) show a current response of the heteromeric NMDA receptor channel to 10 μM L-glutamate +10 μM L-glycine at −70 mV membrane potential in a frog standard Ringer's solution. In the figures.
Figure 4B:
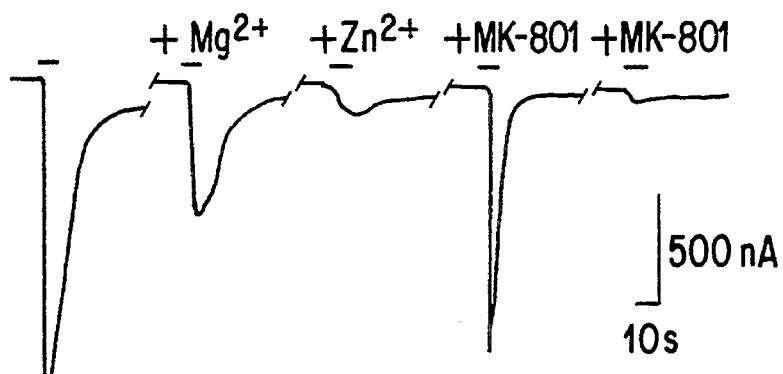
Figure 4C:
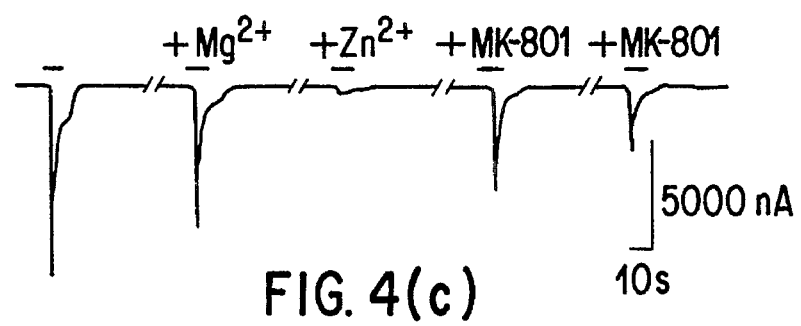
Figure 4D:
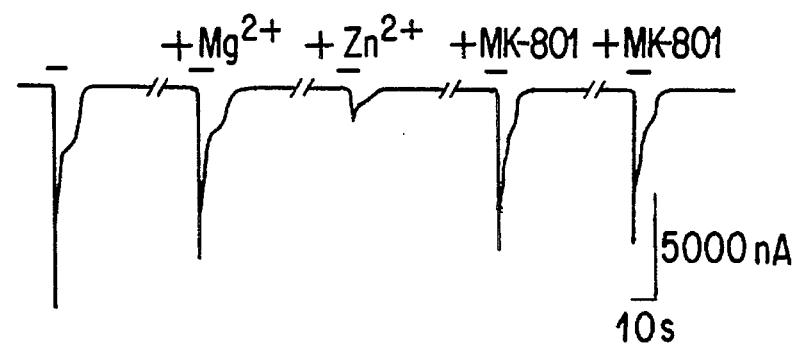
Figure 5A:
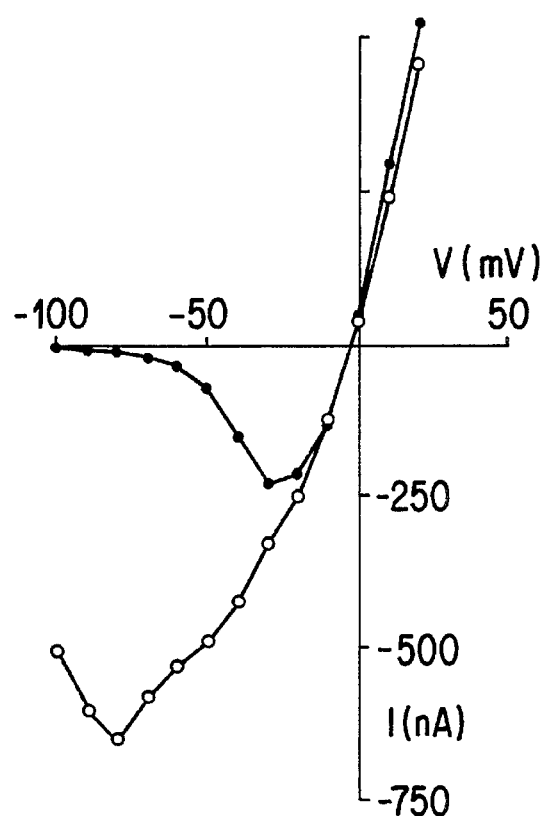
FIGS. 5(a) to 5(d) show current-voltage relationships of wild type and mutant heteromeric channels in the presence of 1 mM $Mg^{2+}$ (●) and in the absence thereof (○). In the figures.
Figure 5B:
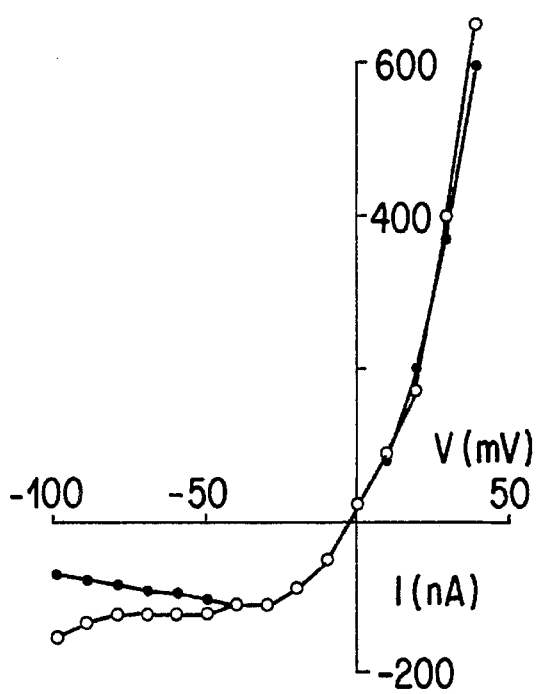
Figure 5C:
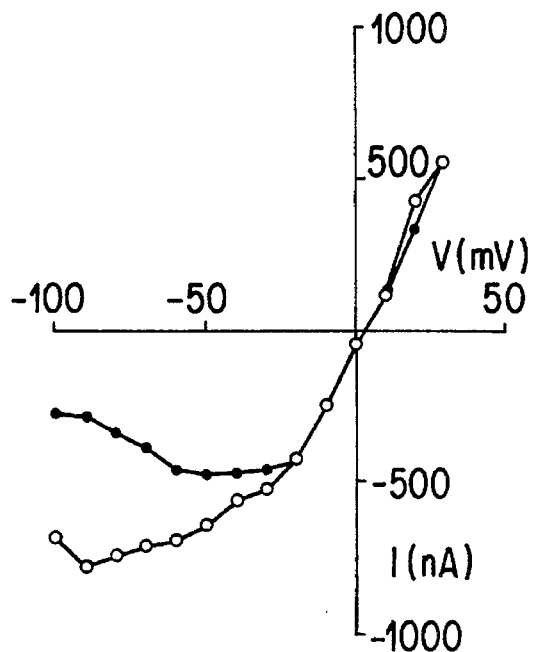
Figure 5D:
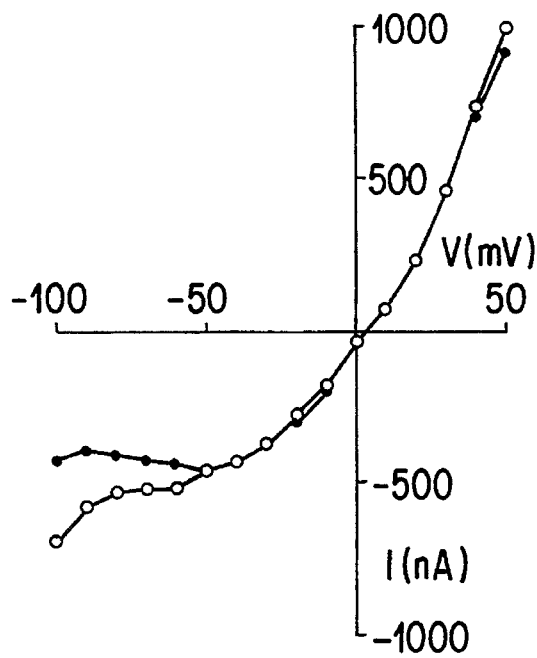

In a frog standard Ringer's solution, the inward current of ε4 and ξ1 subunits expressing oocytes at −70 mV membrane potential was 70±9 nA (mean±standard deviation, n=13) with respect to 10 µM L-glutamate and 10 µM glycine and 68±13 nA (n=8) with respect to 100 µM NMDA and 10 µM glycine (FIG. 1(a)). The current amplitude was extremely larger than that of the case where only the ζ1.NMDA type receptor subunit-specific mRNAs were injected to the oocytes (17±1 nA, n=10, with respect to 10 µM L-glutamate and 10 µM glycine and 13±2 nA, n=7, with respect to 100 µM NMDA and 10 µM glycine). The response of the heteromeric channel comprising the ε4/ξ1 subunit to 10 µM L-glutamate and 10 µM glycine was suppressed by 500 µM APV which is a specific competitive antagonist of the NMDA receptors or 100 µM of 7 CK which had been reported as a competitive antagonist to glycine control site of the NMDA receptors (FIG. 2 and FIG. 3). According to the above, it can be concluded that ε4 protein is a subunit of the NMDA receptor channels.

Since the suppressive effect of the NMDA receptor competitive antagonist to the e4 subunit was relatively small, the pharmacological characteristics of the ε4/ξ1 heteromeric channel were quantitatively examined by using a $Ba^{2+}$ Ringer's solution. The $EC_{50}$ values to L-glutamate or glycine obtained from the dose-reaction curve were 0.4 µM and 0.09 µM, respectively, and the Hill coefficients were 1.4 and 1.2, respectively (FIG. 2).

Apparent affinity of the ε4/ξ1 heteromeric NMDA receptor channel to an agonist was stronger than those of the ε1/ξ1, ε2/ξ1 and ε3/ξ1 heteromeric channels. The strengths in affinity to L-glutamate and glycine were in the order of ε4/ξ1>ε3/ξ1>ε2/ξ1. The effects of APV and 7 CK were examined by 10-fold concentration of the $EC_{50}$ value (FIG. 3). Activities of the ε4/ξ1 channel were only decreased by 31% in 100 µM APV and 34% in 3 µM 7 CK. The degree of inhibition was smaller than those of the other ε/ξ channels observed under the same conditions. The sensitivities to APV were ε1/ξ1>ε2/ξ1>ε3/ξ1>ε4/ξ1, and those to 7 CK were ε3/ξ1>ε2/ξ1>ε1/ξ1=ε4/ξ1. According to the above, the ε4/ξ1 heteromeric channel was characterized that it has strong affinity to an agonist and weak sensitivity to a competitive antagonist.

Example 4

By using the mouse brain cDNA library obtained from λgt10 in Example 1, screening of the cDNA library was carried out. Then, KpnI/HindIII DNA fragments (1388 base pairs: previously cloned cDNA fragments of mouse glutamate receptors) of a pGRA19 plasmid obtained in Example 1 and mouse α1 and α2 subunit cDNAs (FEBS, Lett., 272, pp. 73 to 80 (1990)) were labeled with $^{32}P$ and plaque hybridization was done in the presence of 30 % formaldehyde at 37° C.

Partially specific modification was carried out by using a suitable synthesized oligo nucleotide and pBKSA ε2 obtained in Example 2 and pBKSA ξ1 (FEBS, Lett., 300, pp. 39 to 45 (1992)) plasmid-derived DNA fragments according to the two-step polymerase chain reaction (PCR) method. The resulting modified 353 base pairs Cfr101SphIand 322 base pairs FspI/BlnI DNA fragments obtained by amplifying according to the PCR were substituted for the corresponding segments of pBKSA ε2 and pBKSA ξ1, respectively. The nucleotide sequences of the constructed plasmids are different from those of the original plasmids as follows.

pBKSA ε2-N589Q (in the ε2 subunit described in the sequence ID No. 2 and No. 6 of the sequence table, asparagine which is an amino acid at the 589th from the N-terminal is modified to glutamine, A which is the 1765th base sequence to C and C which is the 1767th base sequence to G, respectively. The amino acid sequence and base sequence are shown in sequence ID No. 8 and No. 17 of the sequence table, respectively.)

pBKSA ζ1-N598Q (in the ζ1 subunit described in "FEBS Lett.", 300, pp. 39 to 45 (1992), asparagine which is an amino acid at the 598th from the N-terminal is modified to glutamine, A which is the 1792nd base sequence to C and C which is the 1794th base sequence to G, respectively. The amino acid sequence and base sequence are shown in sequence ID No. 9 and No. 18 of the sequence table, respectively.)

pBKSA ζ1-ZAZ (in the ζ1 subunit described in "FEBS Lett.", 300, pp. 39 to 45 (1992), the 1726th to 1743rd base sequence is modified to ACCAGTGACCAGTCAAAT. The amino acid sequence and base sequence are shown in sequence ID No. 10 and No. 19 of the sequence table, respectively.)

Next, by using the pBKSA ε2 and pBKSA ζ1 plasmids and derivatives thereof cut by suitable restriction enzymes as template and using T3 RNA polymerase produced by BRL Co., ε2, ζ1 and their derivatives-specific mRNAs were synthesized in vitro, respectively. Transcription was carried out in the same manner as in Example 1.

In order to examine influence on the modified ion channels, the wild type or modified ε2 (not more than 19 ng/oocyte) subunit-specific mRNAs and the wild type or modified ζ1 (not more than 13 ng/oocyte) subunit-specific mRNAs were injected singly or in combination into the Xenopus oocytes in the same manner as in Example 1. 10 µl of the mRNA aqueous solution was injected into about 100 oocytes in an amount of 50 to 100 nl per one oocyte. The oocytes after the injection were treated in the same manner as in Example 1 and then used for an electrophysiological test.

FIGS. 4(a) to 4(d) show a current response of the heteromeric NMDA receptor channel to 10 µM L-glutamate and 10 µM L-glycine at −70 mV membrane potential in a frog standard Ringer's solution. The wild type ε2/ζ1 NMDA receptor channel was strongly inhibited by 1 mM $Mg^{2+}$, 100 µM $Zn^{2+}$ and 1 µM (+)-MK-801. MK-801. To the contrary, the modified ε2/ζ1-N598Q channel showed a great current response even in the presence of 1 mM $Mg^{2+}$. However, the response was suppressed effectively by 100 µM $Zn^{2+}$ and 1 µM (+)-MK-801. Similarly, in the ε2-N589Q modified product, sensitivity to $Mg^{2+}$ inhibition was decreased without changing sensitivity to $Zn^{2+}$. To the $\epsilon2/\zeta1$ and $\epsilon2/\zeta1$-N598Q channels, the $\epsilon2$-N589Q/$\zeta1$ channel showed a great current response after repetitive application of (+)-MK-801. The heteromeric $\epsilon2$-N589Q/$\zeta1$-N598Q channel showed strong resistance to $Mg^{2+}$ and (+)-MK-801 inhibitions, but still had sensitivity to $Zn^{2+}$.

Figure 6:
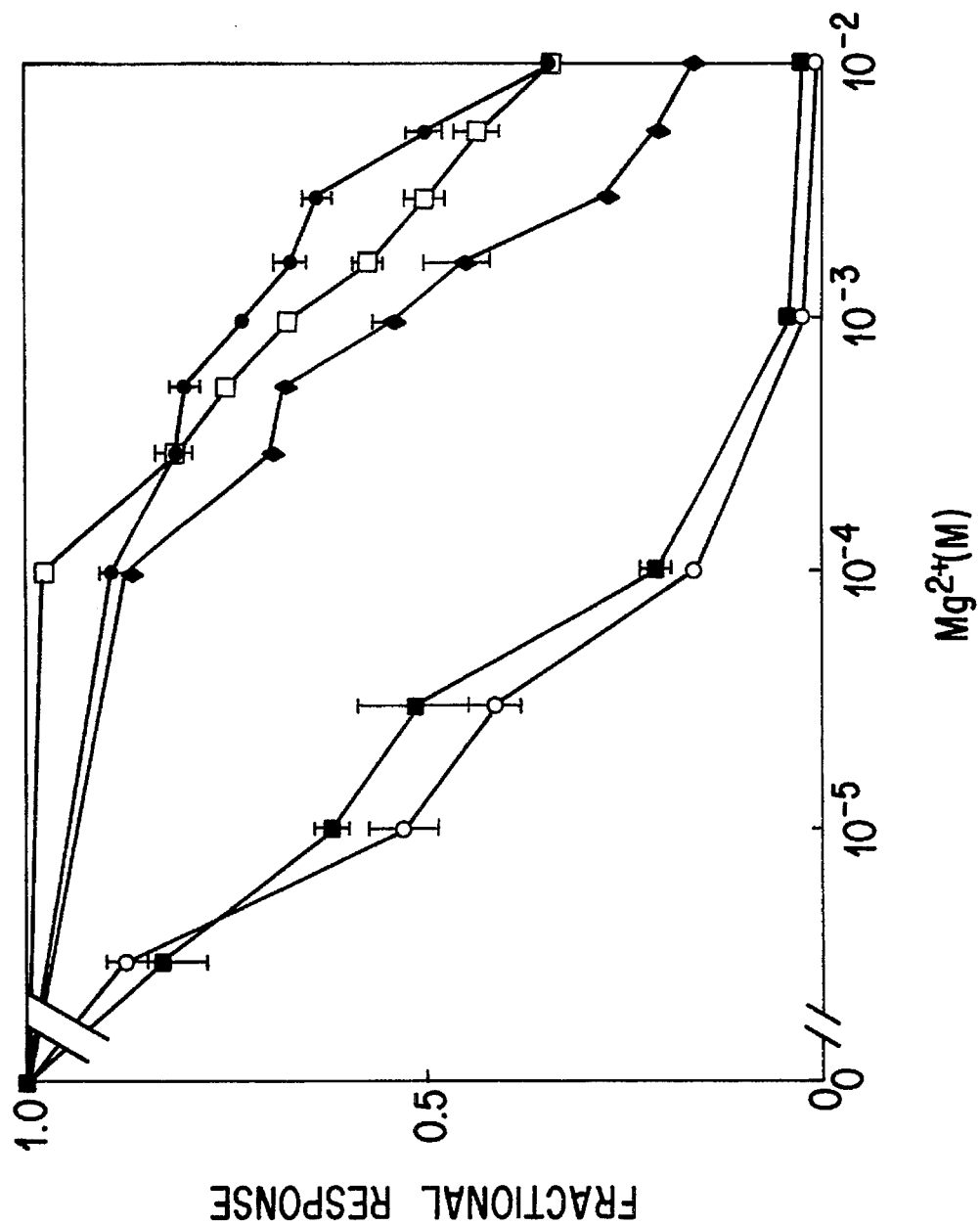
FIG. 6 shows the effects of $Mg^{2+}$ concentrations on the response at −70 mV membrane potential. In the figure, ○, ●, ◆, □ and ■ represent an ε2/ζ1 NMDA receptor channel, an ε2/ζ1-N598Q NMDA receptor channel, an ε2-N589Q/ζ1 NMDA receptor channel, an ε2-N589Q/ζ1-N598Q NMDA receptor channel and an ε2/ζ1-ZAZ (a mutant glutamate receptor shown in Sequence ID No. 10 of the sequence table) NMDA receptor channel, respectively.

In order to minimize effects of a secondary activated $Ca^{2+}$ dependent Cl- current, influences of these modified products on $Mg^{2+}$ inhibition were measured more quantitatively in a $Ba^{2+}$ Ringer's solution. FIGS. 5(a) to 5(d) each represent current-voltage curves of the wild type and modified heteromeric channels in the presence of 1 mM $Mg^{2+}$ (●) and in the absence thereof (○). As observed in the case of the NMDA type receptor channel, $Mg^{2+}$ inhibited a current response to the wild type $\epsilon2/\zeta1$ channel depending on voltage (FIG. 5(a). Sensitivity of the heteromeric channel to $Mg^{2+}$ was decreased greatly by modification of an asparagine residue(s) of one or both of the subunits, and the modified channel retained activity even at −100 mV membrane potential (FIGS. 5(b) to 5(d)). Inhibition degrees at various $Mg^{2+}$ concentrations were compared at −70 mV membrane potential (FIG. 6). Activities of the wild type $\epsilon2/\zeta1$ channel and the $\epsilon2/\zeta1$-ZAZ channel were decreased by 50% by not more than 20 μM $Mg^{2+}$ and suppressed almost completely by not more than 1 mM $Mg^{2+}$ which is a physiological concentration. On the other hand, about 100-fold concentration of $Mg^{2+}$ was required to depress the modified $\epsilon2/\zeta1$-N598Q, $\epsilon2$-N589Q/$\zeta1$ and $\epsilon2$-589Q/$\zeta1$-N598Q channels.

Figure 7:
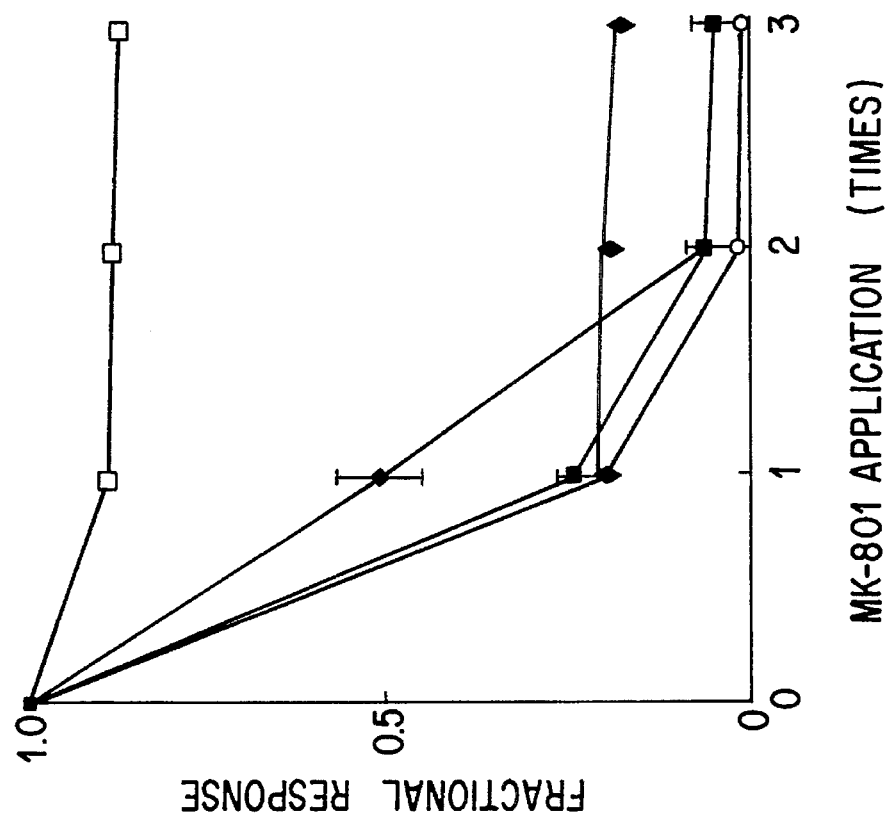
FIG. 7 shows suppression after repetitive application of 1 μM (+)-MK 801. In the figure, ○, ●, ◆, □ and ■ represent a ε2/ζ1 NMDA receptor channel, an ε2/ζ1-N598Q MNDA receptor channel, an ε2-N589Q/ζ1 NMDA receptor channel, ε2-N589Q/ζ1-N598Q NMDA receptor channel and an ε2/ζ1-ZAZ NMDA receptor channel, respectively.

By administering 1 μM (+)-MK-801 which is an open channel blocker of the NMDA type receptor channel repeatedly, the wild type $\epsilon2/\zeta1$ channel was suppressed almost completely (FIG. 7). Similarly, activities of the modified $\epsilon2/\zeta1$-N598Q and $\epsilon2$-N589Q/$\zeta1$ channels were strongly inhibited by continuous application of (+)-MK-801. On the other hand, the modified $\epsilon2$-N589Q/$\zeta1$-N598Q channel retained high activities even after (+)-MK-801 was applied three times repeatedly.

Figure 8:
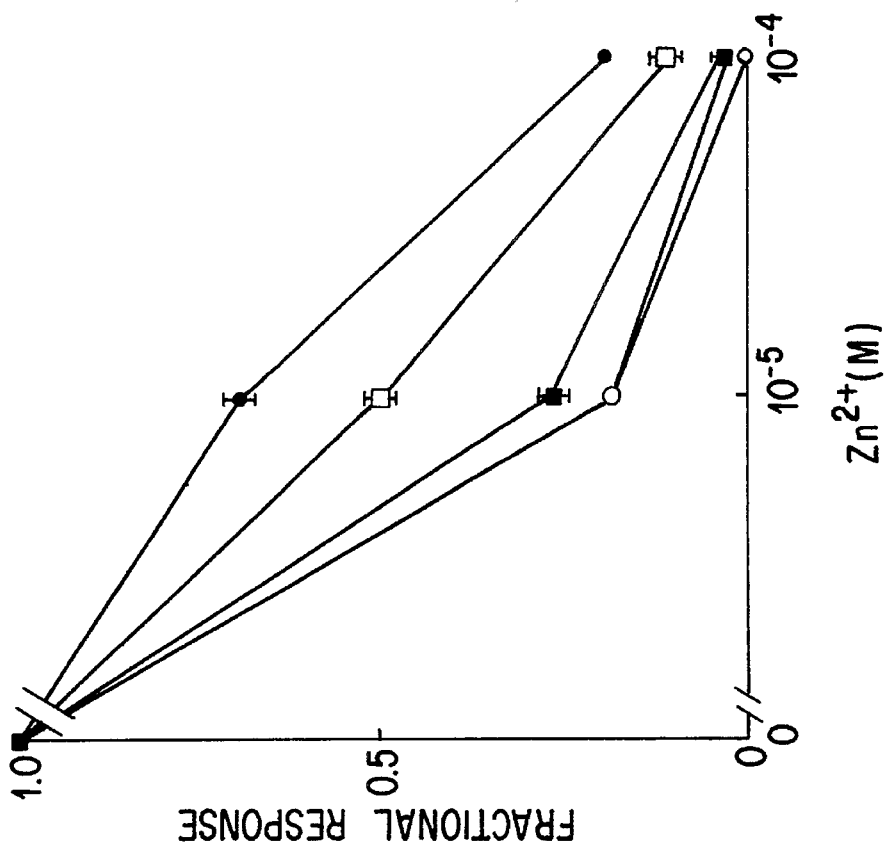
FIG. 8 shows the sensitivity to various concentrations of $Zn^{2+}$. In the figure, ○, ●, ◆, □ and ■ represent an ε2/ζ1 NMDA receptor channel, an ε2/ζ1-N598Q NMDA receptor channel, an ε2-N589Q/ζ1 NMDA receptor channel, an ε2-N589Q/ζ1-N598Q NMDA receptor channel and an ε2/ζ1-ZAZ NMDA receptor channel, respectively.

Effect of $Zn^{2+}$ which had been reported to induce non-competitive inhibition to the NMDA type receptor not depending on voltage was examined. Sensitivity of the heteromeric channel to 10 μM $Zn^{2+}$ was decreased a little by modification. However, the modified channel was strongly inhibited by 100 μM $Zn^{2+}$ (FIG. 8).

These results suggested that the NMDA type receptor channels having different functions were formed by modification of the subunits.

The NMDA type glutamate receptor genes of the present invention are not only useful for clarifying nervous information transmission at a synapse, appearance of synapse plasticity which is basically required for memory and learning and neuronal cell death caused by a disease such as cerebral ischemia and epilepsy and understanding a transmission mechanism of nervous information in a center, a cerebral structure of higher order and a disease of the brain, but are also useful for therapy of genetic diseases and preparation of novel pharmaceuticals (e.g. screening of an agonist or an antagonist).

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
( A ) LENGTH: 1464 amino acids
( B ) TYPE: amino acid
( C ) STRANDEDNESS: single strand
( D ) TOPOLOGY: linear ( i i ) MOLECULE TYPE: protein ( v i ) ORIGINAL SOURCE:
( A ) ORGANISM: mouse
( F ) TISSUE TYPE: cerebellum ( x ) PUBLICATION INFORMATION:
( A ) AUTHORS: Masayoshi MISHINA
( B ) TITLE: NOVEL PROTEINS AND GENES CODING THE SAME
( K ) RELEVANT RESIDUES IN SEQ ID NO:1: FROM 1 to 1464

( x i ) SEQUENCE DESCRIPTION: SEQ ID NO:1:

| Met 1 | Gly | Arg | Leu | Gly 5 | Tyr | Trp | Thr | Leu |
| --- | --- | --- | --- | --- | --- | --- | --- | --- |
| Leu 10 | Val | Leu | Pro | Ala | Leu 15 | Leu | Val | Trp |
| His | Gly 20 | Pro | Ala | Gln | Asn | Ala 25 | Ala | Ala |
| Glu | Lys | Gly 30 | Thr | Pro | Ala | Leu | Asn 35 | Ile |
| Ala | Val | Leu | Leu | Gly | His | Ser | His | Asp |

|     |     |     | 40  |     |     | 45  |     |
| --- | --- | --- | --- | --- | --- | --- | --- |
| Val | Thr | Glu | Arg | Glu | Leu | Arg | Asn | Leu |
|     |     |     |     | 50  |     |     |     |     |
| Trp | Gly | Pro | Glu | Gln | Ala | Thr | Gly | Leu |
| 55  |     |     |     |     | 60  |     |     |     |
| Pro | Leu | Asp | Val | Asn | Val | Val | Ala | Leu |
|     | 65  |     |     |     |     | 70  |     |     |
| Leu | Met | Asn | Arg | Thr | Asp | Pro | Lys | Ser |
|     |     | 75  |     |     |     |     | 80  |     |
| Leu | Ile | Thr | His | Val | Cys | Asp | Leu | Met |
|     |     |     | 85  |     |     |     |     | 90  |
| Ser | Gly | Ala | Arg | Ile | His | Gly | Leu | Val |
|     |     |     |     | 95  |     |     |     |     |
| Phe | Gly | Asp | Asp | Thr | Asp | Gln | Glu | Ala |
| 100 |     |     |     |     | 105 |     |     |     |
| Val | Ala | Gln | Met | Leu | Asp | Phe | Ile | Ser |
|     | 110 |     |     |     |     | 115 |     |     |
| Ser | Gln | Thr | Phe | Ile | Pro | Ile | Leu | Gly |
|     |     | 120 |     |     |     |     | 125 |     |
| Ile | His | Gly | Gly | Ala | Ser | Met | Ile | Met |
|     |     |     | 130 |     |     |     |     | 135 |
| Ala | Asp | Lys | Asp | Pro | Thr | Ser | Thr | Phe |
|     |     |     |     | 140 |     |     |     |     |
| Phe | Gln | Phe | Gly | Ala | Ser | Ile | Gln | Gln |
| 145 |     |     |     |     | 150 |     |     |     |
| Gln | Ala | Thr | Val | Met | Leu | Lys | Ile | Met |
|     | 155 |     |     |     |     | 160 |     |     |
| Gln | Asp | Tyr | Asp | Trp | His | Val | Phe | Ser |
|     |     | 165 |     |     |     |     | 170 |     |
| Leu | Val | Thr | Thr | Ile | Phe | Pro | Gly | Tyr |
|     |     |     | 175 |     |     |     |     | 180 |
| Arg | Asp | Phe | Ile | Ser | Phe | Ile | Lys | Thr |
|     |     |     |     | 185 |     |     |     |     |
| Thr | Val | Asp | Asn | Ser | Phe | Val | Gly | Trp |
| 190 |     |     |     |     | 195 |     |     |     |
| Asp | Met | Gln | Asn | Val | Ile | Thr | Leu | Asp |
|     | 200 |     |     |     |     | 205 |     |     |
| Thr | Ser | Phe | Glu | Asp | Ala | Lys | Thr | Gln |
|     |     | 210 |     |     |     |     | 215 |     |
| Val | Gln | Leu | Lys | Lys | Ile | His | Ser | Ser |
|     |     |     | 220 |     |     |     |     | 225 |
| Val | Ile | Leu | Leu | Tyr | Cys | Ser | Lys | Asp |
|     |     |     |     | 230 |     |     |     |     |
| Glu | Ala | Val | Leu | Ile | Leu | Ser | Glu | Ala |
| 235 |     |     |     |     | 240 |     |     |     |
| Arg | Ser | Leu | Gly | Leu | Thr | Gly | Tyr | Asp |
|     | 245 |     |     |     |     | 250 |     |     |
| Phe | Phe | Trp | Ile | Val | Pro | Ser | Leu | Val |
|     |     | 255 |     |     |     |     | 260 |     |
| Ser | Gly | Asn | Thr | Glu | Leu | Ile | Pro | Lys |
|     |     |     | 265 |     |     |     |     | 270 |
| Glu | Phe | Pro | Ser | Gly | Leu | Ile | Ser | Val |
|     |     |     |     | 275 |     |     |     |     |

| Ser 280 | Tyr | Asp | Asp | Trp 285 | Asp | Tyr | Ser | Leu |
|---|---|---|---|---|---|---|---|---|
| Glu | Ala 290 | Arg | Val | Arg | Asp | Gly 295 | Leu | Gly |
| Ile | Leu | Thr 300 | Thr | Ala | Ala | Ser | Ser 305 | Met |
| Leu | Glu | Lys | Phe 310 | Ser | Tyr | Ile | Pro | Glu 315 |
| Ala | Lys | Ala | Ser | Cys 320 | Tyr | Gly | Gln | Thr |
| Glu 325 | Lys | Pro | Glu | Thr | Pro 330 | Leu | His | Thr |
| Leu | His 335 | Gln | Phe | Met | Val | Asn 340 | Val | Thr |
| Trp | Asp | Gly 345 | Lys | Asp | Leu | Ser | Phe 350 | Thr |
| Glu | Glu | Gly | Tyr 355 | Gln | Val | His | Pro | Arg 360 |
| Leu | Val | Val | Ile | Val 365 | Leu | Asn | Lys | Asp |
| Arg 370 | Glu | Trp | Glu | Lys | Val 375 | Gly | Lys | Trp |
| Glu | Asn 380 | Gln | Thr | Leu | Arg | Leu 385 | Arg | His |
| Ala | Val | Trp 390 | Pro | Arg | Tyr | Lys | Ser 395 | Phe |
| Ser | Asp | Cys | Glu 400 | Pro | Asp | Asp | Asn | His 405 |
| Leu | Ser | Ile | Val | Thr 410 | Leu | Glu | Glu | Ala |
| Pro 415 | Phe | Val | Ile | Val | Glu 420 | Asp | Ile | Asp |
| Pro | Leu 425 | Thr | Glu | Thr | Cys | Val 430 | Arg | Asn |
| Thr | Val | Pro 435 | Cys | Arg | Lys | Phe | Val 440 | Lys |
| Ile | Asn | Asn | Ser 445 | Thr | Asn | Glu | Gly | Met 450 |
| Asn | Val | Lys | Lys | Cys 455 | Cys | Lys | Gly | Phe |
| Cys 460 | Ile | Asp | Ile | Leu | Lys 465 | Lys | Leu | Ser |
| Arg | Thr 470 | Val | Lys | Phe | Thr | Tyr 475 | Asp | Leu |
| Tyr | Leu | Val 480 | Thr | Asn | Gly | Lys | His 485 | Gly |
| Lys | Lys | Val | Asn 490 | Asn | Val | Trp | Asn | Gly 495 |
| Met | Ile | Gly | Glu | Val 500 | Val | Tyr | Gln | Arg |
| Ala 505 | Val | Met | Ala | Val | Gly 510 | Ser | Leu | Thr |
| Ile | Asn 515 | Glu | Glu | Arg | Ser | Glu 520 | Val | Val |

| | | | | | | | |
|---|---|---|---|---|---|---|---|
| Asp | Phe | Ser 525 | Val | Pro | Phe | Val 530 | Thr |
| Gly | Ile | Ser | Val 535 | Met | Val | Ser | Arg | Ser 540 |
| Asn | Gly | Thr | Val | Ser 545 | Pro | Ser | Ala | Phe |
| Leu 550 | Glu | Pro | Phe | Ser | Ala 555 | Ser | Val | Trp |
| Val | Met 560 | Met | Phe | Val | Met | Leu 565 | Leu | Ile |
| Val | Ser | Ala 570 | Ile | Ala | Val | Phe | Val 575 | Phe |
| Glu | Tyr | Phe | Ser 580 | Pro | Val | Gly | Tyr | Asn 585 |
| Arg | Asn | Leu | Ala | Lys 590 | Gly | Lys | Ala | Pro |
| His 595 | Gly | Pro | Ser | Phe | Thr 600 | Ile | Gly | Lys |
| Ala | Ile 605 | Trp | Leu | Leu | Trp | Gly 610 | Leu | Val |
| Phe | Asn | Asn 615 | Ser | Val | Pro | Val | Gln 620 | Asn |
| Pro | Lys | Gly | Thr 625 | Thr | Ser | Lys | Ile | Met 630 |
| Val | Ser | Val | Trp | Ala 635 | Phe | Phe | Ala | Val |
| Ile 640 | Phe | Leu | Ala | Ser | Tyr 645 | Thr | Ala | Asn |
| Leu | Ala 650 | Ala | Phe | Met | Ile | Gln 655 | Glu | Glu |
| Phe | Val | Asp 660 | Gln | Val | Thr | Gly | Leu 665 | Ser |
| Asp | Lys | Lys | Phe 670 | Gln | Arg | Pro | His | Asp 675 |
| Tyr | Ser | Pro | Pro | Phe 680 | Arg | Phe | Gly | Thr |
| Val 685 | Pro | Asn | Gly | Ser | Thr 690 | Glu | Arg | Asn |
| Ile | Arg 695 | Asn | Asn | Tyr | Pro | Tyr 700 | Met | His |
| Gln | Tyr | Met 705 | Thr | Lys | Phe | Asn | Gln 710 | Arg |
| Gly | Val | Glu | Asp 715 | Ala | Leu | Val | Ser | Leu 720 |
| Lys | Thr | Gly | Lys | Leu 725 | Asp | Ala | Phe | Ile |
| Tyr 730 | Asp | Ala | Ala | Val | Leu 735 | Asn | Tyr | Lys |
| Ala | Gly 740 | Arg | Asp | Glu | Gly | Cys 745 | Lys | Leu |
| Val | Thr | Ile 750 | Gly | Ser | Gly | Tyr | Ile 755 | Phe |
| Ala | Thr | Thr | Gly | Tyr | Gly | Ile | Ala | Leu |

|       |       |       |       | 760   |       |       | 765   |
|-------|-------|-------|-------|-------|-------|-------|-------|
| Gln   | Lys   | Gly   | Ser   | Pro   | Trp   | Lys   | Arg   | Gln
|       |       |       |       | 770   |       |       |       |
| Ile   | Asp   | Leu   | Ala   | Leu   | Leu   | Gln   | Phe   | Val
| 775   |       |       |       |       | 780   |       |       |
| Gly   | Asp   | Gly   | Glu   | Met   | Glu   | Glu   | Leu   | Glu
|       | 785   |       |       |       |       | 790   |       |
| Thr   | Leu   | Trp   | Leu   | Thr   | Gly   | Ile   | Cys   | His
|       |       | 795   |       |       |       |       | 800   |
| Asn   | Glu   | Lys   | Asn   | Glu   | Val   | Met   | Ser   | Ser
|       |       |       | 805   |       |       |       |       | 810
| Gln   | Leu   | Asp   | Ile   | Asp   | Asn   | Met   | Ala   | Gly
|       |       |       |       | 815   |       |       |       |
| Val   | Phe   | Tyr   | Met   | Leu   | Ala   | Ala   | Ala   | Met
| 820   |       |       |       |       | 825   |       |       |
| Ala   | Leu   | Ser   | Leu   | Ile   | Thr   | Phe   | Ile   | Trp
|       | 830   |       |       |       |       | 835   |       |
| Glu   | His   | Leu   | Phe   | Tyr   | Trp   | Lys   | Leu   | Arg
|       |       | 840   |       |       |       |       | 845   |
| Phe   | Cys   | Phe   | Thr   | Gly   | Val   | Cys   | Ser   | Asp
|       |       |       | 850   |       |       |       |       | 855
| Arg   | Pro   | Gly   | Leu   | Leu   | Phe   | Ser   | Ile   | Ser
|       |       |       |       | 860   |       |       |       |
| Arg   | Gly   | Ile   | Tyr   | Ser   | Cys   | Ile   | His   | Gly
| 865   |       |       |       |       | 870   |       |       |
| Val   | His   | Ile   | Glu   | Glu   | Lys   | Lys   | Lys   | Ser
|       | 875   |       |       |       |       | 880   |       |
| Pro   | Asp   | Phe   | Asn   | Leu   | Thr   | Gly   | Ser   | Gln
|       |       | 885   |       |       |       |       | 890   |
| Ser   | Asn   | Met   | Leu   | Lys   | Leu   | Leu   | Arg   | Ser
|       |       |       | 895   |       |       |       |       | 900
| Ala   | Lys   | Asn   | Ile   | Ser   | Asn   | Met   | Ser   | Asn
|       |       |       |       | 905   |       |       |       |
| Met   | Asn   | Ser   | Ser   | Arg   | Met   | Asp   | Ser   | Pro
| 910   |       |       |       |       | 915   |       |       |
| Lys   | Arg   | Ala   | Ala   | Asp   | Phe   | Ile   | Gln   | Arg
|       | 920   |       |       |       |       | 925   |       |
| Gly   | Ser   | Leu   | Ile   | Val   | Asp   | Met   | Val   | Ser
|       |       | 930   |       |       |       |       | 935   |
| Asp   | Lys   | Gly   | Asn   | Leu   | Ile   | Tyr   | Ser   | Asp
|       |       |       | 940   |       |       |       |       | 945
| Asn   | Arg   | Ser   | Phe   | Gln   | Gly   | Lys   | Asp   | Ser
|       |       |       |       | 950   |       |       |       |
| Ile   | Phe   | Gly   | Glu   | Asn   | Met   | Asn   | Glu   | Leu
| 955   |       |       |       |       | 960   |       |       |
| Gln   | Thr   | Phe   | Val   | Ala   | Asn   | Arg   | His   | Lys
|       | 965   |       |       |       |       | 970   |       |
| Asp   | Ser   | Leu   | Ser   | Asn   | Tyr   | Val   | Phe   | Gln
|       |       | 975   |       |       |       |       | 980   |
| Gly   | Gln   | His   | Pro   | Leu   | Thr   | Leu   | Asn   | Glu
|       |       |       | 985   |       |       |       |       | 990
| Ser   | Asn   | Pro   | Asn   | Thr   | Val   | Glu   | Val   | Ala
|       |       |       |       | 995   |       |       |       |

| | | | | | | | | |
|---|---|---|---|---|---|---|---|---|
| Val 1000 | Ser | Thr | Glu | Ser | Lys 1005 | Gly | Asn | Ser |
| Arg | Pro 1010 | Arg | Gln | Leu | Trp | Lys 1015 | Lys | Ser |
| Met | Glu | Ser 1020 | Leu | Arg | Gln | Asp | Ser 1025 | Leu |
| Asn | Gln | Asn | Pro 1030 | Val | Ser | Gln | Arg | Asp 1035 |
| Glu | Lys | Thr | Ala | Glu 1040 | Asn | Arg | Thr | His |
| Ser 1045 | Leu | Lys | Ser | Pro | Arg 1050 | Tyr | Leu | Pro |
| Glu | Glu 1055 | Val | Ala | His | Ser | Asp 1060 | Ile | Ser |
| Glu | Thr | Ser 1065 | Ser | Arg | Ala | Thr | Cys 1070 | His |
| Arg | Glu | Pro | Asp 1075 | Asn | Asn | Lys | Asn | His 1080 |
| Lys | Thr | Lys | Asp | Asn 1085 | Phe | Lys | Arg | Ser |
| Met 1090 | Ala | Ser | Lys | Tyr | Pro 1095 | Lys | Asp | Cys |
| Ser | Glu 1100 | Val | Glu | Arg | Thr | Tyr 1105 | Val | Lys |
| Thr | Lys | Ala 1110 | Ser | Ser | Pro | Arg | Asp 1115 | Lys |
| Ile | Tyr | Thr | Ile 1120 | Asp | Gly | Glu | Lys | Glu 1125 |
| Pro | Ser | Phe | His | Leu 1130 | Asp | Pro | Pro | Gln |
| Phe 1135 | Ile | Glu | Asn | Ile | Val 1140 | Leu | Pro | Glu |
| Asn | Val 1145 | Asp | Phe | Pro | Asp | Thr 1150 | Tyr | Gln |
| Asp | His | Asn 1155 | Glu | Asn | Phe | Arg | Lys 1160 | Gly |
| Asp | Ser | Thr | Leu 1165 | Pro | Met | Asn | Arg | Asn 1170 |
| Pro | Leu | His | Asn | Glu 1175 | Asp | Gly | Leu | Pro |
| Asn 1180 | Asn | Asp | Gln | Tyr | Lys 1185 | Leu | Tyr | Ala |
| Lys | His 1190 | Phe | Thr | Leu | Lys | Asp 1195 | Lys | Gly |
| Ser | Pro | His 1200 | Ser | Glu | Gly | Ser | Asp 1205 | Arg |
| Tyr | Arg | Gln | Asn 1210 | Ser | Thr | His | Cys | Arg 1215 |
| Ser | Cys | Leu | Ser | Asn 1220 | Leu | Pro | Thr | Tyr |
| Ser 1225 | Gly | His | Phe | Thr | Met 1230 | Arg | Ser | Pro |
| Phe | Lys 1235 | Cys | Asp | Ala | Cys | Leu 1240 | Arg | Met |

| | | | | | | | |
|---|---|---|---|---|---|---|---|
| Gly | Asn | Leu 1245 | Tyr | Asp | Ile | Glu 1250 | Asp |
| Gln | Met | Leu | Gln 1255 | Glu | Thr | Gly | Asn Pro 1260 |
| Ala | Thr | Arg | Glu | Glu 1265 | Ala | Tyr | Gln Gln |
| Asp 1270 | Trp | Ser | Gln | Asn | Asn 1275 | Ala | Leu Gln |
| Phe | Gln 1280 | Lys | Asn | Lys | Leu | Lys 1285 | Ile Asn |
| Arg | Gln | His 1290 | Ser | Tyr | Asp | Asn | Ile 1295 Leu |
| Asp | Lys | Pro | Arg 1300 | Glu | Ile | Asp | Leu Ser 1305 |
| Arg | Pro | Ser | Arg | Ser 1310 | Ile | Ser | Leu Lys |
| Asp 1315 | Arg | Glu | Arg | Leu | Leu 1320 | Glu | Gly Asn |
| Leu | Tyr 1325 | Gly | Ser | Leu | Phe | Ser 1330 | Val Pro |
| Ser | Ser | Lys 1335 | Leu | Leu | Gly | Asn | Lys Ser 1340 |
| Ser | Leu | Phe | Pro 1345 | Gln | Gly | Leu | Glu Asp 1350 |
| Ser | Lys | Arg | Ser | Lys 1355 | Ser | Leu | Leu Pro |
| Asp 1360 | His | Thr | Ser | Asp | Asn 1365 | Pro | Phe Leu |
| His | Thr 1370 | Tyr | Gly | Asp | Asp | Gln 1375 | Arg Leu |
| Val | Ile | Gly 1380 | Arg | Cys | Pro | Ser | Asp 1385 Pro |
| Tyr | Lys | His | Ser 1390 | Leu | Pro | Ser | Gln Ala 1395 |
| Val | Asn | Asp | Ser | Tyr 1400 | Leu | Arg | Ser Ser |
| Leu 1405 | Arg | Ser | Thr | Ala | Ser 1410 | Tyr | Cys Ser |
| Arg | Asp 1415 | Ser | Arg | Gly | His | Ser 1420 | Asp Val |
| Tyr | Ile | Ser 1425 | Glu | His | Val | Met | Pro 1430 Tyr |
| Ala | Ala | Asn | Lys 1435 | Asn | Asn | Met | Tyr Ser 1440 |
| Thr | Pro | Arg | Val | Leu 1445 | Asn | Ser | Cys Ser |
| Asn 1450 | Arg | Arg | Val | Tyr | Lys 1455 | Lys | Met Pro |
| Ser | Ile 1460 | Glu | Ser | Asp | Val | | |

( 2 ) INFORMATION FOR SEQ ID NO: 2:

( i ) SEQUENCE CHARACTERISTICS:

(A) LENGTH: 1482 amino acids
(B) TYPE: amino acid
(C) STRANDEDNESS: single strand
(D) TOPOLOGY: linear (ii) MOLECULE TYPE: protein (vi) ORIGINAL SOURCE:
(A) ORGANISM: mouse
(F) TISSUE TYPE: brain (x) PUBLICATION INFORMATION:
(A) AUTHORS: Masayoshi MISHINA
(B) TITLE: NOVEL PROTEINS AND GENES CODING THE SAME
(K) RELEVANT RESIDUES IN SEQ ID NO:2: FROM 1 to 1482

(xi) SEQUENCE DESCRIPTION: SEQ ID NO:2:

| Met 1 | Lys | Pro | Ser | Ala 5 | Glu | Cys | Cys | Ser |
| Pro 10 | Lys | Phe | Trp | Leu 15 | Leu | Ala | Val |
| Leu | Ala 20 | Val | Ser | Gly | Ser | Lys 25 | Ala | Arg |
| Ser | Gln | Lys 30 | Ser | Ala | Pro | Ser | Ile 35 | Gly |
| Ile | Ala | Val | Ile 40 | Leu | Val | Gly | Thr | Ser 45 |
| Asp | Glu | Val | Ala | Ile 50 | Lys | Asp | Ala | His |
| Glu 55 | Lys | Asp | Asp | Phe | His 60 | His | Leu | Ser |
| Val | Val 65 | Pro | Arg | Val | Glu | Leu 70 | Val | Ala |
| Met | Asn | Glu 75 | Thr | Asp | Pro | Lys | Ser 80 | Ile |
| Ile | Thr | Arg | Ile 85 | Cys | Asp | Leu | Met | Ser 90 |
| Asp | Arg | Lys | Ile | Gln 95 | Gly | Val | Val | Leu |
| Ala 100 | Asp | Asp | Thr | Asp | Gln 105 | Glu | Ala | Ile |
| Ala | Gln 110 | Ile | Leu | Asp | Phe | Ile 115 | Ser | Ala |
| Gln | Thr | Leu 120 | Thr | Pro | Ile | Leu | Gly 125 | Ile |
| His | Gly | Gly | Ser 130 | Ser | Met | Ile | Met | Ala 135 |
| Asp | Lys | Asp | Glu | Ser 140 | Ser | Met | Phe | Phe |
| Gln 145 | Phe | Gly | Pro | Ser | Ile 150 | Glu | Gln | Gln |
| Ala | Ser 155 | Val | Met | Leu | Asn | Ile 160 | Met | Glu |
| Glu | Tyr | Asp 165 | Trp | Tyr | Ile | Phe | Ser 170 | Ile |
| Val | Thr | Thr | Tyr 175 | Phe | Pro | Gly | Tyr | Gln 180 |
| Asp | Phe | Val | Asn | Lys 185 | Ile | Arg | Ser | Thr |

| | | | | | | | |
|---|---|---|---|---|---|---|---|
| Ile 190 | Glu | Asn | Ser | Phe | Val 195 | Gly | Trp | Glu |
| Leu | Glu 200 | Val | Leu | Leu | Leu 205 | Asp | Met |
| Ser | Leu | Asp 210 | Asp | Gly | Asp | Ser | Lys 215 | Ile |
| Gln | Asn | Gln | Leu 220 | Lys | Lys | Leu | Gln | Ser 225 |
| Pro | Ile | Ile | Leu | Leu 230 | Tyr | Cys | Thr | Lys |
| Glu 235 | Glu | Ala | Thr | Tyr | Ile 240 | Phe | Glu | Val |
| Ala | Asn 245 | Ser | Val | Gly | Leu | Thr 250 | Gly | Tyr |
| Gly | Tyr | Thr 255 | Trp | Ile | Val | Pro | Ser 260 | Leu |
| Val | Ala | Gly | Asp 265 | Thr | Asp | Thr | Val | Pro 270 |
| Ser | Glu | Phe | Pro | Thr 275 | Gly | Leu | Ile | Ser |
| Val 280 | Ser | Tyr | Asp | Glu | Trp 285 | Asp | Tyr | Gly |
| Leu | Pro 290 | Ala | Arg | Val | Arg | Asp 295 | Gly | Ile |
| Ala | Ile | Ile 300 | Thr | Thr | Ala | Ala | Ser 305 | Asp |
| Met | Leu | Ser | Glu 310 | His | Ser | Phe | Ile | Pro 315 |
| Glu | Pro | Lys | Ser | Ser 320 | Cys | Tyr | Asn | Thr |
| His 325 | Glu | Lys | Arg | Ile | Tyr 330 | Gln | Ser | Asn |
| Met | Leu 335 | Asn | Arg | Tyr | Leu | Ile 340 | Asn | Val |
| Thr | Phe | Glu 345 | Gly | Arg | Asn | Leu | Ser 350 | Phe |
| Ser | Glu | Asp | Gly 355 | Tyr | Gln | Met | His | Pro 360 |
| Lys | Leu | Val | Ile | Ile 365 | Leu | Leu | Asn | Lys |
| Glu 370 | Arg | Lys | Trp | Glu | Arg 375 | Val | Gly | Lys |
| Trp | Lys 380 | Asp | Lys | Ser | Leu | Gln 385 | Met | Lys |
| Tyr | Tyr | Val 390 | Trp | Pro | Arg | Met | Cys 395 | Pro |
| Glu | Thr | Glu | Glu 400 | Gln | Glu | Asp | Asp | His 405 |
| Leu | Ser | Ile | Val | Thr 410 | Leu | Glu | Glu | Ala |
| Pro 415 | Phe | Val | Ile | Val | Glu 420 | Ser | Val | Asp |
| Pro | Leu | Ser | Gly | Thr | Cys | Met | Arg | Asn |

|     |     |     |     |     |     |     |     |
|-----|-----|-----|-----|-----|-----|-----|-----|
|     |     | 425 |     |     |     | 430 |     |
| Thr | Val | Pro 435 | Cys | Gln | Lys | Arg 440 | Ile |
| Ser | Glu | Asn | Lys 445 | Thr | Asp | Glu | Pro 450 |
| Gly | Tyr | Ile | Lys | Lys 455 | Cys | Cys | Lys | Gly |
| Phe 460 | Cys | Ile | Asp | Ile 465 | Leu | Lys | Lys | Ile |
| Ser | Lys 470 | Ser | Val | Lys | Phe 475 | Thr | Tyr | Asp |
| Leu | Tyr | Leu 480 | Val | Thr | Asn | Gly | Lys 485 | His |
| Gly | Lys | Lys | Ile 490 | Asn | Gly | Thr | Trp | Asn 495 |
| Gly | Met | Ile | Gly | Glu 500 | Val | Val | Met | Lys |
| Arg 505 | Ala | Tyr | Met | Ala | Val 510 | Gly | Ser | Leu |
| Thr | Ile 515 | Asn | Glu | Glu | Arg | Ser 520 | Glu | Val |
| Val | Asp | Phe 525 | Ser | Val | Pro | Phe | Ile 530 | Glu |
| Thr | Gly | Ile | Ser 535 | Val | Met | Val | Ser | Arg 540 |
| Ser | Asn | Gly | Thr | Val 545 | Ser | Pro | Ser | Ala |
| Phe 550 | Leu | Glu | Pro | Phe | Ser 555 | Ala | Asp | Val |
| Trp | Val 560 | Met | Met | Phe | Val | Met 565 | Leu | Leu |
| Ile | Val | Ser 570 | Ala | Val | Ala | Val | Phe 575 | Val |
| Phe | Glu | Tyr | Phe 580 | Ser | Pro | Val | Gly | Tyr 585 |
| Asn | Arg | Cys | Leu | Ala 590 | Asp | Gly | Arg | Glu |
| Pro 595 | Gly | Gly | Pro | Ser | Phe 600 | Thr | Ile | Gly |
| Lys | Ala 605 | Ile | Trp | Leu | Leu | Trp 610 | Gly | Leu |
| Val | Phe | Asn | Asn 615 | Ser | Val | Pro | Val 620 | Gln |
| Asn | Pro | Lys | Gly 625 | Thr | Thr | Ser | Lys | Ile 630 |
| Met | Val | Ser | Val | Trp 635 | Ala | Phe | Phe | Ala |
| Val 640 | Ile | Phe | Leu | Ala | Ser 645 | Tyr | Thr | Ala |
| Asn | Leu 650 | Ala | Ala | Phe | Met | Ile 655 | Gln | Glu |
| Glu | Tyr | Val 660 | Asp | Gln | Val | Ser | Gly 665 | Leu |

| | | | | | | | |
|---|---|---|---|---|---|---|---|
| Ser | Asp | Lys | Lys 670 | Phe | Gln | Arg | Pro Asn 675 |
| Asp | Phe | Ser | Pro 680 | Phe | Arg | Phe | Gly |
| Thr 685 | Val | Pro | Asn | Gly | Ser 690 | Thr | Glu Arg |
| Asn | Ile 695 | Arg | Asn | Asn | Tyr | Ala 700 | Glu Met |
| His | Ala | Tyr 705 | Met | Gly | Lys | Phe | Asn 710 Gln |
| Arg | Gly | Val | Asp 715 | Ala | Leu | Leu | Ser 720 |
| Leu | Lys | Thr | Gly | Lys 725 | Leu | Asp | Ala Phe |
| Ile 730 | Tyr | Asp | Ala | Ala | Val 735 | Leu | Asn Tyr |
| Met | Ala 740 | Gly | Arg | Asp | Glu | Gly 745 | Cys Lys |
| Leu | Val | Thr 750 | Ile | Gly | Ser | Gly | Lys 755 Val |
| Phe | Ala | Ser | Thr 760 | Gly | Tyr | Gly | Ile Ala 765 |
| Ile | Gln | Lys | Asp | Ser 770 | Gly | Trp | Lys Arg |
| Gln 775 | Val | Asp | Leu | Ala | Ile 780 | Leu | Gln Leu |
| Phe | Gly 785 | Asp | Gly | Glu | Met | Glu 790 | Glu Leu |
| Glu | Ala | Leu 795 | Trp | Leu | Thr | Gly | Ile 800 Cys |
| His | Asn | Glu | Lys 805 | Asn | Glu | Val | Met Ser 815 |
| Ser | Gln | Leu | Asp | Ile 820 | Asp | Asn | Met Ala |
| Gly | Val | Phe | Tyr | Met | Leu 825 | Gly | Ala Ala |
| Met | Ala 830 | Leu | Ser | Leu | Ile | Thr 835 | Phe Ile |
| Cys | Glu | His 840 | Leu | Phe | Tyr | Trp | Gln 845 Phe |
| Arg | His | Cys | Phe 850 | Met | Gly | Val | Cys Ser 855 |
| Gly | Lys | Pro | Gly | Met 860 | Val | Phe | Ser Ile |
| Ser 865 | Arg | Gly | Ile | Tyr | Ser 870 | Cys | Ile His |
| Gly | Val 875 | Ala | Ile | Glu | Glu | Arg 880 | Gln Ser |
| Val | Met | Asn 885 | Ser | Pro | Thr | Ala | Thr 890 Met |
| Asn | Asn | Thr | His 895 | Ser | Asn | Ile | Leu Arg 900 |
| Leu | Leu | Arg | Thr | Ala 905 | Lys | Asn | Met Ala |

| | | | | | | | |
|---|---|---|---|---|---|---|---|
| Asn 910 | Leu | Ser | Gly | Val | Asn 915 | Gly | Ser | Pro |
| Gln | Ser 920 | Ala | Leu | Asp | Phe | Ile 925 | Arg | Arg |
| Glu | Ser | Ser 930 | Val | Tyr | Asp | Ile | Ser 935 | Glu |
| His | Arg | Arg | Ser 940 | Phe | Thr | His | Ser | Asp 945 |
| Cys | Lys | Ser | Tyr | Asn 950 | Asn | Pro | Pro | Cys |
| Glu 955 | Glu | Asn | Leu | Phe | Ser 960 | Asp | Tyr | Ile |
| Ser | Glu 965 | Val | Glu | Arg | Thr | Phe 970 | Gly | Asn |
| Leu | Gln | Leu 975 | Lys | Asp | Ser | Asn | Val 980 | Tyr |
| Gln | Asp | His | Tyr 985 | His | His | His | His | Arg 990 |
| Pro | His | Ser | Ile | Gly 995 | Ser | Thr | Ser | Ser |
| Ile 1000 | Asp | Gly | Leu | Tyr | Asp 1005 | Cys | Asp | Asn |
| Pro | Pro 1010 | Phe | Thr | Thr | Gln | Pro 1015 | Arg | Ser |
| Ile | Ser | Lys 1020 | Lys | Pro | Leu | Asp | Ile 1025 | Gly |
| Leu | Pro | Ser | Ser 1030 | Lys | His | Ser | Gln | Leu 1035 |
| Ser | Asp | Leu | Tyr | Gly 1040 | Lys | Phe | Ser | Phe |
| Lys 1045 | Ser | Asp | Arg | Tyr | Ser 1050 | Gly | His | Asp |
| Asp | Leu 1055 | Ile | Arg | Ser | Asp | Val 1060 | Ser | Asp |
| Ile | Ser | Thr 1065 | His | Thr | Val | Thr | Tyr 1070 | Gly |
| Asn | Ile | Glu | Gly 1075 | Asn | Ala | Ala | Lys | Arg 1080 |
| Arg | Lys | Gln | Gln | Tyr 1085 | Lys | Asp | Ser | Leu |
| Lys 1090 | Lys | Arg | Pro | Ala | Ser 1095 | Ala | Lys | Ser |
| Arg | Arg 1100 | Glu | Phe | Asp | Glu | Ile 1105 | Glu | Leu |
| Ala | Tyr | Arg 1110 | Arg | Arg | Pro | Pro | Arg 1115 | Ser |
| Pro | Asp | His | Lys 1120 | Arg | Tyr | Phe | Arg | Asp 1125 |
| Lys | Glu | Gly | Leu | Arg 1139 | Asp | Phe | Tyr | Leu |
| Asp 1135 | Gln | Phe | Arg | Thr | Lys 1140 | Glu | Asn | Ser |
| Pro | His | Trp | Glu | His | Val | Asp | Leu | Thr |

|   |   |   |   |   |   |   |   |
|---|---|---|---|---|---|---|---|
|   | 1145 |   |   |   | 1150 |   |   |
| Asp | Ile | Tyr 1155 | Lys | Glu | Arg | Ser 1160 | Asp |
| Phe | Lys | Arg | Asp 1165 | Ser | Val | Ser | Gly | Gly 1170 |
| Gly | Pro | Cys | Thr | Asn 1175 | Arg | Ser | His | Leu |
| Lys 1180 | His | Gly | Thr | Gly | Asp 1185 | Lys | His | Gly |
| Val | Val 1190 | Gly | Gly | Val | Pro | Ala 1195 | Pro | Trp |
| Glu | Lys | Asn 1200 | Leu | Thr | Asn | Val | Asp 1205 | Trp |
| Glu | Asp | Arg | Ser 1210 | Gly | Gly | Asn | Phe | Cys 1215 |
| Arg | Ser | Cys | Pro | Ser 1220 | Lys | Leu | His | Asn |
| Tyr 1225 | Ser | Ser | Thr | Val | Ala 1230 | Gly | Gln | Asn |
| Ser | Gly 1235 | Arg | Gln | Ala | Cys | Ile 1240 | Arg | Cys |
| Glu | Ala | Cys 1245 | Lys | Lys | Ala | Gly | Asn 1250 | Leu |
| Tyr | Asp | Ile | Ser 1255 | Glu | Asp | Asn | Ser | Leu 1260 |
| Gln | Glu | Leu | Asp | Gln 1265 | Pro | Ala | Ala | Pro |
| Val 1270 | Ala | Val | Ser | Ser | Asn 1275 | Ala | Ser | Thr |
| Thr | Lys 1280 | Tyr | Pro | Gln | Ser | Pro 1285 | Thr | Asn |
| Ser | Lys | Ala 1290 | Gln | Lys | Lys | Asn | Arg 1295 | Asn |
| Lys | Leu | Arg | Arg 1300 | Gln | His | Ser | Tyr | Asp 1305 |
| Thr | Phe | Val | Asp | Leu 1310 | Gln | Lys | Glu | Glu |
| Ala 1315 | Ala | Leu | Ala | Pro | Arg 1320 | Ser | Val | Ser |
| Leu | Lys 1325 | Asp | Lys | Gly | Arg | Phe 1330 | Met | Asp |
| Gly | Ser | Pro 1335 | Tyr | Ala | His | Met | Phe 1340 | Glu |
| Met | Pro | Ala | Gly 1345 | Glu | Ser | Ser | Phe | Ala 1350 |
| Asn | Lys | Ser | Ser | Val 1355 | Thr | Thr | Ala | Gly |
| His 1360 | His | His | Asn | Asn | Pro 1365 | Gly | Ser | Gly |
| Tyr | Met 1370 | Leu | Ser | Lys | Ser | Leu 1375 | Tyr | Pro |
| Asp | Arg | Val 1380 | Thr | Gln | Asn | Pro | Phe 1385 | Ile |

| | | | | | | | |
|---|---|---|---|---|---|---|---|
| Pro | Thr | Phe | Gly 1390 | Asp | Asp | Gln | Cys | Leu 1395 |
| Leu | His | Gly | Ser | Lys 1400 | Ser | Tyr | Phe | Phe |
| Arg 1405 | Gln | Pro | Thr | Val | Ala 1410 | Gly | Ala | Ser |
| Lys | Thr 1415 | Arg | Pro | Asp | Phe | Arg 1420 | Ala | Leu |
| Val | Thr | Asn 1425 | Lys | Pro | Val | Val | Ser 1430 | Ala |
| Leu | His | Gly | Ala 1435 | Val | Pro | Gly | Arg | Phe 1440 |
| Gln | Lys | Asp | Ile | Cys 1445 | Ile | Gly | Asn | Gln |
| Ser 1450 | Asn | Pro | Cys | Val | Pro 1455 | Asn | Asn | Lys |
| Asn | Pro 1460 | Arg | Ala | Phe | Asn | Gly 1465 | Ser | Ser |
| Asn | Gly | His 1470 | Val | Tyr | Glu | Lys | Leu 1475 | Ser |
| Ser | Ile | Glu | Ser 1480 | Asp | Val | | | |

(2) INFORMATION FOR SEQ ID NO: 3:

(i) SEQUENCE CHARACTERISTICS:
        (A) LENGTH: 1239 amino acids
        (B) TYPE: amino acid
        (C) STRANDEDNESS: single strand
        (D) TOPOLOGY: linear (ii) MOLECULE TYPE: protein (vi) ORIGINAL SOURCE:
        (A) ORGANISM: mouse
        (F) TISSUE TYPE: brain (x) PUBLICATION INFORMATION:
        (A) AUTHORS: Masayoshi MISHINA
        (B) TITLE: NOVEL PROTEINS AND GENES CODING THE SAME
        (K) RELEVANT RESIDUES IN SEQ ID NO:3: FROM 1 to 1239

(xi) SEQUENCE DESCRIPTION: SEQ ID NO:3:

| | | | | | | | |
|---|---|---|---|---|---|---|---|
| Met 1 | Gly | Gly | Ala | Leu 5 | Gly | Pro | Ala | Leu |
| Leu 10 | Leu | Thr | Ser | Leu | Leu 15 | Gly | Ala | Trp |
| Ala | Gly 20 | Leu | Gly | Ala | Gly | Gln 25 | Gly | Glu |
| Gln | Ala | Val 30 | Thr | Val | Ala | Val | Val 35 | Phe |
| Gly | Ser | Ser | Gly 40 | Pro | Leu | Gln | Ala | Gln 45 |
| Ala | Arg | Thr | Arg | Leu 50 | Thr | Pro | Gln | Asn |
| Phe 55 | Leu | Asp | Leu | Pro | Leu 60 | Glu | Ile | Gln |
| Pro | Leu 65 | Thr | Ile | Gly | Val | Asn 70 | Asn | Thr |
| Asn | Pro | Ser | Ser | Ile | Leu | Thr | Gln | Ile |

|     |     |     |     |     |     |     |     |     |
|---|---|---|---|---|---|---|---|---|
|     |     |     | 75  |     |     |     | 80  |     |
| Cys | Gly | Leu | Leu<br>85 | Gly | Ala | Ala | Arg | Val<br>90 |
| His | Gly | Ile | Val | Phe<br>95 | Glu | Asp | Asn | Val |
| Asp<br>100 | Thr | Glu | Ala | Val | Ala<br>105 | Gln | Leu | Leu |
| Asp | Phe<br>110 | Val | Ser | Ser | Gln | Thr<br>115 | His | Val |
| Pro | Ile | Leu<br>120 | Ser | Ile | Ser | Gly | Gly<br>125 | Ser |
| Ala | Val | Val | Leu<br>130 | Thr | Pro | Lys | Glu | Pro<br>135 |
| Gly | Ser | Ala | Phe | Leu<br>140 | Gln | Leu | Gly | Val |
| Ser<br>145 | Leu | Glu | Gln | Gln | Leu<br>150 | Gln | Val | Leu |
| Phe | Lys<br>155 | Val | Leu | Glu | Glu | Tyr<br>160 | Asp | Trp |
| Ser | Ala | Phe<br>165 | Ala | Val | Ile | Thr | Ser<br>170 | Leu |
| His | Pro | Gly | His<br>175 | Ala | Leu | Phe | Leu | Glu<br>180 |
| Gly | Val | Arg | Ala | Val<br>185 | Ala | Asp | Ala | Ser |
| Tyr<br>190 | Leu | Ser | Trp | Arg | Leu<br>195 | Leu | Asp | Val |
| Leu | Thr<br>200 | Leu | Glu | Leu | Gly | Pro<br>205 | Gly | Gly |
| Pro | Arg | Ala<br>210 | Arg | Thr | Gln | Arg | Leu<br>215 | Leu |
| Arg | Gln | Val | Asp<br>220 | Ala | Pro | Val | Leu | Val<br>225 |
| Ala | Tyr | Cys | Ser | Arg<br>230 | Glu | Glu | Ala | Glu |
| Val<br>235 | Leu | Phe | Ala | Glu | Ala<br>240 | Ala | Gln | Ala |
| Gly | Leu<br>245 | Val | Gly | Pro | Gly | His<br>250 | Val | Trp |
| Leu | Val | Pro<br>255 | Asn | Leu | Ala | Leu | Gly<br>260 | Ser |
| Thr | Asp | Ala | Pro<br>265 | Pro | Ala | Ala | Phe | Pro<br>270 |
| Val | Gly | Leu | Ile | Ser<br>275 | Val | Val | Thr | Glu |
| Ser<br>280 | Trp | Arg | Leu | Ser | Leu<br>285 | Arg | Gln | Lys |
| Val | Arg<br>290 | Asp | Gly | Val | Ala | Ile<br>295 | Leu | Ala |
| Leu | Gly | Ala<br>300 | His | Ser | Tyr | Arg | Arg<br>305 | Gln |
| Tyr | Gly | Thr | Leu<br>310 | Pro | Ala | Pro | Ala | Gly<br>315 |

| Asp | Cys | Arg | Ser | His 320 | Pro | Gly | Pro | Val |
|---|---|---|---|---|---|---|---|---|
| Ser 325 | Pro | Ala | Arg | Glu | Ala 330 | Phe | Tyr | Arg |
| His | Leu 335 | Leu | Asn | Val | Thr | Trp 340 | Glu | Gly |
| Arg | Asp | Phe 345 | Ser | Phe | Ser | Pro | Gly 350 | Gly |
| Tyr | Leu | Val | Gln 355 | Pro | Thr | Met | Val | Val 360 |
| Ile | Ala | Leu | Asn | Arg 365 | His | Arg | Leu | Trp |
| Glu 370 | Met | Val | Gly | Arg | Trp 375 | Asp | His | Gly |
| Val | Leu 380 | Tyr | Met | Lys | Tyr | Pro 385 | Val | Trp |
| Pro | Arg | Tyr 390 | Ser | Thr | Ser | Leu | Gln 395 | Pro |
| Val | Val | Asp | Ser 400 | Arg | His | Leu | Thr | Val 405 |
| Ala | Thr | Leu | Glu | Glu 410 | Arg | Pro | Phe | Val |
| Ile 415 | Val | Glu | Ser | Pro | Asp 420 | Pro | Gly | Thr |
| Gly | Gly 425 | Cys | Val | Pro | Asn | Thr 430 | Val | Pro |
| Cys | Arg | Arg 435 | Gln | Ser | Asn | His | Thr 440 | Phe |
| Ser | Ser | Gly | Asp 445 | Ile | Thr | Pro | Tyr | Thr 450 |
| Lys | Leu | Cys | Cys | Lys 455 | Gly | Phe | Cys | Ile |
| Asp 460 | Ile | Leu | Lys | Lys | Leu 465 | Ala | Lys | Val |
| Val | Lys 470 | Phe | Ser | Tyr | Asp | Leu 475 | Tyr | Leu |
| Val | Thr | Asn 480 | Gly | Lys | His | Gly | Lys 485 | Arg |
| Val | Arg | Gly | Val 490 | Trp | Asn | Gly | Met | Ile 495 |
| Gly | Glu | Val | Tyr | Tyr 500 | Lys | Arg | Ala | Asp |
| Met 505 | Ala | Ile | Gly | Ser | Leu 510 | Thr | Ile | Asn |
| Glu | Glu 515 | Arg | Ser | Glu | Ile | Ile 520 | Asp | Phe |
| Ser | Val | Pro 525 | Phe | Val | Glu | Thr | Gly 530 | Ile |
| Ser | Val | Met | Val 535 | Ala | Arg | Ser | Asn | Gly 540 |
| Thr | Val | Ser | Pro | Ser 545 | Ala | Phe | Leu | Glu |
| Pro 550 | Tyr | Ser | Pro | Ala | Val 555 | Trp | Val | Met |

| | | | | | | | |
|---|---|---|---|---|---|---|---|
| Met | Phe<br>560 | Val | Met | Cys | Leu | Thr<br>565 | Val | Val |
| Ala | Ile | Thr<br>570 | Val | Phe | Met | Phe<br>575 | Glu | Tyr |
| Phe | Ser | Pro | Val<br>580 | Ser | Tyr | Asn | Gln<br>585 | Asn |
| Leu | Thr | Lys | Gly | Lys<br>590 | Lys | Ser | Gly | Gly |
| Pro<br>595 | Ser | Phe | Thr | Ile | Gly<br>600 | Lys | Ser | Val |
| Trp | Leu<br>605 | Leu | Trp | Ala | Leu | Val<br>610 | Phe | Asn |
| Asn | Ser | Val<br>615 | Pro | Ile | Glu | Asn | Pro<br>620 | Arg |
| Gly | Thr | Thr | Ser | Lys<br>625 | Ile | Met | Val | Leu<br>630 |
| Val | Trp | Ala | Phe | Phe<br>635 | Ala | Val | Ile | Phe |
| Leu<br>640 | Ala | Ser | Tyr | Thr | Ala<br>645 | Asn | Leu | Ala |
| Ala | Phe<br>650 | Met | Ile | Gln | Glu<br>655 | Gln | Tyr | Ile |
| Asp | Thr | Val<br>660 | Ser | Gly | Leu | Ser | Asp<br>665 | Lys |
| Lys | Phe | Gln | Arg<br>670 | Pro | Gln | Asp | Gln | Tyr<br>675 |
| Pro | Pro | Phe | Arg | Phe<br>680 | Gly | Thr | Val | Pro |
| Asn<br>685 | Gly | Ser | Thr | Glu | Arg<br>690 | Asn | Ile | Arg |
| Ser | Asn<br>695 | Tyr | Arg | Asp | Met | His<br>700 | Thr | His |
| Met | Val | Lys<br>705 | Phe | Asn | Gln | Arg | Ser<br>710 | Val |
| Glu | Asp | Ala | Leu | Thr<br>715 | Ser | Leu | Lys | Met<br>720 |
| Gly | Lys | Leu | Asp | Ala<br>725 | Phe | Ile | Tyr | Asp |
| Ala<br>730 | Ala | Val | Leu | Asn | Tyr<br>735 | Met | Ala | Gly |
| Lys | Asp<br>740 | Glu | Gly | Cys | Lys | Leu<br>745 | Val | Thr |
| Ile | Gly | Ser<br>750 | Gly | Lys | Val | Phe | Ala<br>755 | Thr |
| Thr | Gly | Tyr | Gly<br>760 | Ile | Ala | Met | Gln | Lys<br>765 |
| Asp | Ser | His | Trp | Lys<br>770 | Arg | Ala | Ile | Asp |
| Leu<br>775 | Ala | Leu | Leu | Gln | Phe<br>780 | Leu | Gly | Asp |
| Gly | Glu<br>785 | Thr | Gln | Lys | Leu | Glu<br>790 | Thr | Val |
| Trp | Leu | Ser | Gly | Ile | Cys | His | Asn | Glu |

|     |     |     | 795 |     |     |     | 800 |
| --- | --- | --- | --- | --- | --- | --- | --- |
| Lys | Asn | Glu | Val | Met | Ser | Ser | Lys |
|     |     |     | 805 |     |     |     | 810 |
| Asp | Ile | Asp | Asn | Met | Ala | Gly | Val | Phe |
|     |     |     |     | 815 |     |     |     |
| Tyr | Met | Leu | Leu | Val | Ala | Met | Gly | Leu |
| 820 |     |     |     |     | 825 |     |     |     |
| Ala | Leu | Leu | Val | Phe | Ala | Trp | Glu | His |
|     | 830 |     |     |     |     | 835 |     |     |
| Leu | Val | Tyr | Trp | Lys | Leu | Arg | His | Ser |
|     |     | 840 |     |     |     |     | 845 |     |
| Val | Pro | Ser | Ser | Ser | Gln | Leu | Asp | Phe |
|     |     |     | 850 |     |     |     |     | 855 |
| Leu | Leu | Ala | Phe | Ser | Arg | Gly | Ile | Tyr |
|     |     |     |     | 860 |     |     |     |     |
| Ser | Cys | Phe | Asn | Gly | Val | Gln | Ser | Leu |
| 865 |     |     |     |     | 870 |     |     |     |
| Pro | Ser | Pro | Ala | Arg | Pro | Pro | Ser | Pro |
|     | 875 |     |     |     |     | 880 |     |     |
| Asp | Leu | Thr | Ala | Gly | Ser | Ala | Gln | Ala |
|     |     | 885 |     |     |     |     | 890 |     |
| Asn | Val | Leu | Lys | Met | Leu | Gln | Ala | Ala |
|     |     |     | 895 |     |     |     |     | 900 |
| Arg | Asp | Met | Val | Ser | Thr | Ala | Asp | Val |
|     |     |     |     | 905 |     |     |     |     |
| Ser | Gly | Ser | Leu | Asp | Arg | Ala | Thr | Arg |
| 910 |     |     |     |     | 915 |     |     |     |
| Thr | Ile | Glu | Asn | Trp | Gly | Asn | Asn | Arg |
|     | 920 |     |     |     |     | 925 |     |     |
| Arg | Ala | Pro | Ala | Pro | Thr | Thr | Ser | Gly |
|     |     | 930 |     |     |     |     | 935 |     |
| Pro | Arg | Ser | Cys | Thr | Pro | Gly | Pro | Pro |
|     |     |     | 940 |     |     |     |     | 945 |
| Gly | Gln | Pro | Ser | Pro | Ser | Gly | Trp | Arg |
|     |     |     |     | 950 |     |     |     |     |
| Pro | Pro | Gly | Gly | Gly | Arg | Thr | Pro | Leu |
| 955 |     |     |     |     | 960 |     |     |     |
| Ala | Arg | Arg | Ala | Pro | Gln | Pro | Pro | Ala |
|     | 965 |     |     |     |     | 970 |     |     |
| Arg | Pro | Gly | Pro | Ala | Gln | Gly | Arg | Leu |
|     |     | 975 |     |     |     |     | 980 |     |
| Ser | Pro | Thr | Cys | Pro | Glu | His | Pro | Ala |
|     |     |     | 985 |     |     |     |     | 990 |
| Gly | Thr | Leu | Gly | Met | Arg | Gly | Gly | Gln |
|     |     |     |     | 995 |     |     |     |     |
| Cys | Glu | Ser | Gly | Ile | Arg | Asp | Arg | Thr |
| 1000 |     |     |     |     | 1005 |     |     |     |
| Ser | Arg | Pro | Pro | Glu | Arg | Arg | Ala | Leu |
|     | 1010 |     |     |     |     | 1015 |     |     |
| Pro | Glu | Arg | Ser | Leu | Leu | His | Ala | His |
|     |     | 1020 |     |     |     |     | 1025 |     |
| Cys | His | Tyr | Ser | Ser | Phe | Pro | Arg | Ala |
|     |     |     | 1030 |     |     |     |     | 1035 |

```
Glu  Arg  Ser  Gly  Arg       Pro  Phe  Leu  Pro
                    1040

Leu  Phe  Pro  Glu  Pro       Pro  Glu  Pro  Asp
1045                1050

Asp  Leu  Pro  Leu  Leu       Gly  Pro  Glu  Gln
     1055                          1060

Leu  Ala  Arg  Arg  Glu       Ala  Leu  Leu  Arg
          1065                               1070

Ala  Ala  Trp  Ala  Arg       Gly  Pro  Arg  Pro
               1075                          1080

Arg  His  Ala  Ser  Leu       Pro  Ser  Ser  Val
                    1085

Ala  Glu  Ala  Phe  Thr       Arg  Ser  Asn  Pro
1090                               1095

Leu  Pro  Ala  Arg  Cys       Thr  Gly  His  Ala
     1100                          1105

Cys  Ala  Cys  Pro  Cys       Pro  Gln  Ser  Arg
               1110                          1115

Pro  Ser  Cys  Arg  His       Val  Ala  Gln  Thr
               1120                          1125

Gln  Ser  Leu  Arg  Leu       Pro  Ser  Tyr  Arg
                    1130

Glu  Ala  Cys  Val  Glu       Gly  Val  Pro  Ala
1135                               1140

Gly  Val  Ala  Ala  Thr       Trp  Gln  Pro  Arg
     1145                          1150

Gln  His  Val  Cys  Leu       His  Thr  His  Thr
          1155                               1160

His  Leu  Pro  Phe  Cys       Trp  Gly  Thr  Val
               1165                          1170

Cys  Arg  His  Pro  Pro       Pro  Cys  Ser  Ser
                    1175

His  Ser  Pro  Trp  Leu       Ile  Gly  Thr  Trp
1180                               1185

Glu  Pro  Pro  Ser  His       Arg  Gly  Arg  Thr
     1190                          1195

Leu  Gly  Leu  Gly  Thr       Gly  Tyr  Arg  Asp
          1200                               1205

Ser  Gly  Val  Leu  Glu       Glu  Val  Ser  Arg
               1210                          1215

Glu  Ala  Cys  Gly  Thr       Gln  Gly  Phe  Pro
                    1220

Arg  Ser  Cys  Thr  Trp       Arg  Arg  Ile  Ser
1225                               1230

Ser  Leu  Glu  Ser  Glu       Val
     1235
```

( 2 ) INFORMATION FOR SEQ ID NO: 4:

( i ) SEQUENCE CHARACTERISTICS:
        ( A ) LENGTH: 1323 amino acids
        ( B ) TYPE: amino acid
        ( C ) STRANDEDNESS: single strand
        ( D ) TOPOLOGY: linear ( i i ) MOLECULE TYPE: protein (vi) ORIGINAL SOURCE:
  (A) ORGANISM: mouse
  (F) TISSUE TYPE: brain (x) PUBLICATION INFORMATION:
  (A) AUTHORS: Masayoshi MISHINA
  (B) TITLE: NOVEL PROTEINS AND GENES CODING THE SAME
  (K) RELEVANT RESIDUES IN SEQ ID NO:4: FROM 1 to 1323

(xi) SEQUENCE DESCRIPTION: SEQ ID NO:4:

| Met | Arg | Gly | Ala | Gly | Gly | Pro | Arg | Gly | Pro | Arg | Gly | Pro | Ala | Lys | Met |
|---|---|---|---|---|---|---|---|---|---|---|---|---|---|---|---|
| 1 | | | | 5 | | | | | 10 | | | | | 15 | |
| Leu | Leu | Leu | Leu | Ala | Leu | Ala | Cys | Ala | Ser | Pro | Phe | Pro | Glu | Glu | Val |
| | | | 20 | | | | 25 | | | | | 30 | | | |
| Pro | Gly | Pro | Gly | Ala | Ala | Gly | Gly | Thr | Gly | Gly | Ala | Arg | Pro | Leu | |
| | | 35 | | | | 40 | | | | | 45 | | | | |
| Asn | Val | Ala | Leu | Val | Phe | Ser | Gly | Pro | Ala | Tyr | Ala | Ala | Glu | Ala | Ala |
| | 50 | | | | 55 | | | | | 60 | | | | | |
| Arg | Leu | Gly | Pro | Ala | Val | Ala | Ala | Val | Arg | Ser | Pro | Gly | Leu | Asp | |
| 65 | | | | 70 | | | | | 75 | | | | | 80 | |
| Val | Arg | Pro | Val | Ala | Leu | Val | Leu | Asn | Gly | Ser | Asp | Pro | Arg | Ser | Leu |
| | | | | 85 | | | | | 90 | | | | | 95 | |
| Val | Leu | Gln | Leu | Cys | Asp | Leu | Leu | Ser | Gly | Leu | Arg | Val | His | Gly | Val |
| | | | 100 | | | | | 105 | | | | | 110 | | |
| Val | Phe | Glu | Asp | Asp | Ser | Arg | Ala | Pro | Ala | Val | Ala | Pro | Ile | Leu | Asp |
| | | | 115 | | | | | 120 | | | | | 125 | | |
| Phe | Leu | Ser | Ala | Gln | Thr | Ser | Leu | Pro | Ile | Val | Ala | Val | His | Gly | Gly |
| | | 130 | | | | 135 | | | | | 140 | | | | |
| Ala | Ala | Leu | Val | Leu | Thr | Pro | Lys | Glu | Lys | Gly | Ser | Thr | Phe | Leu | Gln |
| 145 | | | | | 150 | | | | | 155 | | | | | 160 |
| Leu | Gly | Ser | Ser | Thr | Glu | Gln | Gln | Leu | Gln | Val | Ile | Phe | Glu | Val | Leu |
| | | | | 165 | | | | | 170 | | | | | 175 | |
| Glu | Glu | Tyr | Asp | Trp | Thr | Ser | Phe | Val | Ala | Val | Thr | Thr | Arg | Ala | Pro |
| | | | 180 | | | | | 185 | | | | | 190 | | |
| Gly | His | Arg | Ala | Phe | Leu | Ser | Tyr | Ile | Glu | Val | Leu | Thr | Asp | Gly | Ser |
| | | 195 | | | | | 200 | | | | | 205 | | | |
| Leu | Val | Gly | Trp | Glu | His | Arg | Gly | Ala | Leu | Thr | Leu | Asp | Pro | Gly | Ala |
| | 210 | | | | 215 | | | | | 220 | | | | | |
| Gly | Glu | Ala | Val | Leu | Gly | Ala | Gln | Leu | Arg | Ser | Val | Ser | Ala | Gln | Ile |
| 225 | | | | | 230 | | | | | 235 | | | | | 240 |
| Arg | Leu | Leu | Phe | Cys | Ala | Arg | Glu | Glu | Ala | Glu | Pro | Val | Phe | Arg | Ala |
| | | | | 245 | | | | | 250 | | | | | 255 | |
| Ala | Glu | Glu | Ala | Gly | Leu | Thr | Gly | Pro | Gly | Tyr | Val | Trp | Phe | Met | Val |
| | | | 260 | | | | | 265 | | | | | 270 | | |
| Gly | Pro | Gln | Leu | Ala | Gly | Gly | Gly | Ser | Gly | Val | Pro | Gly | Glu | Pro | |
| | | 275 | | | | 280 | | | | | 285 | | | | |
| Leu | Leu | Leu | Pro | Gly | Gly | Ala | Pro | Leu | Pro | Ala | Gly | Leu | Phe | Ala | Val |
| | | 290 | | | | 295 | | | | | 300 | | | | |
| Arg | Ser | Ala | Gly | Trp | Arg | Asp | Asp | Leu | Ala | Arg | Arg | Val | Ala | Ala | Gly |
| 305 | | | | | 310 | | | | | 315 | | | | | 320 |
| Val | Ala | Val | Val | Ala | Arg | Gly | Ala | Gln | Ala | Leu | Leu | Arg | Asp | Tyr | Gly |
| | | | | 325 | | | | | 330 | | | | | 335 | |
| Phe | Leu | Pro | Glu | Leu | Gly | His | Asp | Cys | Arg | Ala | Gln | Asn | Arg | Thr | His |
| | | | 340 | | | | | 345 | | | | | 350 | | |
| Arg | Gly | Glu | Ser | Leu | His | Arg | Tyr | Phe | Met | Asn | Ile | Thr | Trp | Asp | Asn |
| | | | 355 | | | | | 360 | | | | | 365 | | |

-continued

| | | | | | | | | | | | | | | |
|---|---|---|---|---|---|---|---|---|---|---|---|---|---|---|
| Arg | Asp | Tyr | Ser | Phe | Asn | Glu | Asp | Gly | Phe | Leu | Val | Asn | Pro | Ser | Leu |
| 370 | | | | | 375 | | | | 380 | | | | | | |
| Val | Val | Ile | Ser | Leu | Thr | Arg | Asp | Arg | Thr | Trp | Glu | Val | Val | Gly | Ser |
| 385 | | | | | 390 | | | | 395 | | | | | | 400 |
| Trp | Glu | Gln | Gln | Thr | Leu | Arg | Leu | Lys | Tyr | Pro | Leu | Trp | Ser | Arg | Tyr |
| | | | | 405 | | | | | 410 | | | | | 415 | |
| Gly | Arg | Phe | Leu | Gln | Pro | Val | Asp | Asp | Thr | Gln | His | Leu | Thr | Val | Ala |
| | | | 420 | | | | | 425 | | | | | 430 | | |
| Thr | Leu | Glu | Glu | Arg | Pro | Phe | Val | Ile | Val | Glu | Pro | Ala | Asp | Pro | Ile |
| | | | 435 | | | | | 440 | | | | 445 | | | |
| Ser | Gly | Thr | Cys | Ile | Arg | Asp | Ser | Val | Pro | Cys | Arg | Ser | Gln | Leu | Asn |
| | 450 | | | | | 455 | | | | | 460 | | | | |
| Arg | Thr | His | Ser | Pro | Pro | Pro | Asp | Ala | Pro | Arg | Pro | Glu | Lys | Arg | Cys |
| 465 | | | | | 470 | | | | 475 | | | | | | 480 |
| Cys | Lys | Gly | Phe | Cys | Ile | Asp | Ile | Leu | Lys | Arg | Leu | Ala | His | Thr | Ile |
| | | | | 485 | | | | | 490 | | | | | 495 | |
| Gly | Phe | Ser | Tyr | Asp | Leu | Tyr | Leu | Val | Thr | Asn | Gly | Lys | His | Gly | Lys |
| | | | 500 | | | | | 505 | | | | | 510 | | |
| Lys | Ile | Asp | Gly | Val | Trp | Asn | Gly | Met | Ile | Gly | Glu | Val | Phe | Tyr | Gln |
| | | | 515 | | | | 520 | | | | | 525 | | | |
| Arg | Ala | Asp | Met | Ala | Ile | Gly | Ser | Leu | Thr | Ile | Asn | Glu | Glu | Arg | Ser |
| | 530 | | | | | 535 | | | | | 540 | | | | |
| Glu | Ile | Val | Asp | Phe | Ser | Val | Pro | Phe | Val | Glu | Thr | Gly | Ile | Ser | Val |
| 545 | | | | | 550 | | | | | 555 | | | | | 560 |
| Met | Val | Ala | Arg | Ser | Asn | Gly | Thr | Val | Ser | Pro | Ser | Ala | Phe | Leu | Glu |
| | | | | 565 | | | | | 570 | | | | | 575 | |
| Pro | Tyr | Ser | Pro | Ala | Val | Trp | Val | Met | Met | Phe | Val | Met | Cys | Leu | Thr |
| | | | 580 | | | | | 585 | | | | | 590 | | |
| Val | Val | Ala | Val | Thr | Val | Phe | Ile | Phe | Glu | Tyr | Leu | Ser | Pro | Val | Gly |
| | | | 595 | | | | 600 | | | | | 605 | | | |
| Tyr | Asn | Arg | Ser | Leu | Ala | Thr | Gly | Lys | Arg | Pro | Gly | Gly | Ser | Thr | Phe |
| | 610 | | | | | 615 | | | | | 620 | | | | |
| Thr | Ile | Gly | Lys | Ser | Ile | Trp | Leu | Leu | Trp | Ala | Leu | Val | Phe | Asn | Asn |
| 625 | | | | | 630 | | | | | 635 | | | | | 640 |
| Ser | Val | Pro | Val | Glu | Asn | Pro | Arg | Gly | Thr | Thr | Ser | Lys | Ile | Met | Val |
| | | | | 645 | | | | | 650 | | | | | 655 | |
| Leu | Val | Trp | Ala | Phe | Phe | Ala | Val | Ile | Phe | Leu | Ala | Ser | Tyr | Thr | Ala |
| | | | 660 | | | | | 665 | | | | | 670 | | |
| Asn | Leu | Ala | Ala | Phe | Met | Ile | Gln | Glu | Glu | Tyr | Val | Asp | Thr | Val | Ser |
| | | | 675 | | | | | 680 | | | | | 685 | | |
| Gly | Leu | Ser | Asp | Arg | Lys | Phe | Gln | Arg | Pro | Gln | Glu | Gln | Tyr | Pro | Pro |
| | 690 | | | | | 695 | | | | | 700 | | | | |
| Leu | Lys | Phe | Gly | Thr | Val | Pro | Asn | Gly | Ser | Thr | Glu | Lys | Asn | Ile | Arg |
| 705 | | | | | 710 | | | | | 715 | | | | | 720 |
| Ser | Asn | Tyr | Pro | Asp | Met | His | Ser | Tyr | Met | Val | Arg | Tyr | Asn | Gln | Pro |
| | | | | 725 | | | | | 730 | | | | | 735 | |
| Arg | Val | Glu | Glu | Ala | Leu | Thr | Gln | Leu | Lys | Ala | Gly | Lys | Leu | Asp | Ala |
| | | | 740 | | | | | 745 | | | | | 750 | | |
| Phe | Ile | Tyr | Asp | Ala | Ala | Val | Leu | Asn | Tyr | Met | Ala | Arg | Lys | Asp | Glu |
| | | | 755 | | | | | 760 | | | | | 765 | | |
| Gly | Cys | Lys | Leu | Val | Thr | Ile | Gly | Ser | Gly | Lys | Val | Phe | Ala | Thr | Thr |
| | 770 | | | | | 775 | | | | | 780 | | | | |
| Gly | Tyr | Gly | Ile | Ala | Leu | His | Lys | Gly | Ser | Arg | Trp | Lys | Arg | Pro | Ile |
| 785 | | | | | 790 | | | | | 795 | | | | | 800 |

Asp Leu Ala Leu Leu Gln Phe Leu Gly Asp Glu Ile Glu Met Leu
                805             810             815

Glu Arg Leu Trp Leu Ser Gly Ile Cys His Asn Asp Lys Ile Glu Val
            820             825             830

Met Ser Ser Lys Leu Asp Ile Asp Asn Met Ala Gly Val Phe Tyr Met
            835             840             845

Leu Leu Val Ala Met Gly Leu Ser Leu Leu Val Phe Ala Trp Glu His
        850             855             860

Leu Val Tyr Trp Arg Leu Arg His Cys Leu Gly Pro Thr His Arg Met
865             870             875                     880

Asp Phe Leu Leu Ala Phe Ser Arg Gly Met Tyr Ser Cys Cys Ser Ala
            885             890             895

Glu Ala Ala Pro Pro Pro Ala Lys Pro Pro Pro Pro Gln Pro Leu
            900             905             910

Pro Ser Pro Ala Tyr Pro Ala Ala Arg Pro Pro Pro Gly Pro Ala Pro
            915             920             925

Phe Val Pro Arg Glu Arg Ala Ala Ala Asp Arg Trp Arg Arg Ala Lys
        930             935             940

Gly Thr Gly Pro Pro Gly Gly Ala Ala Leu Ala Asp Gly Phe His Arg
945             950             955                     960

Tyr Tyr Gly Pro Ile Glu Pro Gln Gly Leu Gly Leu Gly Glu Ala Arg
                965             970             975

Ala Ala Pro Arg Gly Ala Ala Gly Arg Pro Leu Ser Pro Pro Thr Thr
            980             985             990

Gln Pro Pro Gln Lys Pro Pro Pro Ser Tyr Phe Ala Ile Val Arg Glu
        995             1000            1005

Gln Glu Pro Ala Glu Pro Pro Ala Gly Ala Phe Pro Gly Phe Pro Ser
    1010            1015            1020

Pro Pro Ala Pro Pro Ala Ala Ala Ala Ala Ala Val Gly Pro Pro Leu
1025            1030            1035            1040

Cys Arg Leu Ala Phe Glu Asp Glu Ser Pro Pro Ala Pro Ser Ala Gly
            1045            1050            1055

Arg Val Leu Thr Pro Arg Ala Ser Arg Cys Trp Val Gly Ala Arg Ala
        1060            1065            1070

Ala Arg Ala Leu Gly Pro Arg Pro His His Arg Arg Val Arg Thr Ala
    1075            1080            1085

Pro Pro Pro Cys Ala Tyr Leu Asp Leu Glu Pro Ser Pro Ser Asp Ser
    1090            1095            1100

Glu Asp Ser Glu Ser Leu Gly Gly Ala Ser Leu Gly Gly Leu Glu Pro
1105            1110            1115            1120

Trp Trp Phe Ala Asp Phe Pro Tyr Pro Tyr Ala Glu Arg Leu Gly Pro
            1125            1130            1135

Pro Pro Gly Arg Tyr Trp Ser Val Asp Lys Leu Gly Gly Trp Arg Ala
        1140            1145            1150

Gly Ser Trp Asp Tyr Leu Pro Pro Arg Gly Gly Pro Ala Trp His Cys
    1155            1160            1165

Arg His Cys Ala Ser Leu Glu Leu Leu Pro Pro Pro Arg His Leu Ser
1170            1175            1180

Cys Ser His Asp Gly Leu Asp Gly Gly Trp Trp Ala Pro Pro Pro Pro
1185            1190            1195            1200

Pro Trp Ala Ala Gly Pro Pro Ala Pro Arg Arg Ala Arg Cys Gly Cys
            1205            1210            1215

Pro Arg Pro His Pro His Arg Pro Arg Ala Ser His Arg Ala Pro Ala

|       |       |       |       |       |       |       |       |       |       |       |       |       |       |       |
|-------|-------|-------|-------|-------|-------|-------|-------|-------|-------|-------|-------|-------|-------|-------|
|       |       |       |       | 1220  |       |       |       | 1225  |       |       |       | 1230  |       |       |
| Ala   | Ala   | Pro   | His   | His   | His   | Arg   | His   | Arg   | Arg   | Ala   | Ala   | Gly   | Gly   | Trp   | Asp
|       |       | 1235  |       |       |       | 1240  |       |       |       |       | 1245  |       |       |       |
| Leu   | Pro   | Pro   | Pro   | Ala   | Pro   | Thr   | Ser   | Arg   | Ser   | Leu   | Glu   | Asp   | Leu   | Ser   | Ser
|       | 1250  |       |       |       |       | 1255  |       |       |       |       | 1260  |       |       |       |
| Cys   | Pro   | Arg   | Ala   | Ala   | Pro   | Thr   | Arg   | Arg   | Leu   | Thr   | Gly   | Pro   | Ser   | Arg   | His
| 1265  |       |       |       |       | 1270  |       |       |       |       | 1275  |       |       |       |       | 1280
| Ala   | Arg   | Arg   | Cys   | Pro   | His   | Ala   | Ala   | His   | Trp   | Gly   | Pro   | Pro   | Leu   | Pro   | Thr
|       |       |       |       | 1285  |       |       |       |       | 1290  |       |       |       |       | 1295  |
| Ala   | Ser   | His   | Arg   | Arg   | His   | Arg   | Gly   | Gly   | Asp   | Leu   | Gly   | Thr   | Arg   | Arg   | Gly
|       |       |       |       | 1300  |       |       |       |       | 1305  |       |       |       | 1310  |       |
| Ser   | Ala   | His   | Phe   | Ser   | Ser   | Leu   | Glu   | Ser   | Glu   | Val   |       |       |       |       |
|       |       |       | 1315  |       |       |       |       | 1320  |       |       |       |       |       |       |

( 2 ) INFORMATION FOR SEQ ID NO: 5:

( i ) SEQUENCE CHARACTERISTICS:
        ( A ) LENGTH: 4392 nucleic acids
        ( B ) TYPE: nucleic acid
        ( C ) STRANDEDNESS: double strand
        ( D ) TOPOLOGY: linear ( i i ) MOLECULE TYPE: cDNA ( v i ) ORIGINAL SOURCE:
        ( A ) ORGANISM: mouse
        ( F ) TISSUE TYPE: cerebellum ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:5: FROM 1 to 4392

( x i ) SEQUENCE DESCRIPTION: SEQ ID NO:5:

| ATG | GGC | AGA | CTG | GGC | TAC | TGG | ACC | 24  |
|-----|-----|-----|-----|-----|-----|-----|-----|-----|
| TTG | CTG | GTA | TTG | CCG | GCC | CTT | CTG | 48  |
| GTC | TGG | CAC | GGT | CCG | GCG | CAG | AAC | 72  |
| GCG | GCG | GCG | GAG | AAG | GGT | ACT | CCA | 96  |
| GCG | CTG | AAC | ATT | GCG | GTG | CTG | CTG | 120 |
| GGT | CAC | AGC | CAC | GAC | GTG | ACA | GAA | 144 |
| CGC | GAA | CTT | CGA | AAT | CTG | TGG | GGC | 168 |
| CCG | GAG | CAG | GCA | ACC | GGC | TTG | CCC | 192 |
| CTG | GAT | GTG | AAC | GTG | GTG | GCG | TTA | 216 |
| TTG | ATG | AAC | CGC | ACT | GAC | CCT | AAG | 240 |
| AGC | CTC | ATC | ACG | CAT | GTG | TGC | GAC | 264 |
| CTC | ATG | TCC | GGG | GCG | CGC | ATC | CAT | 288 |
| GGC | TTG | GTG | TTT | GGA | GAT | GAT | ACG | 312 |
| GAC | CAA | GAG | GCT | GTG | GCT | CAG | ATG | 336 |
| CTG | GAT | TTT | ATC | TCC | TCA | CAG | ACT | 360 |
| TTC | ATC | CCC | ATC | TTG | GGC | ATT | CAT | 384 |
| GGG | GGT | GCA | TCT | ATG | ATC | ATG | GCT | 408 |
| GAC | AAG | GAT | CCG | ACA | TCC | ACG | TTC | 432 |
| TTC | CAG | TTT | GGA | GCT | TCC | ATC | CAG | 456 |

| | | | | | | | |
|---|---|---|---|---|---|---|---|
| CAG | CAA | GCC | ACG | GTC | ATG | CTG | AAG | 480 |
| ATC | ATG | CAG | GAC | TAT | GAC | TGG | CAT | 504 |
| GTC | TTC | TCC | TTG | GTC | ACC | ACC | ATC | 528 |
| TTC | CCT | GGC | TAC | AGA | GAC | TTC | ATC | 552 |
| AGC | TTC | ATC | AAG | ACA | ACA | GTG | GAC | 576 |
| AAC | AGC | TTT | GTG | GGC | TGG | GAT | ATG | 600 |
| CAG | AAC | GTG | ATC | ACA | CTG | GAC | ACC | 624 |
| TCT | TTT | GAG | GAC | GCC | AAG | ACA | CAG | 648 |
| GTC | CAG | CTG | AAG | AAG | ATC | CAC | TCC | 672 |
| TCT | GTC | ATC | CTG | CTC | TAC | TGC | TCC | 696 |
| AAG | GAT | GAG | GCT | GTC | CTC | ATC | CTG | 720 |
| AGC | GAG | GCT | CGC | TCT | CTT | GGC | CTC | 744 |
| ACC | GGC | TAC | GAT | TTC | TTC | TGG | ATT | 768 |
| GTC | CCC | AGT | TTG | GTC | TCC | GGG | AAC | 792 |
| ACA | GAG | CTC | ATC | CCC | AAA | GAG | TTT | 816 |
| CCA | TCG | GGT | CTC | ATT | TCA | GTC | TCT | 840 |
| TAC | GAC | GAC | TGG | GAC | TAC | AGT | CTG | 864 |
| GAG | GCA | AGA | GTG | AGA | GAC | GGT | CTT | 888 |
| GGG | ATC | TTA | ACC | ACT | GCC | GCA | TCT | 912 |
| TCC | ATG | TTG | GAG | AAA | TTC | TCC | TAC | 936 |
| ATT | CCC | GAG | GCC | AAG | GCC | AGC | TGC | 960 |
| TAC | GGG | CAG | ACA | GAG | AAG | CCG | GAG | 984 |
| ACC | CCG | CTA | CAC | ACT | CTG | CAC | CAA | 1008 |
| TTT | ATG | GTC | AAT | GTG | ACT | TGG | GAT | 1032 |
| GGC | AAG | GAC | TTG | TCC | TTC | ACT | GAG | 1056 |
| GAA | GGC | TAT | CAG | GTG | CAC | CCC | AGG | 1080 |
| CTT | GTG | GTG | ATC | GTG | CTG | AAT | AAG | 1104 |
| GAC | CGG | GAA | TGG | GAA | AAG | GTG | GGC | 1128 |
| AAG | TGG | GAG | AAT | CAG | ACT | CTG | AGG | 1152 |
| CTG | CGG | CAT | GCT | GTG | TGG | CCA | AGG | 1176 |
| TAT | AAG | TCC | TTT | TCT | GAC | TGT | GAG | 1200 |
| CCA | GAT | GAC | AAC | CAC | CTC | AGC | ATT | 1224 |
| GTC | ACC | TTG | GAG | GAA | GCC | CCC | TTC | 1248 |
| GTC | ATC | GTA | GAA | GAC | ATA | GAC | CCA | 1272 |
| CTG | ACT | GAG | ACC | TGC | GTC | AGG | AAC | 1296 |
| ACG | GTA | CCC | TGT | CGG | AAG | TTT | GTC | 1320 |
| AAG | ATC | AAC | AAT | TCA | ACC | AAC | GAA | 1344 |
| GGG | ATG | AAT | GTG | AAG | AAG | TGC | TGC | 1368 |
| AAG | GGG | TTC | TGC | ATC | GAC | ATC | CTT | 1392 |
| AAG | AAA | CTG | TCC | AGA | ACT | GTA | AAG | 1416 |

| | | | | | | | |
|---|---|---|---|---|---|---|---|
| TTC | ACC | TAT | GAC | CTC | TAC | CTG | GTG | 1440 |
| ACC | AAT | GGG | AAG | CAT | GGG | AAA | AAG | 1464 |
| GTT | AAC | AAT | GTG | TGG | AAT | GGA | ATG | 1488 |
| ATA | GGC | GAA | GTG | GTC | TAT | CAA | CGA | 1512 |
| GCA | GTT | ATG | GCC | GTG | GGC | TCC | CTC | 1536 |
| ACC | ATC | AAT | GAG | GAG | CGT | TCA | GAA | 1560 |
| GTG | GTG | GAC | TTC | TCC | GTG | CCC | TTT | 1584 |
| GTG | GAG | ACA | GGA | ATC | AGT | GTC | ATG | 1608 |
| GTC | TCC | AGG | AGT | AAT | GGC | ACT | GTT | 1632 |
| TCC | CCT | TCT | GCT | TTC | CTT | GAA | CCC | 1656 |
| TTC | AGC | GCC | TCT | GTC | TGG | GTG | ATG | 1680 |
| ATG | TTC | GTG | ATG | CTG | CTC | ATT | GTC | 1704 |
| TCT | GCC | ATT | GCT | GTC | TTC | GTT | TTT | 1728 |
| GAA | TAC | TTC | AGT | CCT | GTT | GGA | TAC | 1752 |
| AAC | AGA | AAC | TTA | GCC | AAA | GGG | AAA | 1776 |
| GCT | CCC | CAT | GGG | CCT | TCT | TTT | ACC | 1800 |
| ATT | GGA | AAA | GCT | ATA | TGG | CTC | CTC | 1824 |
| TGG | GGC | CTG | GTC | TTC | AAC | AAT | TCT | 1848 |
| GTG | CCC | GTC | CAG | AAT | CCT | AAA | GGC | 1872 |
| ACA | ACC | AGC | AAG | ATA | ATG | GTA | TCA | 1896 |
| GTG | TGG | GCC | TTC | TTT | GCC | GTC | ATC | 1920 |
| TTC | CTT | GCA | AGT | TAC | ACA | GCC | AAC | 1944 |
| CTG | GCT | GCC | TTC | ATG | ATC | CAG | GAG | 1968 |
| GAG | TTT | GTG | GAC | CAA | GTG | ACT | GGC | 1992 |
| CTC | AGT | GAC | AAG | AAG | TTC | CAG | AGA | 2016 |
| CCT | CAT | GAC | TAT | TCT | CCG | CCT | TTC | 2040 |
| CGA | TTT | GGG | ACA | GTA | CCC | AAT | GGA | 2064 |
| AGT | ACA | GAA | AGG | AAT | ATT | CGT | AAC | 2088 |
| AAC | TAC | CCC | TAT | ATG | CAC | CAG | TAC | 2112 |
| ATG | ACC | AAA | TTC | AAC | CAG | AGG | GGC | 2136 |
| GTA | GAG | GAT | GCC | TTG | GTC | AGC | TTG | 2160 |
| AAA | ACT | GGG | AAG | TTG | GAC | GCT | TTC | 2184 |
| ATC | TAT | GAC | GCA | GCT | GTC | TTG | AAC | 2208 |
| TAC | AAG | GCC | GGG | AGG | GAT | GAA | GGC | 2232 |
| TGT | AAA | CTG | GTG | ACC | ATT | GGG | AGC | 2256 |
| GGG | TAC | ATC | TTT | GCC | ACC | ACA | GGC | 2280 |
| TAT | GGA | ATT | GCT | CTG | CAG | AAG | GGC | 2304 |
| TCA | CCC | TGG | AAG | AGG | CAG | ATT | GAC | 2328 |
| CTC | GCT | CTG | CTC | CAG | TTT | GTT | GGT | 2352 |
| GAC | GGT | GAG | ATG | GAA | GAG | CTG | GAG | 2376 |

| | | | | | | | |
|---|---|---|---|---|---|---|---|
| ACA | CTG | TGG | CTT | ACG | GGC | ATC | TGC | 2400 |
| CAC | AAC | GAG | AAG | AAT | GAG | GTG | ATG | 2424 |
| AGC | AGC | CAG | CTG | GAC | ATC | GAC | AAC | 2448 |
| ATG | GCA | GGA | GTT | TTC | TAC | ATG | CTG | 2472 |
| GCT | GCA | GCT | ATG | GCC | CTC | AGC | CTC | 2496 |
| ATC | ACC | TTC | ATC | TGG | GAG | CAC | CTC | 2520 |
| TTC | TAC | TGG | AAG | CTG | CGC | TTC | TGC | 2544 |
| TTC | ACA | GGC | GTG | TGT | TCT | GAC | CGG | 2568 |
| CCC | GGG | CTG | CTC | TTC | TCC | ATC | AGC | 2592 |
| AGG | GGC | ATC | TAC | AGT | TGC | ATC | CAT | 2616 |
| GGA | GTG | CAC | ATT | GAA | GAA | AAG | AAG | 2640 |
| AAG | TCT | CCA | GAC | TTC | AAT | CTG | ACT | 2664 |
| GGG | TCA | CAG | AGC | AAC | ATG | CTA | AAG | 2688 |
| CTT | CTC | CGC | TCA | GCT | AAA | AAC | ATC | 2712 |
| TCC | AAC | ATG | TCC | AAC | ATG | AAC | TCC | 2736 |
| TCG | CGA | ATG | GAC | TCA | CCC | AAA | AGA | 2760 |
| GCT | GCT | GAC | TTC | ATC | CAA | AGA | GGC | 2784 |
| TCA | CTT | ATT | GTG | GAC | ATG | GTT | TCA | 2808 |
| GAC | AAG | GGA | AAT | TTG | ATA | TAC | TCA | 2832 |
| GAT | AAC | AGG | TCC | TTT | CAA | GGG | AAG | 2856 |
| GAC | AGT | ATA | TTT | GGA | GAA | AAC | ATG | 2880 |
| AAT | GAA | CTG | CAA | ACA | TTT | GTG | GCC | 2904 |
| AAC | AGG | CAC | AAG | GAT | AGT | CTC | AGT | 2928 |
| AAC | TAT | GTG | TTT | CAG | GGA | CAG | CAT | 2952 |
| CCT | CTC | ACT | CTC | AAT | GAG | TCC | AAC | 2976 |
| CCC | AAC | ACA | GTG | GAG | GTG | GCT | GTC | 3000 |
| AGC | ACT | GAA | TCC | AAA | GGG | AAC | TCC | 3024 |
| CGA | CCC | CGG | CAG | CTT | TGG | AAG | AAA | 3048 |
| TCC | ATG | GAG | TCT | CTA | CGC | CAG | GAT | 3072 |
| TCT | CTA | AAC | CAG | AAC | CCA | GTC | TCC | 3096 |
| CAG | AGG | GAT | GAG | AAG | ACT | GCA | GAG | 3120 |
| AAT | AGG | ACC | CAC | TCC | CTA | AAG | AGT | 3144 |
| CCT | AGG | TAT | CTT | CCA | GAA | GAG | GTA | 3168 |
| GCC | CAT | TCT | GAC | ATT | TCT | GAA | ACC | 3192 |
| TCA | AGC | CGG | GCC | ACA | TGC | CAC | AGG | 3216 |
| GAG | CCA | GAT | AAT | AAT | AAG | AAC | CAC | 3240 |
| AAG | ACC | AAG | GAT | AAC | TTC | AAA | AGG | 3264 |
| TCA | ATG | GCC | TCT | AAA | TAC | CCC | AAG | 3288 |
| GAC | TGT | AGT | GAG | GTT | GAA | CGT | ACC | 3312 |
| TAC | GTG | AAA | ACC | AAA | GCA | AGT | TCT | 3336 |

-continued

| | | | | | | | |
|---|---|---|---|---|---|---|---|
| CCC | AGG | GAT | AAG | ATC | TAC | ACC | ATC | 3360 |
| GAT | GGT | GAG | AAG | GAG | CCC | AGC | TTC | 3384 |
| CAC | TTA | GAT | CCT | CCA | CAG | TTC | ATT | 3408 |
| GAA | AAC | ATA | GTC | TTG | CCT | GAG | AAT | 3432 |
| GTG | GAC | TTC | CCA | GAT | ACC | TAC | CAA | 3456 |
| GAT | CAC | AAT | GAG | AAT | TTC | CGC | AAG | 3480 |
| GGG | GAC | TCC | ACA | CTG | CCC | ATG | AAC | 3504 |
| AGG | AAC | CCA | CTA | CAC | AAT | GAA | GAT | 3528 |
| GGG | CTT | CCC | AAC | AAT | GAC | CAG | TAT | 3552 |
| AAA | CTC | TAT | GCC | AAG | CAC | TTT | ACC | 3576 |
| TTG | AAA | GAC | AAG | GGT | TCC | CCA | CAT | 3600 |
| AGT | GAG | GGC | AGT | GAT | CGA | TAT | CGG | 3624 |
| CAG | AAC | TCC | ACG | CAT | TGC | AGA | AGC | 3648 |
| TGC | CTC | TCA | AAC | CTG | CCC | ACC | TAC | 3672 |
| TCA | GGC | CAC | TTT | ACC | ATG | AGA | TCT | 3696 |
| CCT | TTC | AAG | TGT | GAT | GCC | TGT | CTG | 3720 |
| CGG | ATG | GGG | AAC | CTC | TAT | GAC | ATT | 3744 |
| GAT | GAA | GAC | CAG | ATG | CTT | CAG | GAG | 3768 |
| ACA | GGC | AAC | CCA | GCT | ACT | CGT | GAG | 3792 |
| GAG | GCC | TAC | CAG | CAG | GAC | TGG | TCA | 3816 |
| CAG | AAC | AAC | GCC | CTC | CAG | TTC | CAG | 3840 |
| AAG | AAC | AAG | CTA | AAG | ATT | AAT | CGA | 3864 |
| CAG | CAC | TCC | TAT | GAT | AAC | ATT | CTC | 3888 |
| GAC | AAA | CCC | AGG | GAG | ATA | GAC | CTT | 3912 |
| AGC | AGG | CCC | TCT | CGT | AGC | ATA | AGC | 3936 |
| CTC | AAG | GAC | AGG | GAA | AGG | CTA | CTG | 3960 |
| GAG | GGC | AAC | TTA | TAC | GGG | AGC | CTG | 3984 |
| TTC | AGT | GTC | CCC | TCA | AGC | AAA | CTC | 4008 |
| TTG | GGG | AAC | AAA | AGC | TCC | CTT | TTC | 4032 |
| CCC | CAA | GGT | CTG | GAG | GAC | AGC | AAG | 4056 |
| AGG | AGC | AAA | TCT | CTC | TTG | CCA | GAC | 4080 |
| CAT | ACC | TCT | GAT | AAT | CCT | TTC | CTC | 4104 |
| CAC | ACG | TAC | GGG | GAT | GAC | CAA | CGC | 4128 |
| TTA | GTT | ATT | GGG | AGA | TGT | CCC | TCG | 4152 |
| GAC | CCT | TAC | AAA | CAC | TCA | TTG | CCA | 4176 |
| TCA | CAG | GCA | GTA | AAT | GAC | AGC | TAT | 4200 |
| CTT | CGG | TCA | TCC | TTG | AGG | TCA | ACA | 4224 |
| GCA | TCA | TAT | TGC | TCC | AGG | GAC | AGT | 4248 |
| CGG | GGC | CAC | AGT | GAT | GTG | TAT | ATT | 4272 |
| TCA | GAG | CAT | GTT | ATG | CCT | TAT | GCT | 4296 |

| | | | | | | | |
|---|---|---|---|---|---|---|---|
| GCA | AAT | AAG | AAT | AAC | ATG | TAC | TCT | 4320 |
| ACC | CCC | AGG | GTT | TTA | AAT | TCC | TGC | 4344 |
| AGC | AAT | AGA | CGT | GTG | TAC | AAG | AAA | 4368 |
| ATG | CCT | AGT | ATT | GAA | TCT | GAT | GTC | 4392 |

( 2 ) INFORMATION FOR SEQ ID NO: 6:

( i ) SEQUENCE CHARACTERISTICS:
        ( A ) LENGTH: 4446 nucleic acids
        ( B ) TYPE: nucleic acid
        ( C ) STRANDEDNESS: double strand
        ( D ) TOPOLOGY: linear ( i i ) MOLECULE TYPE: cDNA ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:6: FROM 1 to 4446

( x i ) SEQUENCE DESCRIPTION: SEQ ID NO:6:

| | | | | | | | |
|---|---|---|---|---|---|---|---|
| ATG | AAG | CCC | AGC | GCA | GAG | TGC | TGT | 24 |
| TCT | CCC | AAG | TTC | TGG | TTG | GTG | TTG | 48 |
| GCC | GTC | TTG | GCC | GTA | TCG | GGC | AGC | 72 |
| AAA | GCT | CGT | TCC | CAA | AAG | AGC | GCC | 96 |
| CCC | AGC | ATC | GGC | ATC | GCT | GTC | ATC | 120 |
| CTC | GTG | GGC | ACT | TCC | GAC | GAA | GTG | 144 |
| GCC | ATA | AAA | GAT | GCC | CAC | GAG | AAA | 168 |
| GAT | GAC | TTC | CAT | CAT | CTC | TCA | GTA | 192 |
| GTT | CCC | CGG | GTG | GAG | CTG | GTA | GCC | 216 |
| ATG | AAC | GAG | ACT | GAC | CCA | AAG | AGC | 240 |
| ATA | ATC | ACC | CGC | ATC | TGC | GAT | CTT | 264 |
| ATG | TCT | GAC | CGG | AAG | ATC | CAG | GGG | 288 |
| GTG | GTG | CTC | GCG | GAT | GAC | ACG | GAC | 312 |
| CAG | GAA | GCC | ATC | GCC | CAG | ATC | CTC | 336 |
| GAT | TTC | ATT | TCT | GCT | CAG | ACT | CTC | 360 |
| ACC | CCC | ATC | CTG | GGC | ATC | CAT | GGG | 384 |
| GGC | TCA | TCT | ATG | ATA | ATG | GCA | GAT | 408 |
| AAG | GAT | GAG | TCC | TCC | ATG | TTC | TTC | 432 |
| CAG | TTT | GGC | CCA | TCC | ATT | GAA | CAG | 456 |
| CAA | GCT | TCT | GTC | ATG | CTC | AAC | ATC | 480 |
| ATG | GAA | GAA | TAC | GAC | TGG | TAC | ATC | 504 |
| TTC | TCC | ATC | GTC | ACC | ACC | TAC | TTC | 528 |
| CCC | GGC | TAC | CAG | GAC | TTC | GTG | AAC | 552 |
| AAG | ATC | CGC | AGC | ACT | ATT | GAG | AAC | 576 |
| AGC | TTT | GTG | GGC | TGG | GAG | CTC | GAG | 600 |

| | | | | | | | |
|---|---|---|---|---|---|---|---|
| GAA | GTC | CTC | CTG | CTA | GAC | ATG | TCT | 624 |
| CTA | GAC | GAT | GGC | GAC | TCT | AAG | ATT | 648 |
| CAG | AAT | CAG | CTG | AAG | AAG | CTG | CAG | 672 |
| AGC | CCC | ATC | ATT | CTC | CTC | TAC | TGC | 696 |
| ACA | AAG | GAA | GAA | GCC | ACC | TAC | ATC | 720 |
| TTC | GAA | GTA | GCT | AAC | TCA | GTT | GGG | 744 |
| CTG | ACT | GGC | TAC | GGC | TAC | ACA | TGG | 768 |
| ATC | GTG | CCG | AGT | CTG | GTG | GCG | GGG | 792 |
| GAT | ACA | GAC | ACG | GTG | CCT | TCA | GAG | 816 |
| TTC | CCC | ACG | GGG | CTC | ATC | TCT | GTG | 840 |
| TCA | TAT | GAC | GAA | TGG | GAC | TAT | GGC | 864 |
| CTT | CCT | GCC | AGA | GTG | AGA | GAT | GGG | 888 |
| ATT | GCC | ATC | ATC | ACC | ACT | GCT | GCC | 912 |
| TCG | GAC | ATG | CTG | TCC | GAA | CAC | AGT | 936 |
| TTC | ATC | CCT | GAG | CCC | AAG | AGC | AGT | 960 |
| TGC | TAC | AAC | ACC | CAC | GAG | AAG | AGG | 984 |
| ATC | TAC | CAG | TCT | AAC | ATG | CTG | AAT | 1008 |
| AGG | TAT | CTG | ATC | AAC | GTC | ACT | TTT | 1032 |
| GAA | GGG | AGA | AAC | CTG | TCC | TTC | AGT | 1056 |
| GAA | GAT | GGC | TAC | CAG | ATG | CAT | CCG | 1080 |
| AAG | CTG | GTG | ATA | ATC | CTT | CTG | AAC | 1104 |
| AAG | GAG | AGG | AAG | TGG | GAG | AGG | GTG | 1128 |
| GGA | AAA | TGG | AAA | GAC | AAG | TCC | CTG | 1152 |
| CAG | ATG | AAA | TAC | TAC | GTG | TGG | CCT | 1176 |
| CGA | ATG | TGT | CCA | GAG | ACT | GAA | GAA | 1200 |
| CAG | GAA | GAT | GAC | CAT | CTG | AGC | ATC | 1224 |
| GTT | ACC | TTG | GAG | GAG | GCA | CCG | TTT | 1248 |
| GTC | ATT | GTG | GAA | AGT | GTG | GAC | CCT | 1272 |
| CTC | AGT | GGG | ACC | TGC | ATG | CGG | AAT | 1296 |
| ACA | GTC | CCG | TGC | CAG | AAG | CGC | ATC | 1320 |
| ATC | TCT | GAG | AAT | AAA | ACA | GAT | GAG | 1344 |
| GAA | CCA | GGC | TAC | ATC | AAA | AAA | TGC | 1368 |
| TGC | AAG | GGG | TTT | TGT | ATT | GAT | ATC | 1392 |
| CTT | AAG | AAA | ATT | TCT | AAG | TCT | GTG | 1416 |
| AAG | TTC | ACC | TAT | GAC | CTT | TAC | CTG | 1440 |
| GTG | ACC | AAT | GGC | AAG | CAT | GGA | AAG | 1464 |
| AAA | ATC | AAC | GGG | ACC | TGG | AAC | GGC | 1488 |
| ATG | ATT | GGT | GAG | GTG | GTC | ATG | AAG | 1512 |
| AGG | GCC | TAC | ATG | GCA | GTG | GGA | TCA | 1536 |
| CTA | ACT | ATC | AAT | GAA | GAA | CGG | TCA | 1560 |

| GAG | GTG | GTT | GAC | TTC | TCT | GTG | CCC | 1584 |
| TTC | ATA | GAG | ACT | GGC | ATC | AGT | GTC | 1608 |
| ATG | GTA | TCA | CGC | AGC | AAT | GGG | ACT | 1632 |
| GTG | TCA | CCT | TCT | GCC | TTC | TTA | GAG | 1656 |
| CCA | TTC | AGT | GCT | GAC | GTG | TGG | GTG | 1680 |
| ATG | ATG | TTT | GTG | ATG | CTG | CTC | ATT | 1704 |
| GTC | TCT | GCT | GTA | GCT | GTC | TTT | GTC | 1728 |
| TTT | GAA | TAC | TTC | AGC | CCT | GTG | GGT | 1752 |
| TAC | AAC | CGG | TGC | CTA | GCT | GAT | GGC | 1776 |
| AGA | GAG | CCA | GGC | GGC | CCA | TCT | TTC | 1800 |
| ACC | ATC | GGC | AAA | GCG | ATT | TGG | TTA | 1824 |
| CTC | TGG | GGT | CTG | GTG | TTT | AAC | AAC | 1848 |
| TCC | GTA | CCT | GTG | CAG | AAC | CCA | AAG | 1872 |
| GGG | ACC | ACC | TCC | AAG | ATC | ATG | GTG | 1896 |
| TCA | GTG | TGG | GCC | TTC | TTT | GCT | GTC | 1920 |
| ATT | TTC | CTG | GCC | AGC | TAC | ACT | GCC | 1944 |
| AAC | TTA | GCC | GCC | TTC | ATG | ATC | CAA | 1968 |
| GAG | GAG | TAT | GTG | GAC | CAG | GTT | TCC | 1992 |
| GGC | CTG | AGT | GAC | AAG | AAG | TTC | CAG | 2016 |
| AGA | CCT | AAT | GAC | TTC | TCA | CCC | CCT | 2040 |
| TTC | CGC | TTT | GGG | ACT | GTG | CCC | AAT | 2064 |
| GGC | AGC | ACA | GAG | AGG | AAT | ATC | CGT | 2088 |
| AAT | AAC | TAT | GCA | GAA | ATG | CAT | GCC | 2112 |
| TAC | ATG | GGA | AAG | TTC | AAC | CAA | AGG | 2136 |
| GGT | GTA | GAT | GAT | GCC | TTG | CTC | TCC | 2160 |
| CTG | AAA | ACA | GGG | AAA | CTT | GAT | GCA | 2184 |
| TTC | ATC | TAC | GAT | GCA | GCC | GTG | CTC | 2208 |
| AAC | TAC | ATG | GCT | GGA | AGA | GAC | GAA | 2232 |
| GGC | TGC | AAG | CTG | GTG | ACC | ATT | GGC | 2256 |
| AGT | GGC | AAG | GTC | TTT | GCT | TCT | ACG | 2280 |
| GGC | TAT | GGC | ATT | GCT | ATC | CAA | AAA | 2304 |
| GAC | TCT | GGT | TGG | AAA | CGC | CAG | GTG | 2328 |
| GAC | CTT | GCT | ATC | CTG | CAG | CTG | TTT | 2352 |
| GGA | GAT | GGG | GAG | ATG | GAA | GAA | CTG | 2376 |
| GAA | GCT | CTC | TGG | CTC | ACT | GGC | ATT | 2400 |
| TGC | CAC | AAT | GAG | AAG | AAT | GAG | GTT | 2424 |
| ATG | AGC | AGC | CAG | CTG | GAC | ATT | GAC | 2448 |
| AAC | ATG | GCG | GGC | GTC | TTC | TAT | ATG | 2472 |
| TTG | GGG | GCA | GCC | ATG | GCT | CTC | AGC | 2496 |
| CTC | ATC | ACC | TTC | ATC | TGT | GAA | CAT | 2520 |

| | | | | | | | |
|---|---|---|---|---|---|---|---|
| CTC | TTC | TAT | TGG | CAG | TTC | CGA | CAT | 2544 |
| TGC | TTC | ATG | GGT | GTC | TGT | TCT | GGC | 2568 |
| AAG | CCT | GGC | ATG | GTC | TTC | TCC | ATC | 2592 |
| AGC | AGA | GGT | ATC | TAC | AGC | TGT | ATC | 2616 |
| CAC | GGA | GTA | GCT | ATA | GAG | GAG | CGC | 2640 |
| CAA | TCC | GTG | ATG | AAC | TCC | CCC | ACT | 2664 |
| GCC | ACC | ATG | AAC | AAC | ACA | CAC | TCC | 2688 |
| AAT | ATC | CTA | CGC | TTG | CTC | CGA | ACG | 2712 |
| GCC | AAA | AAC | ATG | GCC | AAC | CTG | TCT | 2736 |
| GGA | GTC | AAC | GGC | TCC | CCC | CAG | AGT | 2760 |
| GCC | CTG | GAC | TTC | ATC | CGC | CGT | GAG | 2784 |
| TCC | TCT | GTC | TAT | GAC | ATC | TCT | GAG | 2808 |
| CAT | CGC | CGC | AGC | TTC | ACG | CAT | TCA | 2832 |
| GAC | TGC | AAG | TCG | TAC | AAT | AAC | CCA | 2856 |
| CCC | TGT | GAG | GAA | AAC | CTG | TTC | AGT | 2880 |
| GAC | TAC | ATT | AGT | GAG | GTA | GAG | AGA | 2904 |
| ACA | TTT | GGC | AAC | CTG | CAG | CTG | AAG | 2928 |
| GAC | AGC | AAT | GTG | TAC | CAA | GAC | CAC | 2952 |
| TAT | CAC | CAT | CAC | CAC | CGG | CCC | CAC | 2976 |
| AGC | ATC | GGC | AGC | ACC | AGC | TCC | ATT | 3000 |
| GAT | GGG | CTC | TAT | GAC | TGT | GAC | AAC | 3024 |
| CCA | CCC | TTT | ACC | ACC | CAG | CCC | AGG | 3048 |
| TCA | ATC | AGC | AAG | AAA | CCC | CTG | GAC | 3072 |
| ATT | GGC | CTG | CCC | TCC | TCC | AAA | CAC | 3096 |
| AGC | CAG | CTC | AGC | GAC | CTG | TAC | GGC | 3120 |
| AAG | TTC | TCT | TTC | AAG | AGT | GAC | CGC | 3144 |
| TAC | AGT | GGC | CAT | GAT | GAC | TTG | ATT | 3168 |
| CGA | TCG | GAT | GTC | TCA | GAC | ATC | TCC | 3192 |
| ACG | CAT | ACT | GTC | ACC | TAT | GGC | AAC | 3216 |
| ATC | GAG | GGC | AAC | GCA | GCC | AAG | AGG | 3240 |
| AGG | AAG | CAG | CAA | TAT | AAG | GAC | AGT | 3264 |
| CTA | AAG | AAG | CGG | CCA | GCC | TCG | GCC | 3288 |
| AAA | TCT | AGG | AGG | GAG | TTT | GAT | GAA | 3312 |
| ATC | GAG | CTG | GCC | TAC | CGT | CGC | CGA | 3336 |
| CCA | CCC | CGC | TCC | CCA | GAC | CAC | AAG | 3360 |
| CGC | TAC | TTC | AGG | GAC | AAA | GAA | GGG | 3384 |
| CTC | CGA | GAC | TTC | TAC | CTG | GAC | CAG | 3408 |
| TTC | CGA | ACA | AAG | GAG | AAC | TCG | CCT | 3432 |
| CAC | TGG | GAG | CAC | GTG | GAC | TTA | ACT | 3456 |
| GAC | ATT | TAC | AAA | GAA | CGT | AGT | GAT | 3480 |

| | | | | | | | |
|---|---|---|---|---|---|---|---|
| GAC | TTC | AAG | CGA | GAT | TCG | GTC | AGT | 3504 |
| GGA | GGC | GGG | CCC | TGT | ACC | AAC | AGG | 3528 |
| TCT | CAC | CTT | AAA | CAC | GGA | ACA | GGC | 3552 |
| GAT | AAG | CAC | GGA | GTG | GTA | GGC | GGG | 3576 |
| GTG | CCT | GCT | CCT | TGG | GAG | AAG | AAC | 3600 |
| CTG | ACC | AAT | GTG | GAT | TGG | GAG | GAT | 3624 |
| AGG | TCT | GGG | GGC | AAC | TTC | TGC | CGC | 3648 |
| AGC | TGT | CCC | TCC | AAG | CTG | CAC | AAT | 3672 |
| TAC | TCC | TCT | ACG | GTG | GCA | GGG | CAA | 3696 |
| AAC | TCG | GGC | CGG | CAG | GCC | TGC | ATC | 3720 |
| AGG | TGT | GAG | GCC | TGC | AAG | AAG | GCT | 3744 |
| GGC | AAC | CTG | TAT | GAC | ATC | AGC | GAG | 3768 |
| GAC | AAC | TCC | CTG | CAG | GAA | CTG | GAC | 3792 |
| CAG | CCG | GCT | GCC | CCT | GTG | GCT | GTG | 3816 |
| TCA | TCC | AAC | GCC | TCC | ACC | ACC | AAG | 3840 |
| TAC | CCT | CAA | AGC | CCG | ACT | AAT | TCC | 3864 |
| AAG | GCC | CAG | AAG | AAG | AAT | CGG | AAC | 3888 |
| AAA | CTG | CGC | CGG | CAG | CAC | TCC | TAC | 3912 |
| GAC | ACC | TTC | GTG | GAC | CTG | CAG | AAG | 3936 |
| GAG | GAG | GCC | GCC | TTG | GCC | CCA | CGC | 3960 |
| AGC | GTG | AGC | CTG | AAA | GAC | AAG | GGC | 3984 |
| CGA | TTC | ATG | GAT | GGG | AGC | CCC | TAC | 4008 |
| GCC | CAT | ATG | TTT | GAG | ATG | CCA | GCT | 4032 |
| GGT | GAG | AGC | TCC | TTT | GCC | AAC | AAG | 4056 |
| TCC | TCA | GTG | ACC | ACT | GCC | GGA | CAC | 4080 |
| CAT | CAC | AAC | AAT | CCC | GGC | AGC | GGC | 4104 |
| TAC | ATG | CTC | AGC | AAG | TCG | CTC | TAC | 4128 |
| CCT | GAC | CGG | GTC | ACG | CAA | AAC | CCT | 4152 |
| TTC | ATC | CCC | ACT | TTT | GGG | GAT | GAT | 4176 |
| CAG | TGC | TTG | CTT | CAC | GGC | AGC | AAA | 4200 |
| TCC | TAC | TTC | TTC | AGG | CAG | CCC | ACG | 4224 |
| GTG | GCA | GGG | GCG | TCG | AAA | ACA | AGG | 4248 |
| CCG | GAC | TTC | CGG | GCC | CTT | GTC | ACC | 4272 |
| AAT | AAG | CCA | GTG | GTG | TCG | GCC | CTT | 4296 |
| CAT | GGG | GCT | GTG | CCA | GGT | CGT | TTC | 4320 |
| CAG | AAG | GAC | ATT | TGT | ATA | GGG | AAC | 4344 |
| CAG | TCC | AAC | CCC | TGT | GTG | CCT | AAC | 4368 |
| AAC | AAA | AAC | CCC | AGG | GCT | TTC | AAT | 4392 |
| GGC | TCC | AGC | AAT | GGA | CAT | GTT | TAT | 4416 |
| GAG | AAA | CTT | TCT | AGT | ATT | GAG | TCT | 4440 |

GAT  GTC                                                    4446

( 2 ) INFORMATION FOR SEQ ID NO: 7:

( i ) SEQUENCE CHARACTERISTICS:
        ( A ) LENGTH: 3717 nucleic acids
        ( B ) TYPE: nucleic acid
        ( C ) STRANDEDNESS: double strand
        ( D ) TOPOLOGY: linear ( i i ) MOLECULE TYPE: cDNA ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:7: FROM 1 to 3717

( x i ) SEQUENCE DESCRIPTION: SEQ ID NO:7:

| | | | | | | | | |
|---|---|---|---|---|---|---|---|---|
| ATG | GGT | GGA | GCC | CTG | GGG | CCC | GCC | 24 |
| CTG | CTT | CTC | ACT | TCA | CTC | CTT | GGT | 48 |
| GCT | TGG | GCA | GGG | CTG | GGC | GCA | GGG | 72 |
| CAG | GGA | GAA | CAG | GCC | GTG | ACC | GTG | 96 |
| GCG | GTG | GTG | TTT | GGC | AGC | TCT | GGG | 120 |
| CCA | CTG | CAG | GCC | CAG | GCC | CGG | ACT | 144 |
| CGT | CTC | ACC | CCG | CAG | AAC | TTC | CTG | 168 |
| GAC | TTG | CCT | CTG | GAG | ATC | CAG | CCA | 192 |
| CTC | ACC | ATC | GGG | GTC | AAC | AAT | ACC | 216 |
| AAC | CCC | AGC | AGC | ATC | CTC | ACC | CAA | 240 |
| ATC | TGT | GGG | CTC | CTG | GGT | GCC | GCC | 264 |
| CGA | GTC | CAC | GGC | ATC | GTC | TTT | GAG | 288 |
| GAC | AAC | GTG | GAC | ACT | GAG | GCC | GTG | 312 |
| GCT | CAG | CTG | CTG | GAT | TTC | GTC | TCC | 336 |
| TCT | CAG | ACC | CAC | GTG | CCC | ATC | CTC | 360 |
| AGC | ATC | AGT | GGA | GGT | TCT | GCT | GTG | 384 |
| GTC | CTC | ACC | CCC | AAG | GAG | CCA | GGC | 408 |
| TCC | GCC | TTT | CTA | CAG | CTG | GGC | GTG | 432 |
| TCC | CTG | GAG | CAG | CAG | CTG | CAG | GTG | 456 |
| CTG | TTC | AAG | GTG | CTG | GAG | GAA | TAC | 480 |
| GAC | TGG | AGC | GCG | TTC | GCT | GTC | ATC | 504 |
| ACC | AGC | CTG | CAC | CCG | GGC | CAC | GCG | 528 |
| CTC | TTC | CTC | GAG | GGC | GTG | CGC | GCC | 552 |
| GTC | GCC | GAC | GCC | AGC | TAC | CTG | AGC | 576 |
| TGG | CGG | CTG | CTG | GAC | GTG | CTC | ACG | 600 |
| CTG | GAG | CTG | GGC | CCC | GGT | GGG | CCG | 624 |
| CGA | GCG | CGC | ACT | CAG | CGC | TTA | CTG | 648 |
| CGC | CAG | GTC | GAC | GCC | CCG | GTG | CTG | 672 |

| GTG | GCC | TAC | TGC | TCC | CGT | GAA | GAG | 696 |
| GCG | GAG | GTG | CTC | TTC | GCG | GAG | GCT | 720 |
| GCA | CAG | GCT | GGC | TTG | GTG | GGA | CCC | 744 |
| GGT | CAC | GTG | TGG | TTA | GTA | CCT | AAT | 768 |
| CTG | GCG | CTG | GGA | AGC | ACC | GAC | GCT | 792 |
| CCC | CCT | GCA | GCC | TTC | CCA | GTG | GGC | 816 |
| CTC | ATC | AGT | GTG | GTC | ACC | GAG | AGT | 840 |
| TGG | CGC | CTT | AGC | CTA | CGC | CAG | AAA | 864 |
| GTC | CGC | GAC | GGT | GTA | GCC | ATT | CTG | 888 |
| GCC | CTC | GGT | GCC | CAC | AGC | TAC | CGA | 912 |
| CGC | CAG | TAC | GGT | ACC | CTT | CCA | GCC | 936 |
| CCG | GCT | GGA | GAC | TGC | CGA | AGC | CAC | 960 |
| CCA | GGA | CCC | GTC | AGC | CCT | GCC | AGG | 984 |
| GAG | GCT | TTC | TAC | AGG | CAT | CTG | CTG | 1008 |
| AAT | GTC | ACC | TGG | GAA | GGC | CGA | GAC | 1032 |
| TTC | TCT | TTT | AGC | CCT | GGT | GGG | TAC | 1056 |
| CTG | GTC | CAG | CCC | ACA | ATG | GTT | GTG | 1080 |
| ATC | GCT | CTC | AAC | CGG | CAT | CGC | CTC | 1104 |
| TGG | GAG | ATG | GTG | GGA | CGG | TGG | GAT | 1128 |
| CAT | GGG | GTC | CTG | TAC | ATG | AAG | TAT | 1152 |
| CCA | GTA | TGG | CCT | CGC | TAC | AGC | ACT | 1176 |
| TCT | CTG | CAG | CCT | GTG | GTG | GAC | AGC | 1200 |
| CGG | CAC | CTG | ACA | GTG | GCC | ACA | CTG | 1224 |
| GAA | GAA | AGG | CCT | TTT | GTC | ATT | GTG | 1248 |
| GAG | AGC | CCT | GAC | CCT | GGC | ACA | GGT | 1272 |
| GGC | TGT | GTT | CCC | AAC | ACT | GTG | CCC | 1296 |
| TGC | CGT | AGA | CAG | AGC | AAC | CAC | ACC | 1320 |
| TTC | AGC | AGC | GGG | GAT | ATA | ACC | CCC | 1344 |
| TAC | ACC | AAG | CTC | TGT | TGT | AAG | GGC | 1368 |
| TTC | TGC | ATC | GAC | ATC | CTC | AAG | AAG | 1392 |
| CTG | GCC | AAG | GTG | GTC | AAG | TTC | TCC | 1416 |
| TAC | GAC | TTG | TAC | CTG | GTG | ACC | AAC | 1440 |
| GGC | AAG | CAC | GGC | AAG | AGG | GTT | CGT | 1464 |
| GGT | GTG | TGG | AAT | GGT | ATG | ATC | GGT | 1488 |
| GAG | GTA | TAC | TAC | AAG | CGG | GCA | GAC | 1512 |
| ATG | GCC | ATC | GGC | TCC | CTC | ACC | ATC | 1536 |
| AAT | GAA | GAG | CGC | TCA | GAG | ATT | ATA | 1560 |
| GAC | TTC | TCT | GTG | CCT | TTT | GTG | GAG | 1584 |
| ACC | GGC | ATC | AGT | GTG | ATG | GTG | GCA | 1608 |
| AGG | AGC | AAC | GGC | ACC | GTC | TCC | CCC | 1632 |

-continued

| | | | | | | | |
|---|---|---|---|---|---|---|---|
| TCG | GCT | TTT | CTG | GAG | CCC | TAC | AGC | 1656 |
| CCT | GCC | GTG | TGG | GTG | ATG | ATG | TTT | 1680 |
| GTA | ATG | TGC | CTC | ACG | GTG | GTT | GCC | 1704 |
| ATC | ACT | GTC | TTC | ATG | TTC | GAG | TAT | 1728 |
| TTC | AGC | CCT | GTC | AGC | TAC | AAC | CAG | 1752 |
| AAT | CTC | ACC | AAG | GGC | AAG | AAG | TCA | 1776 |
| GGT | GGA | CCA | TCC | TTC | ACC | ATT | GGC | 1800 |
| AAG | TCC | GTG | TGG | TTG | CTG | TGG | GCA | 1824 |
| CTG | GTC | TTC | AAC | AAC | TCT | GTT | CCC | 1848 |
| ATC | GAG | AAC | CCC | CGG | GGC | ACC | ACC | 1872 |
| AGC | AAG | ATC | ATG | GTC | CTG | GTG | TGG | 1896 |
| GCC | TTC | TTC | GCT | GTC | ATC | TTC | CTC | 1920 |
| GCT | AGC | TAC | ACG | GCC | AAT | CTG | GCA | 1944 |
| GCC | TTC | ATG | ATC | CAG | GAA | CAA | TAC | 1968 |
| ATC | GAC | ACT | GTG | TCG | GGC | CTT | AGT | 1992 |
| GAC | AAG | AAG | TTT | CAG | CGG | CCT | CAA | 2016 |
| GAC | CAA | TAC | CCA | CCC | TTC | CGT | TTT | 2040 |
| GGC | ACG | GTA | CCT | AAT | GGC | AGC | ACA | 2064 |
| GAG | AGG | AAC | ATT | CGT | AGC | AAC | TAT | 2088 |
| CGT | GAC | ATG | CAC | ACT | CAC | ATG | GTC | 2112 |
| AAG | TTC | AAC | CAG | CGC | TCG | GTG | GAG | 2136 |
| GAT | GCT | CTC | ACA | AGC | CTG | AAG | ATG | 2160 |
| GGG | AAG | CTG | GAC | GCC | TTC | ATC | TAT | 2184 |
| GAT | GCC | GCC | GTC | CTC | AAC | TAC | ATG | 2208 |
| GCG | GGC | AAG | GAC | GAA | GGC | TGC | AAG | 2232 |
| CTG | GTC | ACC | ATT | GGG | TCT | GGC | AAA | 2256 |
| GTC | TTT | GCC | ACC | ACT | GGC | TAT | GGC | 2280 |
| ATT | GCC | ATG | CAG | AAA | GAC | TCC | CAC | 2304 |
| TGG | AAG | CGG | GCC | ATA | GAC | CTG | GCG | 2328 |
| CTC | CTG | CAG | TTC | CTG | GGG | GAT | GGG | 2352 |
| GAG | ACA | CAG | AAG | TTG | GAG | ACA | GTG | 2376 |
| TGG | CTC | TCA | GGG | ATC | TGC | CAT | AAC | 2400 |
| GAG | AAG | AAC | GAG | GTG | ATG | AGC | AGC | 2424 |
| AAG | CTG | GAC | ATT | GAC | AAC | ATG | GCG | 2448 |
| GGC | GTC | TTC | TAC | ATG | CTG | TTG | GTG | 2472 |
| GCC | ATG | GGG | CTG | GCC | CTT | CTG | GTC | 2496 |
| TTT | GCC | TGG | GAG | CAC | CTG | GTC | TAC | 2520 |
| TGG | AAA | CTT | CGA | CAC | TCA | GTG | CCC | 2544 |
| AGC | TCA | TCC | CAG | CTG | GAC | TTC | CTG | 2568 |
| CTG | GCT | TTC | AGC | AGG | GGC | ATC | TAC | 2592 |

| AGC | TGC | TTC | AAC | GGG | GTA | CAG | AGC | 2616 |
| CTT | CCG | AGC | CCT | GCG | CGG | CCG | CCC | 2640 |
| AGC | CCG | GAC | CTT | ACA | GCA | GGC | TCA | 2664 |
| GCC | CAG | GCC | AAT | GTG | CTG | AAG | ATG | 2688 |
| CTG | CAG | GCG | GCT | CGA | GAC | ATG | GTG | 2712 |
| AGC | ACA | GCG | GAC | GTG | AGC | GGC | TCT | 2736 |
| TTG | GAC | CGC | GCC | ACT | CGT | ACC | ATC | 2760 |
| GAG | AAC | TGG | GGC | AAC | AAT | CGC | CGC | 2784 |
| GCG | CCT | GCT | CCC | ACC | ACC | TCC | GGC | 2808 |
| CCG | CGG | TCA | TGC | ACC | CCG | GGT | CCT | 2832 |
| CCG | GGA | CAA | CCG | AGT | CCC | AGC | GGC | 2856 |
| TGG | CGG | CCT | CCC | GGT | GGG | GGC | CGC | 2880 |
| ACC | CCG | CTA | GCG | CGC | CGG | GCC | CCG | 2904 |
| CAG | CCT | CCC | GCT | CGC | CCC | GGA | CCT | 2928 |
| GCG | CAG | GGT | CGC | CTC | AGC | CCG | ACG | 2952 |
| TGT | CCC | GAG | CAT | CCT | GCA | GGC | ACG | 2976 |
| CTT | GGG | ATG | CGC | GGT | GGC | CAG | TGC | 3000 |
| GAG | TCG | GGC | ATC | AGG | GAT | CGC | ACC | 3024 |
| TCT | CGG | CCT | CCG | GAG | CGG | CGC | GCG | 3048 |
| CTC | CCG | GAG | CGC | TCC | CTG | TTG | CAC | 3072 |
| GCG | CAC | TGC | CAC | TAC | AGT | TCC | TTC | 3096 |
| CCT | CGA | GCA | GAG | AGG | TCA | GGG | CGC | 3120 |
| CCA | TTT | CTC | CCG | CTA | TTC | CCG | GAG | 3144 |
| CCC | CCG | GAG | CCC | GAC | GAC | CTG | CCG | 3168 |
| CTG | CTC | GGG | CCG | GAA | CAG | CTG | GCT | 3192 |
| CGG | CGG | GAG | GCT | CTG | CTG | CGC | GCG | 3216 |
| GCC | TGG | GCC | AGG | GGC | CCG | CGC | CCT | 3240 |
| CGG | CAC | GCT | TCC | CTG | CCC | AGC | TCC | 3264 |
| GTG | GCA | GAA | GCC | TTC | ACT | CGA | TCC | 3288 |
| AAC | CCT | CTG | CCT | GCC | AGG | TGT | ACC | 3312 |
| GGT | CAC | GCC | TGC | GCT | TGC | CCA | TGT | 3336 |
| CCC | CAA | AGC | CGG | CCA | TCC | TGC | CGG | 3360 |
| CAC | GTG | GCT | CAA | ACA | CAG | TCG | TTG | 3384 |
| CGG | CTG | CCA | TCC | TAC | CGG | GAG | GCC | 3408 |
| TGT | GTG | GAG | GGC | GTG | CCA | GCA | GGG | 3432 |
| GTG | GCC | GCC | ACC | TGG | CAG | CCC | AGA | 3456 |
| CAG | CAT | GTC | TGC | CTG | CAC | ACC | CAT | 3480 |
| ACC | CAC | CTG | CCG | TTC | TGC | TGG | GGG | 3504 |
| ACT | GTC | TGC | CGT | CAC | CCT | CCA | CCC | 3528 |
| TGT | TCC | AGC | CAC | AGT | CCC | TGG | CTC | 3552 |

```
ATT   GGA   ACT   TGG   GAG   CCT   CCA   TCA         3576

CAC   AGA   GGC   AGG   ACC   CTG   GGG   CTA         3600

GGT   ACA   GGC   TAC   AGG   GAC   AGT   GGG         3624

GTG   CTA   GAA   GAG   GTC   AGC   AGG   GAA         3648

GCT   TGT   GGG   ACA   CAA   GGG   TTT   CCA         3672

AGG   TCC   TGC   ACC   TGG   AGG   CGG   ATC         3696

TCC   AGC   CTG   GAA   TCA   GAA   GTG               3717
```

( 2 ) INFORMATION FOR SEQ ID NO: 8:

( i ) SEQUENCE CHARACTERISTICS:
        ( A ) LENGTH: 1456 amino acids
        ( B ) TYPE: amino acid
        ( C ) STRANDEDNESS: single strand
        ( D ) TOPOLOGY: linear ( i i ) MOLECULE TYPE: protein ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:8: FROM 1 to 4368

( x i ) SEQUENCE DESCRIPTION: SEQ ID NO:8:

```
Arg   Ser   Gln   Lys   Ser   Ala   Pro   Ser   Ile   Gly   Ile   Ala   Val   Ile   Leu   Val
 1                       5                           10                          15

Gly   Thr   Ser   Asp   Glu   Val   Ala   Ile   Lys   Asp   Ala   His   Glu   Lys   Asp   Asp
                  20                          25                          30

Phe   His   His   Leu   Ser   Val   Val   Pro   Arg   Val   Glu   Leu   Val   Ala   Met   Asn
            35                          40                          45

Glu   Thr   Asp   Pro   Lys   Ser   Ile   Ile   Thr   Arg   Ile   Cys   Asp   Leu   Met   Ser
      50                          55                          60

Asp   Arg   Lys   Ile   Gln   Gly   Val   Val   Leu   Ala   Asp   Asp   Thr   Asp   Gln   Glu
65                          70                          75                          80

Ala   Ile   Ala   Gln   Ile   Leu   Asp   Phe   Ile   Ser   Ala   Gln   Thr   Leu   Thr   Pro
                        85                          90                          95

Ile   Leu   Gly   Ile   His   Gly   Gly   Ser   Ser   Met   Ile   Met   Ala   Asp   Lys   Asp
                  100                         105                         110

Glu   Ser   Ser   Met   Phe   Phe   Gln   Phe   Gly   Pro   Ser   Ile   Glu   Gln   Gln   Ala
            115                         120                         125

Ser   Val   Met   Leu   Asn   Ile   Met   Glu   Glu   Tyr   Asp   Trp   Tyr   Ile   Phe   Ser
      130                         135                         140

Ile   Val   Thr   Thr   Tyr   Phe   Pro   Gly   Tyr   Gln   Asp   Phe   Val   Asn   Lys   Ile
145                         150                         155                         160

Arg   Ser   Thr   Ile   Glu   Asn   Ser   Phe   Val   Gly   Trp   Glu   Leu   Glu   Glu   Val
                        165                         170                         175

Leu   Leu   Leu   Asp   Met   Ser   Leu   Asp   Asp   Gly   Asp   Ser   Lys   Ile   Gln   Asn
                  180                         185                         190

Gln   Leu   Lys   Lys   Leu   Gln   Ser   Pro   Ile   Ile   Leu   Leu   Tyr   Cys   Thr   Lys
            195                         200                         205

Glu   Glu   Ala   Thr   Tyr   Ile   Phe   Glu   Val   Ala   Asn   Ser   Val   Gly   Leu   Thr
      210                         215                         220

Gly   Tyr   Gly   Tyr   Thr   Trp   Ile   Val   Pro   Ser   Leu   Val   Ala   Gly   Asp   Thr
225                         230                         235                         240
```

```
Asp Thr Val Pro Ser Glu Phe Pro Thr Gly Leu Ile Ser Val Ser Tyr
            245                 250                 255
Asp Glu Trp Asp Tyr Gly Leu Pro Ala Arg Val Arg Asp Gly Ile Ala
            260                 265                 270
Ile Ile Thr Thr Ala Ala Ser Asp Met Leu Ser Glu His Ser Phe Ile
            275                 280                 285
Pro Glu Pro Lys Ser Ser Cys Tyr Asn Thr His Glu Lys Arg Ile Tyr
            290                 295                 300
Gln Ser Asn Met Leu Asn Arg Tyr Leu Ile Asn Val Thr Phe Glu Gly
305                 310                 315                 320
Arg Asn Leu Ser Phe Ser Glu Asp Gly Tyr Gln Met His Pro Lys Leu
                    325                 330                 335
Val Ile Ile Leu Leu Asn Lys Glu Arg Lys Trp Glu Arg Val Gly Lys
            340                 345                 350
Trp Lys Asp Lys Ser Leu Gln Met Lys Tyr Tyr Val Trp Pro Arg Met
            355                 360                 365
Cys Pro Glu Thr Glu Glu Gln Glu Asp Asp His Leu Ser Ile Val Thr
        370                 375                 380
Leu Glu Glu Ala Pro Phe Val Ile Val Glu Ser Val Asp Pro Leu Ser
385                 390                 395                 400
Gly Thr Cys Met Arg Asn Thr Val Pro Cys Gln Lys Arg Ile Ile Ser
                405                 410                 415
Glu Asn Lys Thr Asp Glu Glu Pro Gly Tyr Ile Lys Lys Cys Cys Lys
            420                 425                 430
Gly Phe Cys Ile Asp Ile Leu Lys Lys Ile Ser Lys Ser Val Lys Phe
            435                 440                 445
Thr Tyr Asp Leu Tyr Leu Val Thr Asn Gly Lys His Gly Lys Lys Ile
        450                 455                 460
Asn Gly Thr Trp Asn Gly Met Ile Gly Glu Val Val Met Lys Arg Ala
465                 470                 475                 480
Tyr Met Ala Val Gly Ser Leu Thr Ile Asn Glu Glu Arg Ser Glu Val
                485                 490                 495
Val Asp Phe Ser Val Pro Phe Ile Glu Thr Gly Ile Ser Val Met Val
            500                 505                 510
Ser Arg Ser Asn Gly Thr Val Ser Pro Ser Ala Phe Leu Glu Pro Phe
            515                 520                 525
Ser Ala Asp Val Trp Val Met Met Phe Val Met Leu Leu Ile Val Ser
        530                 535                 540
Ala Val Ala Val Phe Val Phe Glu Tyr Phe Ser Pro Val Gly Tyr Asn
545                 550                 555                 560
Arg Cys Leu Ala Asp Gly Arg Glu Pro Gly Gly Pro Ser Phe Thr Ile
                565                 570                 575
Gly Lys Ala Ile Trp Leu Leu Trp Gly Leu Val Phe Gln Asn Ser Val
            580                 585                 590
Pro Val Gln Asn Pro Lys Gly Thr Thr Ser Lys Ile Met Val Ser Val
        595                 600                 605
Trp Ala Phe Phe Ala Val Ile Phe Leu Ala Ser Tyr Thr Ala Asn Leu
610                 615                 620
Ala Ala Phe Met Ile Gln Glu Glu Tyr Val Asp Gln Val Ser Gly Leu
625                 630                 635                 640
Ser Asp Lys Lys Phe Gln Arg Pro Asn Asp Phe Ser Pro Pro Phe Arg
                645                 650                 655
Phe Gly Thr Val Pro Asn Gly Ser Thr Glu Arg Asn Ile Arg Asn Asn
```

```
                            660                      665                      670
Tyr  Ala  Glu  Met  His  Ala  Tyr  Met  Gly  Lys  Phe  Asn  Gln  Arg  Gly  Val
          675                      680                      685

Asp  Asp  Ala  Leu  Leu  Ser  Leu  Lys  Thr  Gly  Lys  Leu  Asp  Ala  Phe  Ile
     690                      695                      700

Tyr  Asp  Ala  Ala  Val  Leu  Asn  Tyr  Met  Ala  Gly  Arg  Asp  Glu  Gly  Cys
705                      710                      715                      720

Lys  Leu  Val  Thr  Ile  Gly  Ser  Gly  Lys  Val  Phe  Ala  Ser  Thr  Gly  Tyr
                    725                      730                      735

Gly  Ile  Ala  Ile  Gln  Lys  Asp  Ser  Gly  Trp  Lys  Arg  Gln  Val  Asp  Leu
               740                      745                      750

Ala  Ile  Leu  Gln  Leu  Phe  Gly  Asp  Gly  Glu  Met  Glu  Glu  Leu  Glu  Ala
               755                      760                      765

Leu  Trp  Leu  Thr  Gly  Ile  Cys  His  Asn  Glu  Lys  Asn  Glu  Val  Met  Ser
770                      775                      780

Ser  Gln  Leu  Asp  Ile  Asp  Asn  Met  Ala  Gly  Val  Phe  Tyr  Met  Leu  Gly
785                      790                      795                      800

Ala  Ala  Met  Ala  Leu  Ser  Leu  Ile  Thr  Phe  Ile  Cys  Glu  His  Leu  Phe
               805                      810                      815

Tyr  Trp  Gln  Phe  Arg  His  Cys  Phe  Met  Gly  Val  Cys  Ser  Gly  Lys  Pro
               820                      825                      830

Gly  Met  Val  Phe  Ser  Ile  Ser  Arg  Gly  Ile  Tyr  Ser  Cys  Ile  His  Gly
          835                      840                      845

Val  Ala  Ile  Glu  Glu  Arg  Gln  Ser  Val  Met  Asn  Ser  Pro  Thr  Ala  Thr
     850                      855                      860

Met  Asn  Asn  Thr  His  Ser  Asn  Ile  Leu  Arg  Leu  Leu  Arg  Thr  Ala  Lys
865                      870                      875                      880

Asn  Met  Ala  Asn  Leu  Ser  Gly  Val  Asn  Gly  Ser  Pro  Gln  Ser  Ala  Leu
                    885                      890                      895

Asp  Phe  Ile  Arg  Arg  Glu  Ser  Ser  Val  Tyr  Asp  Ile  Ser  Glu  His  Arg
               900                      905                      910

Arg  Ser  Phe  Thr  His  Ser  Asp  Cys  Lys  Ser  Tyr  Asn  Asn  Pro  Pro  Cys
               915                      920                      925

Glu  Glu  Asn  Leu  Phe  Ser  Asp  Tyr  Ile  Ser  Glu  Val  Glu  Arg  Thr  Phe
930                      935                      940

Gly  Asn  Leu  Gln  Leu  Lys  Asp  Ser  Asn  Val  Tyr  Gln  Asp  His  Tyr  His
945                      950                      955                      960

His  His  His  Arg  Pro  His  Ser  Ile  Gly  Ser  Thr  Ser  Ser  Ile  Asp  Gly
               965                      970                      975

Leu  Tyr  Asp  Cys  Asp  Asn  Pro  Pro  Phe  Thr  Thr  Gln  Pro  Arg  Ser  Ile
               980                      985                      990

Ser  Lys  Lys  Pro  Leu  Asp  Ile  Gly  Leu  Pro  Ser  Ser  Lys  His  Ser  Gln
          995                      1000                     1005

Leu  Ser  Asp  Leu  Tyr  Gly  Lys  Phe  Ser  Phe  Lys  Ser  Asp  Arg  Tyr  Ser
     1010                     1015                     1020

Gly  His  Asp  Asp  Leu  Ile  Arg  Ser  Asp  Val  Ser  Asp  Ile  Ser  Thr  His
1025                     1030                     1035                     1040

Thr  Val  Thr  Tyr  Gly  Asn  Ile  Glu  Gly  Asn  Ala  Ala  Lys  Arg  Arg  Lys
               1045                     1050                     1055

Gln  Gln  Tyr  Lys  Asp  Ser  Leu  Lys  Lys  Arg  Pro  Ala  Ser  Ala  Lys  Ser
               1060                     1065                     1070

Arg  Arg  Glu  Phe  Asp  Glu  Ile  Glu  Leu  Ala  Tyr  Arg  Arg  Arg  Pro  Pro
               1075                     1080                     1085
```

```
Arg  Ser  Pro  Asp  His  Lys  Arg  Tyr  Phe  Arg  Asp  Lys  Glu  Gly  Leu  Arg
     1090                1095                1100

Asp  Phe  Tyr  Leu  Asp  Gln  Phe  Arg  Thr  Lys  Glu  Asn  Ser  Pro  His  Trp
1105                1110                1115                               1120

Glu  His  Val  Asp  Leu  Thr  Asp  Ile  Tyr  Lys  Glu  Arg  Ser  Cys  Asp  Phe
               1125                1130                          1135

Lys  Arg  Asp  Ser  Val  Ser  Gly  Gly  Pro  Cys  Thr  Asn  Arg  Ser  His
          1140                1145                          1150

Leu  Lys  His  Gly  Thr  Gly  Asp  Lys  His  Gly  Val  Val  Gly  Gly  Val  Pro
     1155                1160                1165

Ala  Pro  Trp  Glu  Lys  Asn  Leu  Thr  Asn  Val  Asp  Trp  Glu  Asp  Arg  Ser
     1170                1175                1180

Gly  Gly  Asn  Phe  Cys  Arg  Ser  Cys  Pro  Ser  Lys  Leu  His  Asn  Tyr  Ser
1185                1190                     1195                          1200

Ser  Thr  Val  Ala  Gly  Gln  Asn  Ser  Gly  Arg  Gln  Ala  Cys  Ile  Arg  Cys
                    1205                1210                     1215

Glu  Ala  Cys  Lys  Lys  Ala  Gly  Asn  Leu  Tyr  Asp  Ile  Ser  Glu  Asp  Asn
               1220                1225                     1230

Ser  Leu  Gln  Glu  Leu  Asp  Gln  Pro  Ala  Ala  Pro  Val  Ala  Val  Ser  Ser
          1235                1240                     1245

Asn  Ala  Ser  Thr  Thr  Lys  Tyr  Pro  Gln  Ser  Pro  Thr  Asn  Ser  Lys  Ala
     1250                1255                1260

Gln  Lys  Lys  Asn  Arg  Asn  Lys  Leu  Arg  Arg  Gln  His  Ser  Tyr  Asp  Thr
1265                1270                1275                               1280

Phe  Val  Asp  Leu  Gln  Lys  Glu  Glu  Ala  Ala  Leu  Ala  Pro  Arg  Ser  Val
               1285                1290                     1295

Ser  Leu  Lys  Asp  Lys  Gly  Arg  Phe  Met  Asp  Gly  Ser  Pro  Tyr  Ala  His
               1300                1305                     1310

Met  Phe  Glu  Met  Pro  Ala  Gly  Glu  Ser  Ser  Phe  Ala  Asn  Lys  Ser  Ser
     1315                1320                     1325

Val  Thr  Thr  Ala  Gly  His  His  His  Asn  Asn  Pro  Gly  Ser  Gly  Tyr  Met
     1330                1335                     1340

Leu  Ser  Lys  Ser  Leu  Tyr  Pro  Asp  Arg  Val  Thr  Gln  Asn  Pro  Phe  Ile
1345                1350                1355                               1360

Pro  Thr  Phe  Gly  Asp  Asp  Gln  Cys  Leu  Leu  Thr  Ala  Ala  Asn  Pro  Thr
               1365                1370                     1375

Ser  Ser  Gly  Ser  Pro  Thr  Val  Ala  Gly  Ala  Ser  Lys  Thr  Arg  Pro  Asp
          1380                1385                     1390

Phe  Arg  Ala  Leu  Val  Thr  Asn  Lys  Pro  Val  Val  Ser  Ala  Leu  His  Gly
          1395                1400                     1405

Ala  Val  Pro  Gly  Arg  Phe  Gln  Lys  Asp  Ile  Cys  Ile  Gly  Asn  Gln  Ser
     1410                1415                1420

Asn  Pro  Cys  Val  Pro  Asn  Asn  Lys  Asn  Pro  Arg  Ala  Phe  Asn  Gly  Ser
1425                1430                1435                               1440

Ser  Asn  Gly  His  Val  Tyr  Glu  Lys  Leu  Ser  Ser  Ile  Glu  Ser  Asp  Val
                    1445                1450                     1455
```

( 2 ) INFORMATION FOR SEQ ID NO: 9:

( i ) SEQUENCE CHARACTERISTICS:
        ( A ) LENGTH: 920 amino acids
        ( B ) TYPE: amino acid
        ( C ) STRANDEDNESS: single strand
        ( D ) TOPOLOGY: linear ( i i ) MOLECULE TYPE: protein ( v i ) ORIGINAL SOURCE:
    ( A ) ORGANISM: mouse
    ( F ) TISSUE TYPE: brain ( x ) PUBLICATION INFORMATION:
    ( A ) AUTHORS: Masayoshi MISHINA
    ( B ) TITLE: NOVEL PROTEINS AND GENES CODING THE SAME
    ( K ) RELEVANT RESIDUES IN SEQ ID NO:9: FROM 1 to 920

( x i ) SEQUENCE DESCRIPTION: SEQ ID NO:9:

```
Arg  Ala  Ala  Cys  Asp  Pro  Lys  Ile  Val  Asn  Ile  Gly  Ala  Val  Leu  Ser
 1              5                    10                            15

Thr  Arg  Lys  His  Glu  Gln  Met  Phe  Arg  Glu  Ala  Val  Asn  Gln  Ala  Asn
               20                    25                       30

Lys  Arg  His  Gly  Ser  Trp  Lys  Ile  Gln  Leu  Asn  Ala  Thr  Ser  Val  Thr
          35                        40                       45

His  Lys  Pro  Asn  Ala  Ile  Gln  Met  Ala  Leu  Ser  Val  Cys  Glu  Asp  Leu
     50                        55                  60

Ile  Ser  Ser  Gln  Val  Tyr  Ala  Ile  Leu  Val  Ser  His  Pro  Pro  Thr  Pro
65                       70                  75                           80

Asn  Asp  His  Phe  Thr  Pro  Thr  Pro  Val  Ser  Tyr  Thr  Ala  Gly  Phe  Tyr
                    85                       90                            95

Arg  Ile  Pro  Val  Leu  Gly  Leu  Thr  Thr  Arg  Met  Ser  Ile  Tyr  Ser  Asp
               100                      105                 110

Lys  Ser  Ile  His  Leu  Ser  Phe  Leu  Arg  Thr  Val  Pro  Pro  Tyr  Ser  His
          115                      120                 125

Gln  Ser  Ser  Val  Trp  Phe  Glu  Met  Met  Arg  Val  Tyr  Asn  Trp  Asn  His
     130                      135                      140

Ile  Ile  Leu  Leu  Val  Ser  Asp  Asp  His  Glu  Gly  Arg  Ala  Ala  Gln  Lys
145                      150                 155                          160

Arg  Leu  Glu  Thr  Leu  Leu  Glu  Glu  Arg  Glu  Ser  Lys  Ala  Glu  Lys  Val
                    165                      170                 175

Leu  Gln  Phe  Asp  Pro  Gly  Thr  Lys  Asn  Val  Thr  Ala  Leu  Leu  Met  Glu
               180                      185                 190

Ala  Arg  Asp  Leu  Glu  Ala  Arg  Val  Ile  Ile  Leu  Ser  Ala  Ser  Glu  Asp
     195                      200                 205

Asp  Ala  Ala  Thr  Val  Tyr  Arg  Ala  Ala  Ala  Met  Leu  Asn  Met  Thr  Gly
210                      215                      220

Ser  Gly  Tyr  Val  Trp  Leu  Val  Gly  Glu  Arg  Glu  Ile  Ser  Gly  Asn  Ala
225                      230                      235                     240

Leu  Arg  Tyr  Ala  Pro  Asp  Gly  Ile  Ile  Gly  Leu  Gln  Leu  Ile  Asn  Gly
                    245                      250                 255

Lys  Asn  Glu  Ser  Ala  His  Ile  Ser  Asp  Ala  Val  Gly  Val  Val  Ala  Gln
               260                      265                 270

Ala  Val  His  Glu  Leu  Leu  Glu  Lys  Glu  Asn  Ile  Thr  Asp  Pro  Pro  Arg
          275                      280                 285

Gly  Cys  Val  Gly  Asn  Thr  Asn  Ile  Trp  Lys  Thr  Gly  Pro  Leu  Phe  Lys
     290                      295                 300

Arg  Val  Leu  Met  Ser  Ser  Lys  Tyr  Ala  Asp  Gly  Val  Thr  Gly  Arg  Val
305                      310                      315                     320

Glu  Phe  Asn  Glu  Asp  Gly  Asp  Arg  Lys  Phe  Ala  Asn  Tyr  Ser  Ile  Met
                    325                      330                 335

Asn  Leu  Gln  Asn  Arg  Lys  Leu  Val  Gln  Val  Gly  Ile  Tyr  Asn  Gly  Thr
               340                      345                 350

His  Val  Ile  Pro  Asn  Asp  Arg  Lys  Ile  Ile  Trp  Pro  Gly  Gly  Glu  Thr
          355                      360                 365
```

```
Glu Lys Pro Arg Gly Tyr Gln Met Ser Thr Arg Leu Lys Ile Val Thr
370                 375                 380
Ile His Gln Glu Pro Phe Val Tyr Val Lys Pro Thr Met Ser Asp Gly
385                 390                 395                 400
Thr Cys Lys Glu Glu Phe Thr Val Asn Gly Asp Pro Val Lys Lys Val
                405                 410                 415
Ile Cys Thr Gly Pro Asn Asp Thr Ser Pro Gly Ser Pro Arg His Thr
            420                 425                 430
Val Pro Gln Cys Cys Tyr Gly Phe Cys Val Asp Leu Leu Ile Lys Leu
        435                 440                 445
Ala Arg Thr Met Asn Phe Thr Tyr Glu Val His Leu Val Ala Asp Gly
    450                 455                 460
Lys Phe Gly Thr Gln Glu Arg Val Asn Asn Ser Asn Lys Lys Glu Trp
465                 470                 475                 480
Asn Gly Met Met Gly Glu Leu Leu Ser Gly Gln Ala Asp Met Ile Val
                485                 490                 495
Ala Pro Leu Thr Ile Asn Asn Glu Arg Ala Gln Tyr Ile Glu Phe Ser
            500                 505                 510
Lys Pro Phe Lys Tyr Gln Gly Leu Thr Ile Leu Val Lys Lys Glu Ile
        515                 520                 525
Pro Arg Ser Thr Leu Asp Ser Phe Met Gln Pro Phe Gln Ser Thr Leu
    530                 535                 540
Trp Leu Leu Val Gly Leu Ser Val His Val Val Ala Val Met Leu Tyr
545                 550                 555                 560
Leu Leu Asp Arg Phe Ser Pro Phe Gly Arg Phe Lys Val Asn Ser Glu
                565                 570                 575
Glu Glu Glu Glu Asp Ala Leu Thr Leu Ser Ser Ala Met Trp Phe Ser
            580                 585                 590
Trp Gly Val Leu Leu Gln Ser Gly Ile Gly Glu Gly Ala Pro Arg Ser
        595                 600                 605
Phe Ser Ala Arg Ile Leu Gly Met Val Trp Ala Gly Phe Ala Met Ile
    610                 615                 620
Ile Val Ala Ser Tyr Thr Ala Asn Leu Ala Ala Phe Leu Val Leu Asp
625                 630                 635                 640
Arg Pro Glu Glu Arg Ile Thr Gly Ile Asn Asp Pro Arg Leu Arg Asn
                645                 650                 655
Pro Ser Asp Lys Phe Ile Tyr Ala Thr Val Lys Gln Ser Ser Val Asp
            660                 665                 670
Ile Tyr Phe Arg Arg Gln Val Glu Leu Ser Thr Met Tyr Arg His Met
        675                 680                 685
Glu Lys His Asn Tyr Glu Ser Ala Ala Glu Ala Ile Gln Ala Val Arg
690                 695                 700
Asp Asn Lys Leu His Ala Phe Ile Trp Asp Ser Ala Val Leu Glu Phe
705                 710                 715                 720
Glu Ala Ser Gln Lys Cys Asp Leu Val Thr Thr Gly Glu Leu Phe Phe
                725                 730                 735
Arg Ser Gly Phe Gly Ile Gly Met Arg Lys Asp Ser Pro Trp Lys Gln
            740                 745                 750
Asn Val Ser Leu Ser Ile Leu Lys Ser His Glu Asn Gly Phe Met Glu
        755                 760                 765
Asp Leu Asp Lys Thr Trp Val Arg Tyr Gln Glu Cys Asp Ser Arg Ser
    770                 775                 780
Asn Ala Pro Ala Thr Leu Thr Phe Glu Asn Met Ala Gly Val Phe Met
785                 790                 795                 800
```

| | | | | | | | | | | | | | |
|---|---|---|---|---|---|---|---|---|---|---|---|---|---|
| Leu | Val | Ala | Gly | Gly<br>805 | Ile | Val | Ala | Gly<br>810 | Ile | Phe | Leu | Ile | Phe<br>815 | Ile | Glu |

| Ile | Ala | Tyr | Lys<br>820 | Arg | His | Lys | Asp<br>825 | Ala | Arg | Arg | Lys<br>830 | Gln | Met | Gln | Leu |

| Ala | Phe | Ala<br>835 | Ala | Val | Asn | Val | Trp<br>840 | Arg | Lys | Asn | Leu<br>845 | Gln | Asp | Arg | Lys |

| Ser | Gly<br>850 | Arg | Ala | Glu | Pro | Asp<br>855 | Pro | Lys | Lys | Lys | Ala<br>860 | Thr | Phe | Arg | Ala |

| Ile<br>865 | Thr | Ser | Thr | Leu | Ala<br>870 | Ser | Ser | Phe | Lys | Arg<br>875 | Arg | Arg | Ser | Ser | Lys<br>880 |

| Asp | Thr | Ser | Thr | Gly<br>885 | Gly | Gly | Arg | Gly | Ala<br>890 | Leu | Gln | Asn | Gln | Lys<br>895 | Asp |

| Thr | Val | Leu | Pro<br>900 | Arg | Arg | Ala | Ile | Glu<br>905 | Arg | Glu | Glu | Gly | Gln<br>910 | Leu | Gln |

| Leu | Cys | Ser<br>915 | Arg | His | Arg | Glu | Ser<br>920 |

( 2 ) INFORMATION FOR SEQ ID NO: 10:

( i ) SEQUENCE CHARACTERISTICS:
        ( A ) LENGTH: 920 amino acids
        ( B ) TYPE: amino acid
        ( C ) STRANDEDNESS: single strand
        ( D ) TOPOLOGY: linear ( i i ) MOLECULE TYPE: protein ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:10: FROM 1 to 920

( x i ) SEQUENCE DESCRIPTION: SEQ ID NO:10:

| | | | | | | | | | | | | | | | |
|---|---|---|---|---|---|---|---|---|---|---|---|---|---|---|---|
| Arg<br>1 | Ala | Ala | Cys | Asp<br>5 | Pro | Lys | Ile | Val | Asn<br>10 | Ile | Gly | Ala | Val | Leu<br>15 | Ser |

| Thr | Arg | Lys | His<br>20 | Glu | Gln | Met | Phe | Arg<br>25 | Glu | Ala | Val | Asn | Gln<br>30 | Ala | Asn |

| Lys | Arg | His<br>35 | Gly | Ser | Trp | Lys | Ile<br>40 | Gln | Leu | Asn | Ala | Thr<br>45 | Ser | Val | Thr |

| His | Lys<br>50 | Pro | Asn | Ala | Ile | Gln<br>55 | Met | Ala | Leu | Ser | Val<br>60 | Cys | Glu | Asp | Leu |

| Ile<br>65 | Ser | Ser | Gln | Val | Tyr<br>70 | Ala | Ile | Leu | Val | Ser<br>75 | His | Pro | Pro | Thr | Pro<br>80 |

| Asn | Asp | His | Phe | Thr<br>85 | Pro | Thr | Pro | Val | Ser<br>90 | Tyr | Thr | Ala | Gly | Phe<br>95 | Tyr |

| Arg | Ile | Pro | Val<br>100 | Leu | Gly | Leu | Thr | Thr<br>105 | Arg | Met | Ser | Ile | Tyr<br>110 | Ser | Asp |

| Lys | Ser | Ile<br>115 | His | Leu | Ser | Phe | Leu<br>120 | Arg | Thr | Val | Pro | Pro<br>125 | Tyr | Ser | His |

| Gln | Ser<br>130 | Ser | Val | Trp | Phe | Glu<br>135 | Met | Met | Arg | Val | Tyr<br>140 | Asn | Trp | Asn | His |

| Ile<br>145 | Ile | Leu | Leu | Val | Ser<br>150 | Asp | Asp | His | Glu | Gly<br>155 | Arg | Ala | Ala | Gln | Lys<br>160 |

| Arg | Leu | Glu | Thr | Leu<br>165 | Leu | Glu | Glu | Arg | Glu<br>170 | Ser | Lys | Ala | Glu | Lys<br>175 | Val |

-continued

| | | | | | | | | | | | | | | |
|---|---|---|---|---|---|---|---|---|---|---|---|---|---|---|
| Leu | Gln | Phe | Asp 180 | Pro | Gly | Thr | Lys | Asn 185 | Val | Thr | Ala | Leu 190 | Leu | Met | Glu |
| Ala | Arg | Asp 195 | Leu | Glu | Ala | Arg | Val 200 | Ile | Ile | Leu | Ser | Ala 205 | Ser | Glu | Asp |
| Asp | Ala 210 | Ala | Thr | Val | Tyr | Arg 215 | Ala | Ala | Ala | Met | Leu 220 | Asn | Met | Thr | Gly |
| Ser 225 | Gly | Tyr | Val | Trp | Leu 230 | Val | Gly | Glu | Arg | Glu 235 | Ile | Ser | Gly | Asn | Ala 240 |
| Leu | Arg | Tyr | Ala | Pro 245 | Asp | Gly | Ile | Ile | Gly 250 | Leu | Gln | Leu | Ile | Asn 255 | Gly |
| Lys | Asn | Glu | Ser 260 | Ala | His | Ile | Ser | Asp 265 | Ala | Val | Gly | Val 270 | Val | Ala | Gln |
| Ala | Val | His 275 | Glu | Leu | Leu | Glu | Lys 280 | Glu | Asn | Ile | Thr | Asp 285 | Pro | Pro | Arg |
| Gly | Cys 290 | Val | Gly | Asn | Thr | Asn 295 | Ile | Trp | Lys | Thr | Gly 300 | Pro | Leu | Phe | Lys |
| Arg 305 | Val | Leu | Met | Ser | Ser 310 | Lys | Tyr | Ala | Asp | Gly 315 | Val | Thr | Gly | Arg | Val 320 |
| Glu | Phe | Asn | Glu | Asp 325 | Gly | Asp | Arg | Lys | Phe 330 | Ala | Asn | Tyr | Ser | Ile 335 | Met |
| Asn | Leu | Gln | Asn 340 | Arg | Lys | Leu | Val | Gln 345 | Val | Gly | Ile | Tyr | Asn 350 | Gly | Thr |
| His | Val | Ile 355 | Pro | Asn | Asp | Arg | Lys 360 | Ile | Ile | Trp | Pro | Gly 365 | Gly | Glu | Thr |
| Glu | Lys 370 | Pro | Arg | Gly | Tyr | Gln 375 | Met | Ser | Thr | Arg | Leu 380 | Lys | Ile | Val | Thr |
| Ile 385 | His | Gln | Glu | Pro | Phe 390 | Val | Tyr | Val | Lys | Pro 395 | Thr | Met | Ser | Asp | Gly 400 |
| Thr | Cys | Lys | Glu | Glu 405 | Phe | Thr | Val | Asn | Gly 410 | Asp | Pro | Val | Lys | Lys 415 | Val |
| Ile | Cys | Thr | Gly 420 | Pro | Asn | Asp | Thr | Ser 425 | Pro | Gly | Ser | Pro | Arg 430 | His | Thr |
| Val | Pro | Gln 435 | Cys | Cys | Tyr | Gly | Phe 440 | Cys | Val | Asp | Leu | Leu 445 | Ile | Lys | Leu |
| Ala | Arg 450 | Thr | Met | Asn | Phe | Thr 455 | Tyr | Glu | Val | His | Leu 460 | Val | Ala | Asp | Gly |
| Lys 465 | Phe | Gly | Thr | Gln | Glu 470 | Arg | Val | Asn | Asn | Ser 475 | Asn | Lys | Lys | Glu | Trp 480 |
| Asn | Gly | Met | Met | Gly 485 | Glu | Leu | Leu | Ser | Gly 490 | Gln | Ala | Asp | Met | Ile 495 | Val |
| Ala | Pro | Leu | Thr 500 | Ile | Asn | Asn | Glu | Arg 505 | Ala | Gln | Tyr | Ile | Glu 510 | Phe | Ser |
| Lys | Pro | Phe 515 | Lys | Tyr | Gln | Gly 520 | Leu | Thr | Ile | Leu | Val 525 | Lys | Lys | Glu | Ile |
| Pro | Arg 530 | Ser | Thr | Leu | Asp | Ser 535 | Phe | Met | Gln | Pro | Phe 540 | Gln | Ser | Thr | Leu |
| Trp 545 | Leu | Leu | Val | Gly | Leu 550 | Ser | Val | His | Val | Val 555 | Ala | Val | Met | Leu | Tyr 560 |
| Leu | Leu | Asp | Arg | Phe 565 | Ser | Pro | Phe | Gly | Arg 570 | Phe | Lys | Val | Asn | Ser 575 | Thr |
| Ser | Asp | Gln | Ser 580 | Asn | Ala | Leu | Thr | Leu 585 | Ser | Ser | Ala | Met | Trp 590 | Phe | Ser |
| Trp | Gly | Val 595 | Leu | Leu | Asn | Ser | Gly 600 | Ile | Gly | Glu | Gly | Ala 605 | Pro | Arg | Ser |

```
Phe Ser Ala Arg Ile Leu Gly Met Val Trp Ala Gly Phe Ala Met Ile
610                 615                 620

Ile Val Ala Ser Tyr Thr Ala Asn Leu Ala Ala Phe Leu Val Leu Asp
625                 630                 635                 640

Arg Pro Glu Glu Arg Ile Thr Gly Ile Asn Asp Pro Arg Leu Arg Asn
                645                 650                 655

Pro Ser Asp Lys Phe Ile Tyr Ala Thr Val Lys Gln Ser Ser Val Asp
            660                 665                 670

Ile Tyr Phe Arg Arg Gln Val Glu Leu Ser Thr Met Tyr Arg His Met
        675                 680                 685

Glu Lys His Asn Tyr Glu Ser Ala Ala Glu Ala Ile Gln Ala Val Arg
    690                 695                 700

Asp Asn Lys Leu His Ala Phe Ile Trp Asp Ser Ala Val Leu Glu Phe
705                 710                 715                 720

Glu Ala Ser Gln Lys Cys Asp Leu Val Thr Thr Gly Glu Leu Phe Phe
                725                 730                 735

Arg Ser Gly Phe Gly Ile Gly Met Arg Lys Asp Ser Pro Trp Lys Gln
            740                 745                 750

Asn Val Ser Leu Ser Ile Leu Lys Ser His Glu Asn Gly Phe Met Glu
        755                 760                 765

Asp Leu Asp Lys Thr Trp Val Arg Tyr Gln Glu Cys Asp Ser Arg Ser
770                 775                 780

Asn Ala Pro Ala Thr Leu Thr Phe Glu Asn Met Ala Gly Val Phe Met
785                 790                 795                 800

Leu Val Ala Gly Gly Ile Val Ala Gly Ile Phe Leu Ile Phe Ile Glu
                805                 810                 815

Ile Ala Tyr Lys Arg His Lys Asp Ala Arg Arg Lys Gln Met Gln Leu
            820                 825                 830

Ala Phe Ala Ala Val Asn Val Trp Arg Lys Asn Leu Gln Asp Arg Lys
        835                 840                 845

Ser Gly Arg Ala Glu Pro Asp Pro Lys Lys Lys Ala Thr Phe Arg Ala
    850                 855                 860

Ile Thr Ser Thr Leu Ala Ser Ser Phe Lys Arg Arg Ser Ser Lys
865                 870                 875                 880

Asp Thr Ser Thr Gly Gly Gly Arg Gly Ala Leu Gln Asn Gln Lys Asp
                885                 890                 895

Thr Val Leu Pro Arg Arg Ala Ile Glu Arg Glu Glu Gly Gln Leu Gln
            900                 905                 910

Leu Cys Ser Arg His Arg Glu Ser
        915                 920
```

( 2 ) INFORMATION FOR SEQ ID NO: 11:

( i ) SEQUENCE CHARACTERISTICS:
        ( A ) LENGTH: 9 nucleic acids
        ( B ) TYPE: nucleic acid
        ( C ) STRANDEDNESS: double strand
        ( D ) TOPOLOGY: linear ( i i ) MOLECULE TYPE: cDNA ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:11: FROM 1 to 9

( x i ) SEQUENCE DESCRIPTION: SEQ ID NO:11:

CCAGGTGCA         9

( 2 ) INFORMATION FOR SEQ ID NO: 12:

( i ) SEQUENCE CHARACTERISTICS:
        ( A ) LENGTH: 7 amino acids
        ( B ) TYPE: amino acid
        ( C ) STRANDEDNESS: single strand
        ( D ) TOPOLOGY: linear ( i i ) MOLECULE TYPE: peptide ( v i ) ORIGINAL SOURCE:
        ( A ) ORGANISM: mouse
        ( F ) TISSUE TYPE: brain ( i x ) FEATURE:
        ( D ) OTHER INFORMATION: Xaa in location 5 is Ile or Met ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:12: FROM 1 to 7

( x i ) SEQUENCE DESCRIPTION: SEQ ID NO:12:

Trp Asn Gly Met Xaa Gly Glu
 1             5

( 2 ) INFORMATION FOR SEQ ID NO: 13:

( i ) SEQUENCE CHARACTERISTICS:
        ( A ) LENGTH: 7 amino acids
        ( B ) TYPE: amino acid
        ( C ) STRANDEDNESS: single strand
        ( D ) TOPOLOGY: linear ( i i ) MOLECULE TYPE: protein ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:13: FROM 1 to 7

( x i ) SEQUENCE DESCRIPTION: SEQ ID NO:13:

Tyr Thr Ala Asn Leu Ala Ala
 1             5

( 2 ) INFORMATION FOR SEQ ID NO: 14:

( i ) SEQUENCE CHARACTERISTICS:
        ( A ) LENGTH: 20 nucleic acids
        ( B ) TYPE: nucleic acid
        ( C ) STRANDEDNESS: single strand
        ( D ) TOPOLOGY: linear ( i i ) MOLECULE TYPE: other nucleic acid
                      ( sense primer of PCR reaction )

( v i ) ORIGINAL SOURCE:
        ( A ) ORGANISM: mouse
        ( F ) TISSUE TYPE: brain ( i x ) FEATURE:
        ( D ) OTHER INFORMATION: Y in location 1 is T or C, W in
                                    location 9 is A or T and N in location
                                    14 is A, T, G or C ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:14: FROM 1 to 20

( x i ) SEQUENCE DESCRIPTION: SEQ ID NO:14:

TGG AAY GGW ATG ATN GGN GA                                                                                              20

( 2 ) INFORMATION FOR SEQ ID NO: 15:

( i ) SEQUENCE CHARACTERISTICS:
    ( A ) LENGTH: 20 nucleic acids
    ( B ) TYPE: nucleic acid
    ( C ) STRANDEDNESS: single strand
    ( D ) TOPOLOGY: linear ( i i ) MOLECULE TYPE: other nucleic acid (anti-sense primer of PCR
             reaction)

( v i ) ORIGINAL SOURCE:
    ( A ) ORGANISM: mouse
    ( F ) TISSUE TYPE: brain ( i x ) FEATURE:
    ( D ) OTHER INFORMATION: D in location 3 is G, A or T, Y in
          location 6 is T or C, R in location
          8 is A or G and N in location 15 is
          A, T, G or C ( x ) PUBLICATION INFORMATION:
    ( A ) AUTHORS: Masayoshi MISHINA
    ( B ) TITLE: NOVEL PROTEINS AND GENES CODING THE SAME
    ( K ) RELEVANT RESIDUES IN SEQ ID NO:15: FROM 1 to 20

( x i ) SEQUENCE DESCRIPTION: SEQ ID NO:15:

GC DGC YAR RTT DGC NRT RTA                                                                                              20

( 2 ) INFORMATION FOR SEQ ID NO: 16:

( i ) SEQUENCE CHARACTERISTICS:
    ( A ) LENGTH: 3969 nucleic acids
    ( B ) TYPE: nucleic acid
    ( C ) STRANDEDNESS: double strand
    ( D ) TOPOLOGY: linear ( i i ) MOLECULE TYPE: cDNA ( v i ) ORIGINAL SOURCE:
    ( A ) ORGANISM: mouse
    ( F ) TISSUE TYPE: brain ( x ) PUBLICATION INFORMATION:
    ( A ) AUTHORS: Masayoshi MISHINA
    ( B ) TITLE: NOVEL PROTEINS AND GENES CODING THE SAME
    ( K ) RELEVANT RESIDUES IN SEQ ID NO:16: FROM 1 to 3969

( x i ) SEQUENCE DESCRIPTION: SEQ ID NO:16:

```
ATG CGC GGC GCC GGT GGC CCC CGC GGC CCT CGG GGC CCC GCT AAG ATG      48

CTG TTG CTG CTG GCG CTG GCG TGC GCC AGC CCG TTC CCG GAG GAG GTG      96

CCG GGG CCG GGC GCG GCC GGC GGG GGC ACG GGC GGG GCG CGG CCG CTC     144

AAC GTG GCG CTG GTC TTC TCT GGC CCG GCG TAC GCG GCC GAG GCG GCG     192

CGC TTG GGC CCG GCC GTG GCG GCG GCA GTG CGC AGC CCG GGC CTG GAC     240

GTA CGG CCC GTG GCG CTG GTG CTC AAC GGC TCC GAC CCT CGC AGC CTT     288

GTG CTG CAG CTC TGC GAC CTG CTG TCG GGG CTG CGC GTG CAC GGC GTG     336

GTG TTC GAG GAC GAC TCG CGC GCG CCC GCC GTC GCG CCC ATT CTC GAC     384

TTC CTG TCG GCG CAG ACC TCG CTG CCC ATC GTG GCC GTG CAC GGC GGC     432

GCC GCG CTC GTA CTC ACA CCC AAG GAG AAG GGC TCC ACC TTC CTG CAG     480

CTT GGC TCC TCC ACA GAG CAA CAG CTG CAG GTC ATT TTT GAG GTG CTG     528

GAG GAG TAC GAC TGG ACA TCC TTT GTG GCA GTG ACT ACG CGT GCC CCA     576
```

```
GGC CAT CGA GCC TTC TTG TCA TAC ATC GAG GTG CTG ACT GAT GGC AGC      624
CTG GTG GGC TGG GAG CAT CGA GGA GCG CTG ACA CTG GAC CCC GGA GCG      672
GGT GAG GCC GTC CTG GGC GCA CAG CTC CGT AGT GTC AGT GCG CAG ATC      720
CGC CTG CTC TTC TGC GCC CGC GAG GAG GCA GAG CCT GTT TTC CGG GCG      768
GCA GAA GAG GCT GGT CTC ACT GGG CCT GGC TAC GTC TGG TTC ATG GTG      816
GGA CCT CAG CTG GCC GGA GGT GGG GGC TCC GGG GTC CCT GGG GAA CCA      864
CTT CTT CTG CCA GGA GGT GCC CCA CTG CCT GCT GGG CTG TTT GCA GTG      912
CGC TCT GCT GGC TGG CGT GAC GAC TTG GCA CGT CGA GTG GCT GCT GGT      960
GTG GCG GTG GTG GCC AGA GGT GCC CAG GCC CTG CTG CGA GAC TAT GGC     1008
TTC CTG CCT GAG CTG GGC CAT GAC TGT CGC GCC CAG AAT CGC ACC CAC     1056
CGC GGG GAG AGT CTG CAC AGG TAT TTC ATG AAC ATC ACC TGG GAT AAC     1104
CGA GAC TAC TCC TTC AAT GAG GAT GGC TTT CTG GTA AAC CCG TCA CTG     1152
GTA GTC ATC TCC CTC ACC AGA GAC AGG ACG TGG AAA GTG GTG GGC AGC     1200
TGG GAA CAG CAG ACC CTC CGC CTC AAG TAC CCT CTA TGG TCC CGC TAT     1248
GGC CGC TTC CTG CAG CCG GTG GAT GAC ACG CAG CAC CTC ACT GTG GCC     1296
ACG CTG GAG GAG AGA CCT TTT GTC ATT GTA GAG CCT GCA GAC CCC ATC     1344
AGC GGC ACT GCA TC AGA GAC TCG GTT CCC TGC CGG AGC CAG CTC AAC     1392
CGT ACC CAC AGC CCT CCG CCT GAC GCT CCC CGC CCG GAG AAG AGA TGC     1440
TGC AAG GGT TTC TGC ATT GAC ATT TTG AAG AGG CTG GCG CAC ACC ATC     1488
GGT TTC AGC TAT GAC CTC TAC CTG GTT ACC AAC GGC AAG CAT GGC AAG     1536
AAG ATC GAT GGC GTC TGG AAT GGC ATG ATT GGT GAG GTG TTC TAT CAG     1584
CGT GCG GAC ATG GCC ATC GGC TCC CTC ACC ATC AAT GAG GAG CGG TCA     1632
GAG ATC GTG GAC TTC TCC GTC CCT TTT GTA GAG ACA GGC ATC AGC GTC     1680
ATG GTG GCA CGC AGC AAT GGC ACT GTG TCC CCC TCT GCC TTC CTC GAG     1728
CCC TAC AGC CCC GCT GTG TGG GTG ATG ATG TTC GTC ATG TGC CTC ACC     1776
GTG GTC GCC GTC ACA GTT TTC ATC TTT GAG TAC CTC AGT CCT GTG GGC     1824
TAT AAC CGA AGC CTG GCC ACG GGC AAA CGC CCC GGA GGC TCT ACC TTC     1872
ACC ATT GGG AAA TCC ATC TGG CTG CTG TGG GCC CTG GTG TTC AAC AAC     1920
TCC GTG CCA GTG GAG AAT CCT CGG GGC ACC ACC AGC AAG ATC ATG GTG     1968
CTG GTG TGG GCC TTC TTT GCC GTC ATC TTT CTT GCC AGC TAT ACA GCC     2016
AAT CTG GCT GCC TTC ATG ATC CAG GAG GAG TAC GTG GAC ACC GTG TCT     2064
GGG CTC AGC GAC CGG AAG TTC CAG CGG CCC CAG GAG CAA TAC CCA CCC     2112
CTG AAG TTT GGA ACG GTG CCC AAT GGG TCC ACG GAG AAG AAT ATC CGA     2160
AGC AAC TAC CCT GAT ATG CAC AGC TAC ATG GTG CGA TAC AAC CAG CCA     2208
AGA GTG GAG GAG GCG CTC ACT CAG CTC AAG GCA GGG AAA CTG GAC GCC     2256
TTC ATC TAT GAC GCA GCA GTG CTC AAC TAC ATG GCC CGA AAG GAT GAG     2304
GGC TGC AAG CTG GTC ACC ATC GGC TCA GGC AAG GTC TTC GCC ACC ACT     2352
GGT TAT GGC ATC GCC CTA CAC AAG GGC TCC CGC TGG AAG AGG CCC ATC     2400
GAC CTG GCG CTG CTG CAG TTC CTG GGG GAC GAT GAG ATT GAG ATG CTG     2448
GAG CGG CTG TGG CTT TCA GGG ATC TGC CAC AAC GAC AAA ATC GAG GTG     2496
```

| | | | | | | | | | | | | | | | | |
|---|---|---|---|---|---|---|---|---|---|---|---|---|---|---|---|---|
| ATG | AGC | AGC | AAG | CTG | GAT | ATC | GAC | AAC | ATG | GCA | GGT | GTC | TTC | TAC | ATG | 2544 |
| CTC | CTC | GTG | GCC | ATG | GGC | CTC | TCC | TTG | CTG | GTC | TTC | GCC | TGG | GAA | CAC | 2592 |
| CTT | GTG | TAC | TGG | CGA | CTG | CGG | CAC | TGT | CTG | GGG | CCC | ACC | CAC | CGC | ATG | 2640 |
| GAT | TTC | CTA | CTG | GCC | TTC | TCC | AGG | GGT | ATG | TAC | AGC | TGC | TGC | AGC | GCT | 2688 |
| GAG | GCT | GCT | CCG | CCG | CCG | GCC | AAA | CCC | CCG | CCA | CCG | CCG | CAG | CCG | CTG | 2736 |
| CCC | AGT | CCG | GCG | TAT | CCC | GCC | GCT | CGC | CCA | CCC | CCT | GGC | CCC | GCA | CCC | 2784 |
| TTC | GTG | CCC | CGA | GAG | CGC | GCA | GCC | GCC | GAC | CGC | TGG | CGC | CGG | GCC | AAG | 2832 |
| GGC | ACA | GGG | CCC | CCG | GGG | GGC | GCA | GCG | CTA | GCC | GAC | GGC | TTC | CAC | CGA | 2880 |
| TAC | TAC | GGC | CCC | ATC | GAG | CCG | CAG | GGG | CTG | GGC | CTC | GGC | GAG | GCG | CGC | 2928 |
| GCG | GCA | CCG | AGA | GGC | GCA | GCC | GGA | CGC | CCA | CTG | TCC | CCA | CCC | ACC | ACA | 2976 |
| CAG | CCC | CCA | CAG | AAG | CCA | CCA | CCT | TCC | TAC | TTC | GCC | ATC | GTG | CGC | GAG | 3024 |
| CAA | GAG | CCG | GCC | GAG | CCC | CCC | GCC | GGC | GCC | TTC | CCG | GGC | TTT | CCA | TCT | 3072 |
| CCG | CCC | GCT | CCG | CCT | GCC | GCC | GCA | GCC | GCC | GCC | GTC | GGG | CCG | CCA | CTG | 3120 |
| TGC | CGC | CTG | GCT | TTC | GAG | GAC | GAG | AGC | CCG | CCC | GCG | CCC | TCG | GCT | GGC | 3168 |
| CGC | GTT | CTG | ACC | CCG | AGA | GCC | AGC | CGC | TGT | TGG | GTG | GGG | GCG | CGG | GCG | 3216 |
| GCC | CGA | GCG | CTG | GGG | CCC | CGA | CCG | CAC | CAC | CGC | CGC | GTC | CGC | ACC | GCG | 3264 |
| CCA | CCA | CCG | TGC | GCC | TAC | CTG | GAC | CTC | GAG | CCT | TCG | CCT | TCG | GAC | TCC | 3312 |
| GAG | GAT | TCG | GAG | AGC | CTG | GGC | GGA | GCG | TCG | CTC | GGT | GGC | CTG | GAG | CCC | 3360 |
| TGG | TGG | TTC | GCC | GAC | TTC | CCC | TAC | CCG | TAT | GCG | GAG | CGC | CTC | GGG | CCG | 3408 |
| CCG | CCC | GGC | CGC | TAC | TGG | TCG | GTT | GAC | AAG | CTC | GGG | GGC | TGG | CGC | GCT | 3456 |
| GGT | AGC | TGG | GAC | TAC | CTG | CCC | CCG | CGC | GGC | GGC | CCC | GCA | TGG | CAC | TGC | 3504 |
| CGC | CAC | TGC | GCC | AGC | CTG | GAG | CTG | CTA | CCG | CCA | CCA | CGC | CAT | CTC | AGC | 3552 |
| TGC | TCG | CAC | GAC | GGC | CTA | GAC | GGT | GGC | TGG | TGG | GCG | CCT | CCG | CCT | CCA | 3600 |
| CCC | TGG | GCT | GCG | GGG | CCA | CCG | GCC | CCG | CGC | CGG | GCG | CGC | TGT | GGT | TGT | 3648 |
| CCG | CGA | CCG | CAC | CCG | CAC | CGC | CCC | CGG | GCT | TCG | CAC | CGT | GCG | CCC | GCC | 3696 |
| GCC | GCA | CCG | CAC | CAC | CAC | CGA | CAC | AGG | CGC | GCG | GCG | GGT | GGC | TGG | GAC | 3744 |
| CTC | CCG | CCG | CCC | GCG | CCC | ACC | TCG | CGT | TCG | CTG | GAG | GAC | CTG | AGC | TCC | 3792 |
| TGC | CCA | CGG | GCG | GCC | CCC | ACG | CGC | AGG | CTC | ACC | GGG | CCC | TCG | CGC | CAC | 3840 |
| GCG | CGC | CGC | TGT | CCG | CAC | GCT | GCG | CAT | TGG | GGG | CCG | CCC | CTG | CCC | ACC | 3888 |
| GCA | TCT | CAC | CGG | AGA | CAC | CGG | GGC | GGG | GAC | CTG | GGC | ACA | CGC | AGG | GGC | 3936 |
| TCT | GCG | CAC | TTC | TCC | AGC | CTG | GAG | TCC | GAG | GTA | | | | | | 3969 |

( 2 ) INFORMATION FOR SEQ ID NO: 17:

( i ) SEQUENCE CHARACTERISTICS:
        ( A ) LENGTH: 4368 nucleic acids
        ( B ) TYPE: nucleic acid
        ( C ) STRANDEDNESS: double strand
        ( D ) TOPOLOGY: linear ( i i ) MOLECULE TYPE: cDNA ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA ( B ) TITLE: NOVEL PROTEINS AND GENES CODING THE SAME
( K ) RELEVANT RESIDUES IN SEQ ID NO:17: FROM 1 to 4368

( x i ) SEQUENCE DESCRIPTION: SEQ ID NO:17:

| | | | | | | | | | | | | | | | | |
|---|---|---|---|---|---|---|---|---|---|---|---|---|---|---|---|---|
| CGT | TCC | CAA | AAG | AGC | GCC | CCC | AGC | ATC | GGC | ATC | GCT | GTC | ATC | CTC | GTG | 48 |
| GGC | ACT | TCC | GAC | GAA | GTG | GCC | ATA | AAA | GAT | GCC | CAC | GAG | AAA | GAT | GAC | 96 |
| TTC | CAT | CAT | CTC | TCA | GTA | GTT | CCC | CGG | GTG | GAG | CTG | GTA | GCC | ATG | AAC | 144 |
| GAG | ACT | GAC | CCA | AAG | AGC | ATA | ATC | ACC | CGC | ATC | TGC | GAT | CTT | ATG | TCT | 192 |
| GAC | CGG | AAG | ATC | CAG | GGG | GTG | GTG | CTC | GCG | GAT | GAC | ACG | GAC | CAG | GAA | 240 |
| GCC | ATC | GCC | CAG | ATC | CTC | GAT | TTC | ATT | TCT | GCT | CAG | ACT | CTC | ACC | CCC | 288 |
| ATC | CTG | GGC | ATC | CAT | GGG | GGC | TCA | TCT | ATG | ATA | ATG | GCA | GAT | AAG | GAT | 336 |
| GAG | TCC | TCC | ATG | TTC | TTC | CAG | TTT | GGC | CCA | TCC | ATT | GAA | CAG | CAA | GCT | 384 |
| TCT | GTC | ATG | CTC | AAC | ATC | ATG | GAA | GAA | TAC | GAC | TGG | TAC | ATC | TTC | TCC | 432 |
| ATC | GTC | ACC | ACC | TAC | TTC | CCC | GGC | TAC | CAG | GAC | TTC | GTG | AAC | AAG | ATC | 480 |
| CGC | AGC | ACT | ATT | GAG | AAC | AGC | TTT | GTG | GGC | TGG | GAG | CTC | GAG | GAA | GTC | 528 |
| CTC | CTG | CTA | GAC | ATG | TCT | CTA | GAC | GAT | GGC | GAC | TCT | AAG | ATT | CAG | AAT | 576 |
| CAG | CTG | AAG | AAG | CTG | CAG | AGC | CCC | ATC | ATT | CTC | CTC | TAC | TGC | ACA | AAG | 624 |
| GAA | GAA | GCC | ACC | TAC | ATC | TTC | GAA | GTA | GCT | AAC | TCA | GTT | GGG | CTG | ACT | 672 |
| GGC | TAC | GGC | TAC | ACA | TGG | ATC | GTG | CCG | AGT | CTG | GTG | GCG | GGG | GAT | ACA | 720 |
| GAC | ACG | GTG | CCT | TCA | GAG | TTC | CCC | ACG | GGG | CTC | ATC | TCT | GTG | TCA | TAT | 768 |
| GAC | GAA | TGG | GAC | TAT | GGC | CTT | CCT | GCC | AGA | GTG | AGA | GAT | GGG | ATT | GCC | 816 |
| ATC | ATC | ACC | ACT | GCT | GCC | TCG | GAC | ATG | CTG | TCC | GAA | CAC | AGT | TTC | ATC | 864 |
| CCT | GAG | CCC | AAG | AGC | AGT | TGC | TAC | AAC | ACC | CAC | GAG | AAG | AGG | ATC | TAC | 912 |
| CAG | TCT | AAC | ATG | CTG | AAT | AGG | TAT | CTG | ATC | AAC | GTC | ACT | TTT | GAA | GGG | 960 |
| AGA | AAC | CTG | TCC | TTC | AGT | GAA | GAT | GGC | TAC | CAG | ATG | CAT | CCG | AAG | CTG | 1008 |
| GTG | ATA | ATC | CTT | CTG | AAC | AAG | GAG | AGG | AAG | TGG | GAG | AGG | GTG | GGA | AAA | 1056 |
| TGG | AAA | GAC | AAG | TCC | CTG | CAG | ATG | AAA | TAC | TAC | GTG | TGG | CCT | CGA | ATG | 1104 |
| TGT | CCA | GAG | ACT | GAA | GAA | CAG | GAA | GAT | GAC | CAT | CTG | AGC | ATC | GTT | ACC | 1152 |
| TTG | GAG | GAG | GCA | CCG | TTT | GTC | ATT | GTG | GAA | AGT | GTG | GAC | CCT | CTC | AGT | 1200 |
| GGG | ACC | TGC | ATG | CGG | AAT | ACA | GTC | CCG | TGC | CAG | AAG | CGC | ATC | ATC | TCT | 1248 |
| GAG | AAT | AAA | ACA | GAT | GAG | GAA | CCA | GGC | TAC | ATC | AAA | AAA | TGC | TGC | AAG | 1296 |
| GGG | TTT | TGT | ATT | GAT | ATC | CTT | AAG | AAA | ATT | TCT | AAG | TCT | GTG | AAG | TTC | 1344 |
| ACC | TAT | GAC | CTT | TAC | CTG | GTG | ACC | AAT | GGC | AAG | CAT | GGA | AAG | AAA | ATC | 1392 |
| AAC | GGG | ACC | TGG | AAC | GGC | ATG | ATT | GGT | GAG | GTG | GTC | ATG | AAG | AGG | GCC | 1440 |
| TAC | ATG | GCA | GTG | GGA | TCA | CTA | ACT | ATC | AAT | GAA | GAA | CGG | TCA | GAG | GTG | 1488 |
| GTT | GAC | TTC | TCT | GTG | CCC | TTC | ATA | GAG | ACT | GGC | ATC | AGT | GTC | ATG | GTA | 1536 |
| TCA | CGC | AGC | AAT | GGG | ACT | GTG | TCA | CCT | TCT | GCC | TTC | TTA | GAG | CCA | TTC | 1584 |
| AGT | GCT | GAC | GTG | TGG | GTG | ATG | ATG | TTT | GTG | ATG | CTG | CTC | ATT | GTC | TCT | 1632 |
| GCT | GTA | GCT | GTC | TTT | GTC | TTT | GAA | TAC | TTC | AGC | CCT | GTG | GGT | TAC | AAC | 1680 |
| CGG | TGC | CTA | GCT | GAT | GGC | AGA | GAG | CCA | GGC | GGC | CCA | TCT | TTC | ACC | ATC | 1728 |
| GGC | AAA | GCG | ATT | TGG | TTA | CTC | TGG | GGT | CTG | GTG | TTT | CAG | AAC | TCC | GTA | 1776 |
| CCT | GTG | CAG | AAC | CCA | AAG | GGG | ACC | ACC | TCC | AAG | ATC | ATG | GTG | TCA | GTG | 1824 |

| | |
|---|---|
| TGG GCC TTC TTT GCT GTC ATT TTC CTG GCC AGC TAC ACT GCC AAC TTA | 1872 |
| GCC GCC TTC ATG ATC CAA GAG GAG TAT GTG GAC CAG GTT CCG GGC CTG | 1920 |
| AGT GAC AAG AAG TTC CAG AGA CCT AAT GAC TTC TCA CCC CCT TTC CGC | 1968 |
| TTT GGG ACT GTG CCC AAT GGC AGC ACA GAG AGG AAT ATC CGT AAT AAC | 2016 |
| TAT GCA GAA ATG CAT GCC TAC ATG GGA AAG TTC AAC CAA AGG GGT GTA | 2064 |
| GAT GAT GCC TTG CTC TCC CTG AAA ACA GGG AAA CTT GAT GCA TTC ATC | 2112 |
| TAC GAT GCA GCC GTG CTC AAC TAC ATG GCT GGA AGA GAC GAA GGC TGC | 2160 |
| AAG CTG GTG ACC ATT GGC AGT GGC AAG GTC TTT GCT TCT ACG GGC TAT | 2208 |
| GGC ATT GCT ATC CAA AAA GAC TCT GGT TGG AAA CGC AGG TGA CCT T | 2256 |
| GCT ATC CTG CAG CTG TTT GGA GAT GGG GAG ATG GAA GAA CTG GAA GCT | 2304 |
| CTC TGG CTC ACT GGC ATT GCC CAC AAT GAG AAG AAT GAG GTT ATG AGC | 2352 |
| AGC CAG CTG GAC ATT GAC AAC ATG GCG GGC GTC TTT TAT ATG TTG GGG | 2400 |
| GCA GCC ATG GCT CTC AGC CTC ATC ACC TTC ATC TGT GAA CAT CTC TTC | 2448 |
| TAT TGG CAG TTC CGA CAT TGC TTC ATG GGT GTC TGT TCT GGC AAG CCT | 2496 |
| GGC ATG GTC TTC TCC ATC AGC AGA GGT ATC TAC AGC TGT ATC CAC GGA | 2544 |
| GTA GCT ATA GAG GAG CGC CAA TCC GTG ATG AAC TCC CCC ACT GCC ACC | 2592 |
| ATG AAC AAC ACA CAC TCC AAT ATC CTA CGC TTG CTC CGA ACG GCC AAA | 2640 |
| AAC ATG GCC AAC CTG TCT GGA GTC AAC GGC TCC CCC AGT GCC CTG | 2688 |
| GAC TTC ATC CGC CGT GAG TCC TCT GTC TAT GAC ATC TCT GAG CAT CGC | 2736 |
| CGC AGC TTC ACG CAT TCA GAC TGC AAG TCG TAC AAT AAC CCA CCC TGT | 2784 |
| GAG GAA AAC CTG TTC AGT GAC TAC ATT AGT GAG GTA GAG AGA ACA TTT | 2832 |
| GGC AAC TTG CAG CTG AAG GAC AGC AAT GTG TAC CAA GAC CAC TAT CAC | 2880 |
| CAT CAC CAC CGG CCC CAC AGC ATC GGC AGC ACC AGC TCC ATT GAT GGG | 2928 |
| CTC TAT GAC TGT GAC AAC CCA CCC TTT ACC ACC AGC CCA GGT CAA TC | 2976 |
| AGC AAG AAA CCC CTG GAC ATT GGC CTG CCC TCC TCC AAA CAC AGC CAG | 3024 |
| CTC AGC GAC CTG TAC GGC AAG TTC TCT TTC AAG AGT GAC CGC TAC AGT | 3072 |
| GGC CAT GAT GAC TTG ATT CGA TCG GAT GTC TCA GAC ATC TCC ACG CAT | 3120 |
| ACT GTC ACC TAT GGC AAC ATC GAG GGC AAC GCA GCC AAG AGG AGG AAG | 3168 |
| CAG CAA TAT AAG GAC AGT CTA AAG AAG CGG CCA GCC TCG GCC AAA TCT | 3216 |
| AGG AGG GAG TTT GAT GAA ATC GAG CTG GCC TAC CGT CGC CGA CCA CCC | 3264 |
| CGC TCC CCA GAC CAC AAG CGC TAC TTC AGG GAC AAA GAA GGG CTC CGA | 3312 |
| GAC TTC TAC CTG GAC CAG TTC CGA ACA AAG GAG AAC TCG CCT CAC TGG | 3360 |
| GAG CAC GTG GAC TTA ACT GAC ATT TAC AAA GAA CGT AGT TGT GAC TTC | 3408 |
| AAG CGA GAT TCG GTC AGT GGA GGC GGG CCC TGT ACC AAC AGG TCT CAC | 3456 |
| CTT AAA CAC GGA ACA GGC GAT AAG CAC GGA GTG GTA GGC GGG GTG CCT | 3504 |
| GCT CCT TGG GAG AAG AAC CTG ACC AAT GTG GAT TGG GAG GAT AGG TCT | 3552 |
| GGG GGC AAC TTC TGC CGC AGC TGT CCC TCC AAG CTG CAC AAT TAC TCC | 3600 |
| TCT ACG GTG GCA GGG CAA AAC TCG GGC CGG CAG GCC TGC ATC AGG TGT | 3648 |
| GAG GCC TGC AAG AAG GCT GGC AAC CTG TAT GAC ATC AGC GAG GAC AAC | 3696 |
| TCC CTG CAG GAA CTG GAC CAG CCG GCT GCC CCT GTG GCT GTG TCA TCC | 3744 |

| | | | | | | | | | | | | | | | |
|---|---|---|---|---|---|---|---|---|---|---|---|---|---|---|---|
| AAC | GCC | TCC | ACC | ACC | AAG | TAC | CCT | CAA | AGC | CCG | ACT | AAT | TCC | AAG | GCC | 3792 |
| CAG | AAG | AAG | AAT | CGG | AAC | AAA | CTG | CGC | CGG | CAG | CAC | TCC | TAC | GAC | ACC | 3840 |
| TTC | GTG | GAC | CTG | CAG | AAG | GAG | GAG | GCC | GCC | TTG | GCC | CCA | CGC | AGC | GTG | 3888 |
| AGC | CTG | AAA | GAC | AAG | GGC | CGA | TTC | ATG | GAT | GGG | AGC | CCC | TAC | GCC | CAT | 3936 |
| ATG | TTT | GAG | ATG | CCA | GCT | GGT | GAG | AGC | TCC | TTT | GCC | AAC | AAG | TCC | TCA | 3984 |
| GTG | ACC | ACT | GCC | GGA | CAC | CAT | CAC | AAC | AAT | CCC | GGC | AGC | GGC | TAC | ATG | 4032 |
| CTC | AGC | AAG | TCG | CTC | TAC | CCT | GAC | CGG | GTC | ACG | CAA | AAC | CCT | TTC | ATC | 4080 |
| CCC | ACT | TTT | GGG | GAT | GAT | CAG | TGC | TTG | CTT | ACG | GCA | GCA | AAT | CCT | ACT | 4128 |
| TCT | TCA | GGC | AGC | CCA | ACG | GTG | GCA | GGG | GCG | TCG | AAA | ACA | AGG | CCG | GAC | 4176 |
| TTC | CGG | GCC | CTT | GTC | ACC | AAT | AAG | CCA | GTG | GTG | TCG | GCC | CTT | CAT | GGG | 4224 |
| GCT | GTG | CCA | GGT | CGT | TTC | CAG | AAG | GAC | ATT | TGT | ATA | GGG | AAC | CAG | TCC | 4272 |
| AAC | CCC | TGT | GTG | CCT | AAC | AAC | AAA | AAC | CCC | AGG | GCT | TTC | AAT | GGC | TCC | 4320 |
| AGC | AAT | GGA | CAT | GTT | TAT | GAG | AAA | CTT | TCT | AGT | ATT | GAG | TCT | GAT | GTC | 4368 |

( 2 ) INFORMATION FOR SEQ ID NO: 18:

( i ) SEQUENCE CHARACTERISTICS:

( A ) LENGTH: 2760 nucleic acids
  ( B ) TYPE: nucleic acid
  ( C ) STRANDEDNESS: double strand
  ( D ) TOPOLOGY: linear ( i i ) MOLECULE TYPE: cDNA ( v i ) ORIGINAL SOURCE:
  ( A ) ORGANISM: mouse
  ( F ) TISSUE TYPE: brain ( x ) PUBLICATION INFORMATION:
  ( A ) AUTHORS: Masayoshi MISHINA
  ( B ) TITLE: NOVEL PROTEINS AND GENES CODING THE SAME
  ( K ) RELEVANT RESIDUES IN SEQ ID NO:18: FROM 1 to 2760

( x i ) SEQUENCE DESCRIPTION: SEQ ID NO:18:

| | | | | | | | | | | | | | | | |
|---|---|---|---|---|---|---|---|---|---|---|---|---|---|---|---|
| CGC | GCT | GCC | TGC | GAC | CCC | AAG | ATT | GTC | AAC | ATC | GGC | GCG | GTG | CTG | AGC | 48 |
| ACG | CGC | AAG | CAC | GAG | CAG | ATG | TTC | CGC | GAG | GCA | GTA | AAC | CAG | GCC | AAT | 96 |
| AAG | CGA | CAC | GGC | TCT | TGG | AAG | ATA | CAG | CTC | AAC | GCC | ACT | TCT | GTC | ACC | 144 |
| CAC | AAG | CCC | AAC | GCC | ATA | CAG | ATG | GCC | CTG | TCA | GTG | TGT | GAG | GAC | CTC | 192 |
| ATC | TCT | AGC | CAG | GTC | TAC | GCT | ATC | CTA | GTT | AGT | CAC | CCG | CCT | ACT | CCC | 240 |
| AAC | GAC | CAC | TTC | ACT | CCC | ACC | CCT | GTC | TCC | TAC | ACA | GCT | GGC | TTC | TAC | 288 |
| AGA | ATC | CCC | GTC | CTG | GGG | CTG | ACT | ACC | CGA | ATG | TCC | ATC | TAC | TCT | GAC | 336 |
| AAG | AGC | ATC | CAC | CTG | AGC | TTC | CTT | CGC | ACC | GTA | CCA | CCC | TAC | TCC | CAC | 384 |
| CAG | TCC | AGC | GTC | TGG | TTT | GAG | ATG | ATG | CGC | GTC | TAC | AAC | TGG | AAC | CAT | 432 |
| ATC | ATC | CTG | CTG | GTC | AGC | GAT | GAC | CAC | GAG | GGC | CGG | GCA | GCG | CAG | AAG | 480 |
| CGC | CTG | GAG | ACG | TTG | CTG | GAG | GAG | CGT | GAG | TCC | AAG | GCA | GAG | AAG | GTG | 528 |
| CTG | CAG | TTT | GAC | CCA | GGA | ACC | AAG | AAT | GTG | ACG | GCT | CTG | CTG | ATG | GAA | 576 |
| GCC | CGG | GAC | CTG | GAA | GCC | CGG | GTC | ATC | ATC | CTT | TCT | GCA | AGC | GAG | GAC | 624 |
| GAC | GCT | GCC | ACC | GTA | TAC | CGC | GCA | GCC | GCG | ATG | CTG | AAC | ATG | ACT | GGC | 672 |
| TCT | GGG | TAC | GTG | TGG | CTC | GTC | GGG | GAG | CGC | GAG | ATC | TCT | GGG | AAT | GCC | 720 |

-continued

| | | | | | | | | | | | | | | | |
|---|---|---|---|---|---|---|---|---|---|---|---|---|---|---|---|
|CTG|CGC|TAC|GCT|CCT|GAC|GGC|ATC|ATC|GGA|CTT|CAG|CTA|ATC|AAC|GGC|768|
|AAG|AAC|GAG|TCG|GCC|CAC|ATC|AGT|GAC|GCT|GTG|GGC|GTG|GTG|GCA|CAG|816|
|GCA|GTC|CAC|GAG|CTC|CTA|GAA|AAG|GAG|AAC|ATC|ACT|GAT|CCA|CCG|CGG|864|
|GGT|TGC|GTG|GGC|AAC|ACC|AAC|ATC|TGG|AAG|ACA|GGA|CCA|CTG|TTC|AAG|912|
|AGG|GTG|CTG|ATG|TCT|TCC|AAG|TAT|GCA|GAT|GGA|GTG|ACT|GGC|CGT|GTG|960|
|GAA|TTC|AAT|GAG|GAT|GGG|GAC|CGG|AAG|TTT|GCC|AAC|TAT|AGT|ATC|ATG|1008|
|AAC|CTG|CAG|AAC|CGC|AAG|CTG|GTG|CAA|GTG|GGC|ATC|TAC|AAT|GGT|ACC|1056|
|CAT|GTC|ATC|CCA|AAT|GAC|AGG|AAG|ATC|ATC|TGG|CCA|GGA|GGA|GAG|ACA|1104|
|GAG|AAG|CCT|CGA|GGA|TAC|CAG|ATG|TCC|ACC|AGA|CTA|AAG|ATA|GTG|ACA|1152|
|ATC|CAC|CAA|GAA|CCC|TTC|GTG|TAT|GTC|AAG|CCC|ACA|ATG|AGT|GAT|GGC|1200|
|ACA|TGC|AAA|GAG|GAG|TTC|ACA|GTC|AAT|GGT|GAC|CCT|GTC|AAG|AAG|GTG|1248|
|ATC|TGT|ACG|GGG|CCT|AAT|GAC|ACA|TCC|CCA|GGA|AGC|CCA|CGT|CAC|ACA|1296|
|GTG|CCC|CAG|TGC|TGT|TAT|GGC|TTC|TGC|GTT|GAC|CTG|CTC|ATC|AAG|CTG|1344|
|GCA|CGG|ACC|ATG|AAT|TTT|ACC|TAC|GAG|GTG|CAC|CTT|GTG|GCA|GAT|GGC|1392|
|AAG|TTT|GGC|ACA|CAG|GAG|CGG|GTA|AAC|AAC|AGC|AAC|AAA|AAG|GAG|TGG|1440|
|AAC|GGA|ATG|ATG|GGA|GAG|CTG|CTC|AGT|GGT|CAA|GCA|GAC|ATG|ATC|GTG|1488|
|GCT|CCA|CTG|ACC|ATT|AAC|AAT|GAG|CGT|GCG|CAG|TAC|ATA|GAG|TTC|TCC|1536|
|AAG|CCC|TTC|AAG|TAC|CAG|GGC|CTG|ACC|ATT|CTG|GTC|AAG|AAG|GAG|ATC|1584|
|CCT|CGG|AGC|ACA|CTG|GAC|TCA|TTC|ATG|CAG|CCC|TTT|CAG|AGC|ACA|CTG|1632|
|TGG|CTG|CTG|GTG|GGG|CTG|TCA|GTT|CAT|GTG|GTG|GCC|GTG|ATG|CTG|TAC|1680|
|CTG|CTG|GAC|CGC|TTC|AGT|CCC|TTT|GGC|CGA|TTT|AAG|GTG|AAC|AGC|GAG|1728|
|GAG|GAG|GAG|GAG|GAT|GCA|CTG|ACC|CTG|TCC|TCT|GCC|ATG|TGG|TTT|TCC|1776|
|TGG|GGC|GTC|CTG|CTC|CAG|TCT|GGC|ATT|GGG|GAA|GGT|GCC|CCC|CGG|AGT|1824|
|TTC|TCT|GCT|CGT|ATC|CTA|GGC|ATG|GTG|TGG|GCT|GGT|TTT|GCC|ATG|ATC|1872|
|ATC|GTG|GCT|TCC|TAC|ACT|GCC|AAC|CTG|GCA|GCC|TTC|CTG|GTG|CTG|GAT|1920|
|AGG|CCT|GAG|GAG|CGC|ATC|ACA|GGC|ATC|AAT|GAC|CCC|AGG|CTC|AGA|AAC|1968|
|CCC|TCA|GAC|AAG|TTC|ATC|TAT|GCA|ACT|GTA|AAA|CAG|AGC|TCT|GTG|GAT|2016|
|ATC|TAC|TTC|CGG|AGG|CAG|GTG|GAG|TTG|AGC|ACC|ATG|TAC|CGG|CAC|ATG|2064|
|GAG|AAG|CAC|AAT|TAT|GAG|AGT|GCA|GCT|GAG|GCC|ATC|CAG|GCT|GTG|CGG|2112|
|GAC|AAC|AAG|CTC|CAT|GCC|TTC|ATC|TGG|GAC|TCA|GCT|GTG|CTG|GAG|TTT|2160|
|GAG|GCT|TCA|CAG|AAG|TGC|GAT|CTG|GTG|ACC|ACG|GGT|GAG|CTG|TTC|TTC|2208|
|CGC|TCC|GGC|TTT|GGC|ATC|GGC|ATG|CGC|AAG|GAC|AGC|CCC|TGG|AAG|CAA|2256|
|AAT|GTG|TCC|CTG|TCC|ATA|CTC|AAG|TCC|CAT|GAG|AAT|GGC|TTC|ATG|GAA|2304|
|GAC|CTG|GAT|AAG|ACA|TGG|GTT|CGG|TAT|CAA|GAA|TGT|GAC|TCC|CGC|AGC|2352|
|AAT|GCC|CCT|GCC|ACC|CTC|ACT|TTT|GAG|AAC|ATG|GCA|GGG|TCT|TC|ATG|2400|
|CTG|GTG|GCT|GGA|GGC|ATC|GTA|GCT|GGG|ATC|TTC|CTC|ATT|TTC|ATC|GAG|2448|
|ATC|GCC|TAC|AAG|CGA|CAC|AAG|GAT|GCC|CGT|AGG|AAG|CAG|ATG|CAG|CTG|2496|
|GCT|TTT|GCA|GCC|GTG|AAC|GTG|TGG|AGG|AAG|AAC|CTG|CAG|GAT|AGA|AAG|2544|
|AGT|GGT|AGA|GCA|GAG|CCC|GAC|CCT|AAA|AAG|AAA|GCC|ACA|TTT|AGG|GCT|2592|
|ATC|ACC|TCC|ACC|CTG|GCC|TCC|AGC|TTC|AAG|AGA|CGT|AGG|TCC|TCC|AAA|2640|

| | | | | | | | | | | | | | | | | |
|---|---|---|---|---|---|---|---|---|---|---|---|---|---|---|---|---|
|GAC|ACG|AGC|ACC|GGG|GGT|GGA|CGC|GGC|GCT|TTG|CAA|AAC|CAA|AAA|GAC|2688|
|ACA|GTG|CTG|CCG|CGA|CGC|GCT|ATT|GAG|AGG|GAG|GAG|GGC|CAG|CTG|CAG|2736|
|CTG|TGT|TCC|CGT|CAT|AGG|GAG|AGC| | | | | | | | |2760|

( 2 ) INFORMATION FOR SEQ ID NO: 19:

( i ) SEQUENCE CHARACTERISTICS:
        ( A ) LENGTH: 2760 nucleic acids
        ( B ) TYPE: nucleic acid
        ( C ) STRANDEDNESS: double strand
        ( D ) TOPOLOGY: linear ( i i ) MOLECULE TYPE: cDNA ( v i ) ORIGINAL SOURCE:
        ( A ) ORGANISM: mouse
        ( F ) TISSUE TYPE: brain ( x ) PUBLICATION INFORMATION:
        ( A ) AUTHORS: Masayoshi MISHINA
        ( B ) TITLE: NOVEL PROTEINS AND GENES CODING THE SAME
        ( K ) RELEVANT RESIDUES IN SEQ ID NO:19: FROM 1 to 2760

( x i ) SEQUENCE DESCRIPTION: SEQ ID NO:19:

| | | | | | | | | | | | | | | | |
|---|---|---|---|---|---|---|---|---|---|---|---|---|---|---|---|
|CGC|GCT|GCC|TGC|GAC|CCC|AAG|ATT|GTC|AAC|ATC|GGC|GCG|GTG|CTG|AGC|48|
|ACG|CGC|AAG|CAC|GAG|CAG|ATG|TTC|CGC|GAG|GCA|GTA|AAC|CAG|GCC|AAT|96|
|AAG|CGA|CAC|GGC|TCT|TGG|AAG|ATA|CAG|CTC|AAC|GCC|ACT|TCT|GTC|ACC|144|
|CAC|AAG|CCC|AAC|GCC|ATA|CAG|ATG|GCC|CTG|TCA|GTG|TGT|GAG|GAC|CTC|192|
|ATC|TCT|AGC|CAG|GTC|TAC|GCT|ATC|CTA|GTT|AGT|CAC|CCG|CCT|ACT|CCC|240|
|AAC|GAC|CAC|TTC|ACT|CCC|ACC|CCT|GTC|TCC|TAC|ACA|GCT|GGC|TTC|TAC|288|
|AGA|ATC|CCC|GTC|CTG|GGG|CTG|ACT|ACC|CGA|ATG|TCC|ATC|TAC|TCT|GAC|336|
|AAG|AGC|ATC|CAC|CTG|AGC|TTC|CTT|CGC|ACC|GTA|CCA|CCC|TAC|TCC|CAC|384|
|CAG|TCC|AGC|GTC|TGG|TTT|GAG|ATG|ATG|CGC|GTC|TAC|AAC|TGG|AAC|CAT|432|
|ATC|ATC|CTG|CTG|GTC|AGC|GAT|GAC|CAC|GAG|GGC|CGG|GCA|GCG|CAG|AAG|480|
|CGC|CTG|GAG|ACG|TTG|CTG|GAG|GAG|CGT|GAG|TCC|AAG|GCA|GAG|AAG|GTG|528|
|CTG|CAG|TTT|GAC|CCA|GGA|ACC|AAG|AAT|GTG|ACG|GCT|CTG|CTG|ATG|GAA|576|
|GCC|CGG|GAC|CTG|GAA|GCC|CGG|GTC|ATC|ATC|CTT|TCT|GCA|AGC|GAG|GAC|624|
|GAC|GCT|GCC|ACC|GTA|TAC|CGC|GCA|GCC|GCG|ATG|CTG|AAC|ATG|ACT|GGC|672|
|TCT|GGG|TAC|GTG|TGG|CTC|GTC|GGG|GAG|CGC|GAG|ATC|TCT|GGG|AAT|GCC|720|
|CTG|CGC|TAC|GCT|CCT|GAC|GGC|ATC|ATC|GGA|CTT|CAG|CTA|ATC|AAC|GGC|768|
|AAG|AAC|GAG|TCG|GCC|CAC|ATC|AGT|GAC|GCT|GTG|GGC|GTG|GTG|GCA|CAG|816|
|GCA|GTC|CAC|GAG|CTC|CTA|GAA|AAG|GAG|AAC|ATC|ACT|GAT|CCA|CCG|CGG|864|
|GGT|TGC|GTG|GGC|AAC|ACC|AAC|ATC|TGG|AAG|ACA|GGA|CCA|CTG|TTC|AAG|912|
|AGG|GTG|CTG|ATG|TCT|TCC|AAG|TAT|GCA|GAT|GGA|GTG|ACT|GGC|CGT|GTG|960|
|GAA|TTC|AAT|GAG|GAT|GGG|GAC|CGG|AAG|TTT|GCC|AAC|TAT|AGT|ATC|ATG|1008|
|AAC|CTG|CAG|AAC|CGC|AAG|CTG|GTG|CAA|GTG|GGC|ATC|TAC|AAT|GGT|ACC|1056|
|CAT|GTC|ATC|CCA|AAT|GAC|AGG|AAG|ATC|ATC|TGG|CCA|GGA|GGA|GAG|ACA|1104|
|GAG|AAG|CCT|CGA|GGA|TAC|CAG|ATG|TCC|ACC|AGA|CTA|AAG|ATA|GTG|ACA|1152|
|ATC|CAC|CAA|GAA|CCC|TTC|GTG|TAT|GTC|AAG|CCC|ACA|ATG|AGT|GAT|GGC|1200|
|ACA|TGC|AAA|GAG|GAG|TTC|ACA|GTC|AAT|GGT|GAC|CCT|GTC|AAG|AAG|GTG|1248|

-continued

| | | | | | | | | | | | | | | | |
|---|---|---|---|---|---|---|---|---|---|---|---|---|---|---|---|
| ATC | TGT | ACG | GGG | CCT | AAT | GAC | ACA | TCC | CCA | GGA | AGC | CCA | CGT | CAC | ACA | 1296 |
| GTG | CCC | CAG | TGC | TGT | TAT | GGC | TTC | TGC | GTT | GAC | CTG | CTC | ATC | AAG | CTG | 1344 |
| GCA | CGG | ACC | ATG | AAT | TTT | ACC | TAC | GAG | GTG | CAC | CTT | GTG | GCA | GAT | GGC | 1392 |
| AAG | TTT | GGC | ACA | CAG | GAG | CGG | GTA | AAC | AAC | AGC | AAC | AAA | AAG | GAG | TGG | 1440 |
| AAC | GGA | ATG | ATG | GGA | GAG | CTG | CTC | AGT | GGT | CAA | GCA | GAC | ATG | ATC | GTG | 1488 |
| GCT | CCA | CTG | ACC | ATT | AAC | AAT | GAG | CGT | GCG | CAG | TAC | ATA | GAG | TTC | TCC | 1536 |
| AAG | CCC | TTC | AAG | TAC | CAG | GGC | CTG | ACC | ATT | CTG | GTC | AAG | AAG | GAG | ATC | 1584 |
| CCT | CGG | AGC | ACA | CTG | GAC | TCA | TTC | ATG | CAG | CCC | TTT | CAG | AGC | ACA | CTG | 1632 |
| TGG | CTG | CTG | GTG | GGG | CTG | TCA | GTT | CAT | GTG | GTG | GCC | GTG | ATG | CTG | TAC | 1680 |
| CTG | CTG | GAC | CGC | TTC | AGT | CCC | TTT | GGC | CGA | TTT | AAG | GTG | AAC | AGC | ACC | 1728 |
| AGT | GAC | CAG | TCA | AAT | GCA | CTG | ACC | CTG | TCC | TCT | GCC | ATG | TGG | TTT | TCC | 1776 |
| TGG | GGC | GTC | CTG | CTC | AAC | TCT | GGC | ATT | GGG | GAA | GGT | GCC | CCC | CGG | AGT | 1824 |
| TTC | TCT | GCT | CGT | ATC | CTA | GGC | ATG | GTG | TGG | GCT | GGT | TTT | GCC | ATG | ATC | 1872 |
| ATC | GTG | GCT | TCC | TAC | ACT | GCC | AAC | CTG | GCA | GCC | TTC | CTG | GTG | CTG | GAT | 1920 |
| AGG | CCT | GAG | GAG | CGC | ATC | ACA | GGC | ATC | AAT | GAC | CCC | AGG | CTC | AGA | AAC | 1968 |
| CCC | TCA | GAC | AAG | TTC | ATC | TAT | GCA | ACT | GTA | AAA | CAG | AGC | TCT | GTG | GAT | 2016 |
| ATC | TAC | TTC | CGG | AGG | CAG | GTG | GAG | TTG | AGC | ACC | ATG | TAC | CGG | CAC | ATG | 2064 |
| GAG | AAG | CAC | AAT | TAT | GAG | AGT | GCA | GCT | GAG | GCC | ATC | CAG | GCT | GTG | CGG | 2112 |
| GAC | AAC | AAG | CTC | CAT | GCC | TTC | ATC | TGG | GAC | TCA | GCT | GTG | CTG | GAG | TTT | 2160 |
| GAG | GCT | TCA | CAG | AAG | TGC | GAT | CTG | GTG | ACC | ACG | GGT | GAG | CTG | TTC | TTC | 2208 |
| CGC | TCC | GGC | TTT | GGC | ATC | GGC | ATG | CGC | AAG | GAC | AGC | CCC | TGG | AAG | CAA | 2256 |
| AAT | GTG | TCC | CTG | TCC | ATA | CTC | AAG | TCC | CAT | GAG | AAT | GGC | TTC | ATG | GAA | 2304 |
| GAC | CTG | GAT | AAG | ACA | TGG | GTT | CGG | TAT | CAA | GAA | TGT | GAC | TCC | CGC | AGC | 2352 |
| AAT | GCC | CCT | GCC | ACC | CTC | ACT | TTT | GAG | AAC | ATG | GCA | GGG | GTC | TTC | ATG | 2400 |
| CTG | GTG | GCT | GGA | GGC | ATC | GTA | GCT | GGG | ATC | TTC | CTC | ATT | TTC | ATC | GAG | 2448 |
| ATC | GCC | TAC | AAG | CGA | CAC | AAG | GAT | GCC | CGT | AGG | AAG | CAG | ATG | CAG | CTG | 2496 |
| GCT | TTT | GCA | GCC | GTG | AAC | GTG | TGG | AGG | AAG | AAC | CTG | CAG | GAT | AGA | AAG | 2544 |
| AGT | GGT | AGA | GCA | GAG | CCC | GAC | CCT | AAA | AAG | AAA | GCC | ACA | TTT | AGG | GCT | 2592 |
| ATC | ACC | TCC | ACC | CTG | GCC | TCC | AGC | TTC | AAG | AGA | CGT | AGG | TCC | TCC | AAA | 2640 |
| GAC | ACG | AGC | ACC | GGG | GGT | GGA | CGC | GGC | GCT | TTG | CAA | AAC | CAA | AAA | GAC | 2688 |
| ACA | GTG | CTG | CCG | CGA | CGC | GCT | ATT | GAG | AGG | GAG | GAG | GGC | CAG | CTG | CAG | 2736 |
| CTG | TGT | TCC | CGT | CAT | AGG | GAG | AGC | | | | | | | | | 2760 |

I claim:

1. An isolated glutamate receptor represented by an amino acid sequence selected from the group consisting of Sequence ID No. 1, No. 2, No. 3 and No. 4.

2. The glutamate receptor according to claim 1, wherein the receptor is derived from a mouse.

3. An isolated nucleic acid encoding the glutamate receptor according to claim 1.

4. The nucleic acid according to claim 3 which is represented by a base sequence selected from the group consisting of Sequence ID No. 5, No. 6, No. 7 and No. 16.

5. A modified glutamate receptor represented by an amino acid sequence described in Sequence ID No. 8 or No. 9.

6. The modified glutamate receptor according to claim 5, wherein the receptor is derived from mouse.

7. A nucleic acid encoding the modified glutamate receptor according to claim 5.

8. The nucleic acid according to claim 7 which is represented by a base sequence described in Sequence ID No. 17 or No. 18.

9. A nucleic acid encoding a modified glutamate receptor represented by a base sequence described in Sequence ID No. 19.

* * * * *